(12) United States Patent
Brossmer et al.

(10) Patent No.: US 10,472,381 B2
(45) Date of Patent: Nov. 12, 2019

(54) SIALIC ACID DERIVATIVES

(71) Applicants: Reinhard Brossmer, Heidelberg (DE);
Horst Prescher, Basel (CH)

(72) Inventors: Reinhard Brossmer, Heidelberg (DE);
Horst Prescher, Basel (CH)

(73) Assignees: Reinhard Brossmer, Heidelberg (DE);
Horst Prescher, Basel (CH)

( * ) Notice: Subject to any disclaimer, the term of this patent is extended or adjusted under 35 U.S.C. 154(b) by 0 days.

(21) Appl. No.: 15/121,585

(22) PCT Filed: Feb. 25, 2015

(86) PCT No.: PCT/EP2015/053884
§ 371 (c)(1),
(2) Date: Aug. 25, 2016

(87) PCT Pub. No.: WO2015/128344
PCT Pub. Date: Sep. 3, 2015

(65) Prior Publication Data
US 2016/0362436 A1 Dec. 15, 2016

(30) Foreign Application Priority Data
Feb. 25, 2014 (EP) .................... 14156512

(51) Int. Cl.
*A01N 43/04* (2006.01)
*A61K 31/70* (2006.01)
*C07H 15/04* (2006.01)
*A61K 31/7028* (2006.01)

(52) U.S. Cl.
CPC .......... *C07H 15/04* (2013.01); *A61K 31/7028* (2013.01)

(58) Field of Classification Search
None
See application file for complete search history.

(56) References Cited

FOREIGN PATENT DOCUMENTS

| WO | 03000709 | 1/2003 |
|---|---|---|
| WO | 2013097942 | 7/2013 |
| WO | 2013190103 | 12/2013 |
| WO | 2015128344 | 9/2015 |

OTHER PUBLICATIONS

Abdu-Allah et al., CD22-antagonists with nanomolar potency: the synergistic effect of hydrophobic groups at C-2 and C-9 of sialic acid scaffold, Bioorganic & Medicinal Chemistry, vol. 19, No. 6, Mar. 15, 2011, pp. 1966-1971.
Collins et al., High-affinity ligand probes of CD22 overcome the threshold set by cis ligands to allow for binding, endocytosis, and killing of B cells, J Immunol., vol. 177, No. 5, Sep. 2006, pp. 2994-3003.
Courtney et al., Sialylated multivalent antigens engage CD22 in trans and inhibit B cell activation, PNAS, vol. 106, No. 8, 2009, pp. 2500-2505.
Fiorina et al., Targeting CD22 reprograms B-cells and reverses autoimmune diabetes, Diabetes, vol. 57, No. 11, Nov. 2008, pp. 3013-3024.
Isecke et al., Synthesis of 5-N- and 9-N-thioacylated sialic acids, Tetrahedron, vol. 50, Issue 25, 1994, pp. 7445-7460.
Kelm et al., C-4 Modified Sialosides Enhance Binding to Siglec-2 (CD22): Towards Potent Siglec Inhibitors for Immunoglycotherapy, Angewandte Chemie International Edition, vol. 52, No. 13, Mar. 25, 2013, pp. 3616-3620.
Kelm et al., The ligand-binding domain of CD22 is needed for inhibition of the B cell receptor signal, as demonstrated by a novel human CD22-specific inhibitor compound, J Exp Med., vol. 195, No. 9, May 2002, pp. 1207-1213.
Lehmann et al., Sialic acid-specific lectins: occurrence, specificity and function, Cell Mol Life Sci., vol. 63, No. 12, Jun. 2006, pp. 1331-1354.
Magesh et al., High-Affinity Ligands of Siglec Receptors and their Therapeutic Potentials, Current Medicinal Chemistry, vol. 18, No. 23, 2011, pp. 3537-3550.
Mesch et al., From a Library of MAG Antagonists to Nanomolar CD22 Ligands, ChemMedChem, vol. 7, Issue 1, Jan. 2, 2012, pp. 134-143.
Mesch et al., Kinetic and thermodynamic properties of MAG antagonists, Carbohydrate Research, vol. 345(10), 2010, pp. 1348-1359.
O'Reilly et al., Siglecs as targets for therapy in immune-cell-mediated disease, Trends in Pharmacological Sciences, vol. 30, Issue 5, May 2009, pp. 240-248.
International Application No. PCT/EP2015/053884, International Search Report and Written Opinion dated Apr. 8, 2015, 12 pages.
Rautio et al., Prodrugs: Design and Clinical Applications, Nature Drug Discovery Reviews, vol. 7, 2008, pp. 255-270.
Schauer, Sialic acids: fascinating sugars in higher animals and man, Zoology, vol. 107, No. 1, Mar. 2004, pp. 49-64.
Schweizer et al., Targeting of CD22-positive B-cell lymphoma cells by synthetic divalent sialic acid analogues, European Journal of Immunology, vol. 42, Issue 10, 2012, pp. 2792-2802.
Tedder et al., CD22: a multifunctional receptor that regulates B lymphocyte survival and signal transduction, Adv Immunol., vol. 88, 2005, pp. 1-50.
Varki, Sialic acids in human health and disease, Trends in Mol. Med., vol. 48, No. 8, pp. 351-360, Aug. 2008.

*Primary Examiner* — Patrick T Lewis
(74) *Attorney, Agent, or Firm* — Kilpatrick Townsend & Stockton LLP

(57) ABSTRACT

Sialic acid derivatives of the formula (I)

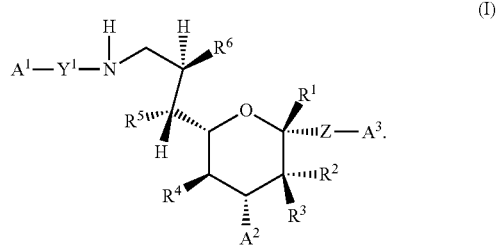

17 Claims, No Drawings

SIALIC ACID DERIVATIVES

CROSS-REFERENCE TO RELATED APPLICATIONS

This application is a U.S. National Stage of International Application No. PCT/EP2015/068872, filed Feb. 25, 2015, which claims the benefit of European Patent Application No. 14156512.7, filed Feb. 24, 2014, the entire contents of which are incorporated herein by reference.

The invention relates to derivatives of sialic acid, to processes for preparing them, to their use, especially as active pharmaceutical ingredients, and also to pharmaceutical active ingredient compositions which comprise such compounds.

Sialic acid is the generic term for a family of 9-carbon atom sugars which represent all derivatives of neuramic acid (Neu) and of keto-deoxy-nonulosonic acid (KDN). They are typically located at the exposed, non-reducing ends of oligosaccharide chains. Sialic acids play multivarious roles in mammals and in the human body (Schauer (2004) Zoology, 107, 49-64; Varki (2008) Trends in Mol. Med., 14, 8, 351-360). Furthermore, they are utilized by many pathogens in order, for example, to achieve efficient infection or in order to evade the immune system of the host (Glycoconjugate J. 2006, vol. 23, issue 1-2, all articles). Many such functions are regulated via proteins which recognize sialic acids (Lehmann et al. (2006) Cell-Mol. Life Sci. 63, 1331-1354).

One subgroup of such proteins are the Siglecs. They are lectins of the Ig type which are characterized by an N-terminal V-set domain, which allows specific recognition of sialic acids. A review of the types of Siglec proteins hitherto disclosed, and of diseases potentially treatable using Siglec inhibitors, is found in Trends in "Pharmacological Sciences 2009, 30 (5), 240-248" and "Current Medicinal Chemistry 2011, 18, 3537-3550" and in the references therein.

CD22 (Siglec-2) is highly expressed in B cells. It is known that disorders based on B cells, especially lymphomas and autoimmune diseases, can be treated by means of CD22 ligands (Tedder et al. (2005) Advances in Immunology 88, 1-50; Fiorina et al. (2008) Diabetes 57, 3013-3024).

Furthermore, antibodies and polymeric sialic acids have already been developed as ligands with therapeutic suitability for Siglec-2 (Courtney et al. (2009) PNAS 106, 8, 2500-505; Collins et al. (2006) Journal of Immunology 177, 2994-3003). The polymers have the disadvantage of very high molecular weight, an undefinable and non-uniform size and composition.

It is known that certain monomeric derivatives of sialic acid with substitutions at position C-9 (WO 03/000709 and J. Exp. Med. 2002, 195, 9, 1207-1213), and also with substitutions at C-9, C-5 and C-2 (Chem Med Chem 2012, 7, 134-143), act as ligands for CD22 and have potential suitability as medicaments. It is also known that sialic acid derivatives with substitutions at C-9 and C-4 and with a methoxy group at C-2 (Angewandte Chemie Int. Ed., 2013, 53, 3616-3620) have increased affinity for Siglec-2.

Dimeric derivatives of sialic acid are known from WO 2013/190103 and WO 2013/097942.

Although the known derivatives already have high affinities, there is nevertheless a broad room for improvements, especially with regard to affinity and selectivity. In addition, there is room for improvements in pharmacological tolerability and administration forms and also in stability in plasma and liver.

It is an object of the invention to provide compounds with which advantages are achieved within parts at least of the stated areas.

It has been found that certain monomeric sialic acid derivatives, with a nitrogen substituted in the 9-position and with further substituents at the 4- and 2-positions, are particularly suitable as Siglec-2 (CD22) ligands.

The invention accordingly provides a sialic acid derivative of the formula (I),

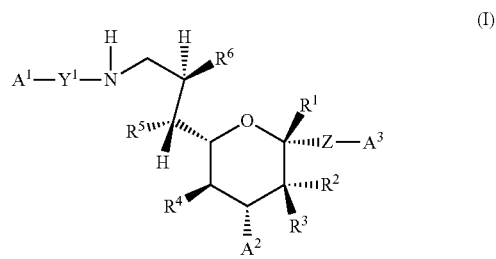

(I)

where the symbols have the following definitions:

$A^1$ is a group $D^1\text{-}[Y^2\text{-}D^2\text{-}]_{m\text{-}}$;

$D^1$ is a mono- or polycyclic aromatic, partially unsaturated or saturated $C_3\text{-}C_{14}$ hydrocarbon radical or a mono- or polycyclic aromatic, partially unsaturated or saturated three- to twelve-membered heterocyclic radical, the stated radicals being unsubstituted or substituted one or more times by a group X;

$D^2$ is a mono- or polycyclic aromatic, partially unsaturated or saturated $C_3\text{-}C_{14}$ hydrocarbon radical or a mono- or polycyclic aromatic, partially unsaturated or saturated three- to eight-membered heterocyclic radical, the stated radicals being unsubstituted or substituted one or more times by a group X;

$Y^1$ is ~C(O)—, ~S(O)$_2$—, ~NHC(O)—, ~($C_1\text{-}C_2$ alkyl)-, ~($C_1\text{-}C_2$ alkyl)-C(O)—, ~CH=CH—C(O)—, ~C≡C—C(O)—, ~($C_1\text{-}C_2$ alkyl)-S(O)$_2$—, ~OC(O)—, ~($C_1\text{-}C_2$ alkyl)-OC(O)— or ~($C_1\text{-}C_2$ alkyl)-NHC(O)—, where ~ denotes the bond to the group $A^1$;

$Y^2$ is —O—, —C(O)—, —S(O)$_2$—, —CH$_2$— or a bond;

$A^2$ is a) a group —OS(O)$_2$OL or b) a group —N(R$^x$)—W;

W is a) a group ~SO$_3$L, ~SO$_2$CF$_3$ or ~SO$_2$NR$^x_2$ or b) a group $D^3$-$Y^3$—;

$Y^3$ is a bond or a group ~O(CO)NHS(O)$_2$—, ~NHC(O)—, ~OC(O)—, ~CH$_2$OC(O)—, ~S(O)$_2$—, ~C(O)—, ~($C_1$-$C_2$ alkyl)-C(O)—, ~($C_1$-$C_2$ alkyl)-NHC(O)— or ~($C_1$-$C_2$ alkyl)-S(O)$_2$—, where ~ denotes the bond to the group $D^3$;

$D^3$ is a) $C_1$-$C_6$ alkyl, where optionally one or more non-terminal CH$_2$ groups are replaced by O, N(R$^x$) and/or C(O), and where optionally one or more H atoms in the stated groups are replaced by a group X, or b) is a mono- or polycyclic aromatic, partially unsaturated or saturated $C_3$-$C_{14}$ hydrocarbon radical or a mono- or polycyclic aromatic, partially unsaturated or saturated three- to eight-membered heterocyclic radical, the stated radicals being unsubstituted or substituted one or more times by a group X;

$A^3$ is
a) a $C_1$-$C_8$ alkyl, where optionally
   a. one or more non-terminal —$CH_2$— groups are replaced by S, O, N($R^x$) and/or C(O), or
   b. a —$CH_2CH_2CH_2$— group is replaced by 1,2-phenyldiyl, 1,3-phenyldiyl or 1,4-phenyldiyl, and where optionally one or more H atoms in the stated groups are replaced by a group X, or
b) is a mono- or polycyclic aromatic, partially unsaturated or saturated $C_3$-$C_{14}$ hydrocarbon radical or a mono- or polycyclic aromatic, partially unsaturated or saturated three- to eight-membered heterocyclic radical, the stated radicals being unsubstituted or substituted one or more times by a group X;
X is identically or differently halogen, cyano, nitro, hydroxyl, mercapto, amino, carboxyl, carboxymethyl, hydroxylamino, azido, $B(OH)_2$, SO, $SO_3M$, $OSO_3M$, $SO_2NH_2$, $SO_2CF_3$, $PO_3M$, $OPO_3M$, cyanomethyl, alkyl, haloalkyl, alkyloxy, haloalkyloxy, alkylamino, dialkylamino, trialkylamino, formyl, alkylcarbonyl, alkylsulfonyl, alkylsulfoxyl, alkylaminosulfonyl, dialkylaminosulfonyl, alkyloxycarbonyl, alkylcarbonyloxy, aminocarbonyl, alkylaminocarbonyl, alkylcarbonylamino, dialkylaminocarbonyl, oxo (=O), thioxo (=S), $C_1$-$C_8$ alkylimino (=N—$C_1$-$C_8$ alkyl) or $C_1$-$C_8$ alkyloximino (=N—O—$C_1$-$C_8$ alkyl), the alkyl groups in these radicals containing 1 to 6 carbon atoms;
m is 0, 1 or 2;
Z is ~O—, ~S—, —ON=CH~, ~ON($R^x$)—, ~N($R^x$)— or ~4-1H-(1,2,3)triazol-1-yl-, where ~ denotes the bond to the group $A^3$;
$R^1$ is C(O)OM;
$R^2$ is H, F, Cl, $NR^x$ or $OR^x$;
$R^3$ is H, F, Cl, $NR^x$ $OR^x$;
$R^4$ is $N(R^x)C(O)CH_2OH$ or $N(R^x)C(O)R^x$;
$R^5$, $R^6$ are identically or differently OH or $OR^x$;
L is a cation;
M is $C_1$-$C_4$ alkyl or a cation;
$R^x$ is identically or differently H, $R^y$ or $R^z$;
$R^y$ is identically or differently $C_1$-$C_4$ alkyl, phenyl or benzyl, and
$R^z$ is identically or differently —C(O)—$C_1$-$C_4$ alkyl, —C(O)-phenyl or C(O)—$CH_2$-phenyl.

Likewise provided by the invention is a pharmaceutical preparation comprising at least one sialic acid derivative of the formula (I) or a pharmacologically tolerated salt or prodrug thereof, and a pharmacologically tolerated carrier.

Additionally provided by the invention, moreover, is a sialic acid derivative of the formula (I) or a pharmacologically tolerated salt or prodrug thereof, as medicament.

By way of example, modifications to individual substituents in pharmacologically active molecules, to form prodrug forms, are described in Nature Drug Discovery Reviews, 2008, 7, 255-270 and in Hydrolysis in Drug and Prodrug Metabolism, Wiley-VCH, 2003, Bernard Testa and Joachim M. Mayer.

The invention also provides a sialic acid derivative of the formula (I), or a pharmacologically tolerated salt or prodrug thereof, for the treatment or prevention of allergies, autoimmune disorders, chronic inflammations, paraplegia, multiple sclerosis, cancer, viral disorders, for example AIDS, bacterial disorders, for example streptococci, parasitic disorders, for example Chagas disease, diseases in which the immune response is disrupted in the context of B cell activation, such as Common Variable Immunodeficiency (CVID) and IgA deficiency, in diseases of the hematopoietic organs and of the blood, and also in cancer, for example lymphomas and myelomas, and also for the regulation of the immune system, for example in the case of vaccinations.

Further provided by the invention is a sialic acid derivative of the formula (I), or a pharmacologically tolerated salt or prodrug thereof, for use in the production of a medicament for the regulation of the immune system, for example in the case of vaccinations, and also for the treatment of allergies, autoimmune disorders, chronic inflammations, paraplegia, multiple sclerosis, cancer, viral disorders, for example AIDS, bacterial disorders, for example streptococci, parasitic disorders, for example Chagas disease, diseases in which the immune response is disrupted in the context of B cell activation, such as Common Variable Immunodeficiency (CVID) and IgA deficiency, in diseases of the hematopoietic organs and of the blood, and also in cancer, for example lymphomas and myelomas.

Likewise provided by the invention is a method for regulating the immune system, for example in the case of vaccinations, and also for the treatment of diseases whose course or activity can be influenced by the Siglec ligands, more particularly from the group of allergies, autoimmune disorders, chronic inflammations, paraplegia, multiple sclerosis, cancer, viral disorders, for example AIDS, bacterial disorders, for example streptococci, parasitic disorders, for example Chagas disease, diseases in which the immune response is disrupted in the context of B cell activation, such as Common Variable Immunodeficiency (CVID) and IgA deficiency, in diseases of the hematopoietic organs and of the blood, and also in cancer, for example lymphomas and myelomas, in which a person affected by the disease is administered a preferably therapeutically effective amount of a sialic acid derivative of the formula (I) or of a pharmacologically tolerated salt or prodrug thereof.

The sialic acid derivatives of the formula (I) exhibit a significantly increased affinity in comparison to hitherto-disclosed monovalent CD22 ligands. Even at low concentrations, they influence the calcium excretion of B cells in vitro.

Through the combination of substituents C-9 and C-4 of the sialic acid framework with methoxy substituents of C-2 that are larger than that already known, an unexpectedly greatly increased affinity for CD22 has been achieved. This is so particularly against the background that for another member of the Siglec family (MAG or Siglec-4), combination of substituents at positions C-9, C-4 and C-2 resulted in a lowering of the affinity (Carbohydrate Research, 2010, 345, 1348-1359). The sialic acid derivatives of the formula (I) have a high activity for CD22 and, in contrast to polymers, have an unambiguous and definable structure in each case. In comparison with other high-affinity, dimeric CD22 ligands known to date, they have a significantly reduced molecular weight. Apart from sialic acid, moreover, they contain no further carbohydrates and can be modified to form prodrugs in a simple way. The compounds are prepared without using cell cultures or enzymes, thus enabling production on the industrial scale.

The term "sialic acid derivative of the formula (I)" encompasses all stereoisomeric forms of the compound of the formula (I), especially E/Z or cis/trans isomers in the case of substituted double bonds or rings, and also stereoisomers resulting from the centers of chirality in the compounds of the formula (I), more particularly enantiomers and diastereoisomers, in pure form or in the form of mixtures of any composition, with the individual centers of chirality present in each case in the (S)- or (R)-form.

The individual stereoisomers may be prepared, for example, by enrichment of the isomeric mixtures in accordance with customary techniques, such as chromatography or crystallization, or by use of isomerically pure starting materials. The enrichment of the isomers may take place at the stage of the reactants, intermediates or end products of the formula (I). The isomers encompassed in accordance with the invention also include all tautomeric forms of compounds (I), and all mesomorphous forms.

Furthermore, the term "sialic acid derivative of the formula (I)" encompasses solvates, examples being hydrates or adducts with alcohols, and also all crystal modifications.

The invention also provides pharmacologically effective metabolites of the compounds (I). More particularly the term "metabolites" encompasses cleavage products generated by enzymes that occur "in vivo", such as esterases, amidases and other enzymes.

Furthermore, the term "sialic acid derivatives of the formula (I)" encompasses pharmacologically tolerated salts of the compounds (I), including internal salts (zwitterions).

Generally speaking, the salts contemplated are the salts of those cations, or the acid addition salts of those acids, whose cations or anions, respectively, do not adversely affect the pharmacological activity of the compounds (I).

Cations contemplated include, in particular, ions of the alkali metals, preferably lithium, sodium and potassium, of the alkaline earth metals, preferably calcium and magnesium, and of the transition metals, preferably manganese, copper, zinc and iron, and also ammonium, in which case, if desired, one to four hydrogen atoms may be replaced by $R^Y$, preferably ammonium, dimethylammonium, diisopropylammonium, tetramethylammonium, triethylammonium, tetrabutylammonium, 2-(2-hydroxyeth-1-oxy)eth-1-ylammonium, di(2-hydroxyeth-1-yl)ammonium, trimethylbenzylammonium, and also phosphonium ions, sulfonium ions, preferably tri($C_1$-$C_4$ alkyl)sulfonium, and sulfoxonium ions, preferably tri($C_1$-$C_4$ alkyl)sulfoxonium. Preferred are Na, Li, K, Ca, Mg and ammonium (optionally substituted); particularly preferred are Na, Li and K; especially preferred is Na.

Anions of pharmacologically tolerated acid addition salts are, for example, chloride, bromide, fluoride, hydrogensulfate, sulfate, dihydrogenphosphate, hydrogenphosphate, nitrate, hydrogencarbonate, carbonate, hexafluorosilicate, hexafluorophosphate, benzoate, the anions of $C_1$-$C_4$ alkanoic acids, preferably formate, acetate, propionate and butyrate, and of other organic acids, such as pivalic acid, maleic acid, succinic acid, pimelic acid, fumaric acid, malic acid, sulfamic acid, phenylpropionic acid, gluconic acid, ascorbic acid, nicotinic acid, citric acid and adipic acid.

Unless otherwise indicated, symbols which are used more than once may have the same or different definitions independently of one another.

The definitions of the symbols indicated in the formula (I) are as follows:

halogen (halo): fluorine (fluoro), chlorine (chloro), bromine (bromo) and iodine (iodo);

alkyl: saturated, straight-chain, branched or cyclic hydrocarbon radicals having for example 1 to 8 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1,1-dimethylpropyl, 1-ethylpropyl, hexyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methylpentyl, 2-methylpentyl, 3-methylpentyl, 4-methylpentyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, cyclopropyl, cyclobutyl, 1-methylcyclopropyl, 2-methylcyclopropyl, cyclopentyl, 2,2-dimethylcyclopropyl, 2,3-dimethylcyclopropyl, cyclohexyl and cyclooctyl;

haloalkyl: straight-chain, branched or cyclic alkyl groups having for example 1 to 6 carbon atoms (as specified above), some or all of the hydrogen atoms in these groups having been replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methylethyl, 1-fluorocyclopropyl, heptafluoropropyl or nonafluorobutyl;

alkyloxy: alkyloxy groups with a saturated, straight-chain, branched or cyclic alkyl radical, this radical being from the above-stated group of the alkyls, and containing 1 to 6 carbon atoms;

haloalkyloxy: haloalkyloxy groups with a straight-chain, branched or cyclic haloalkyl radical, this radical being from the above-stated group of the haloalkyls, and containing 1 to 6 carbon atoms;

alkylamino: alkylamino groups with a saturated, straight-chain, branched or cyclic alkyl radical, this radical being from the above-stated group of the alkyls, and containing 1 to 4 carbon atoms;

dialkylamino: dialkylamino groups with saturated, straight-chain, branched or cyclic alkyl radicals, these radicals being, identically or differently, from the above-stated group of the alkyls, and containing 1 to 4 carbon atoms;

trialkylamino: trialkylamino groups with saturated, straight-chain, branched or cyclic alkyl radicals, these radicals being, identically or differently, from the above-stated group of the alkyls, and containing 1 to 4 carbon atoms;

alkylcarbonyl: alkylcarbonyl groups with a saturated, straight-chain, branched or cyclic alkyl radical, this radical being from the above-stated group of the alkyls, and containing 1 to 4 carbon atoms;

alkylsulfonyl: alkylsulfonyl groups with a saturated, straight-chain, branched or cyclic alkyl radical, this radical being from the above-stated group of the alkyls, and containing 1 to 4 carbon atoms;

alkylsulfoxyl: alkylsulfoxyl groups with a saturated, straight-chain, branched or cyclic alkyl radical, this radical being from the above-stated group of the alkyls, and containing 1 to 4 carbon atoms;

alkylaminosulfonyl: alkylaminosulfonyl groups with a saturated, straight-chain, branched or cyclic alkyl radical, this radical being from the above-stated group of the alkyls, and containing 1 to 4 carbon atoms;

dialkylaminosulfonyl: dialkylaminosulfonyl groups with saturated, straight-chain, branched or cyclic alkyl radicals, these radicals being from the above-stated group of the alkyls, and containing 1 to 4 carbon atoms;

alkyloxycarbonyl: alkyloxycarbonyl groups with a saturated, straight-chain, branched or cyclic alkyl radical, this radical being from the above-stated group of the alkyls, and containing 1 to 4 carbon atoms;

alkylcarbonyloxy: alkylcarbonyloxy groups with a saturated, straight-chain, branched or cyclic alkyl radical, this radical being from the above-stated group of the alkyls, and containing 1 to 4 carbon atoms;

alkylaminocarbonyl: alkylaminocarbonyl groups with a saturated, straight-chain, branched or cyclic alkyl radical, this radical being from the above-stated group of the alkyls, and containing 1 to 4 carbon atoms;

dialkylaminocarbonyl: dialkylaminocarbonyl groups with saturated, straight-chain, branched or cyclic alkyl radicals, these radicals being from the above-stated group of the alkyls, and containing 1 to 4 carbon atoms;

alkylimino: alkylimino groups with a saturated, straight-chain, branched or cyclic alkyl radical, this radical being from the above-stated group of the alkyls, and containing 1 to 4 carbon atoms;

alkyloximino: alkyloximino groups with a saturated, straight-chain, branched or cyclic alkyl radical, this radical being from the above-stated group of the alkyls, and containing 1 to 4 carbon atoms;

alkylcarbonylamino: alkylcarbonylamino groups with a saturated, straight-chain, branched or cyclic alkyl radical, this radical being from the above-stated group of the alkyls, and containing 1 to 4 carbon atoms.

The skilled person is aware that a cyclic or branched alkyl group has at least three carbon atoms. In accordance with the invention, the term "alkyl" is also used for alkylene groups (alkanediyl groups). This is evident from the context in each case.

Mono- or polycyclic, aromatic, partially unsaturated or saturated $C_3$-$C_{14}$ hydrocarbon radical for $D^2$ denotes, for example:

a) $C_6$-$C_{14}$ aryldiyl, more particularly phenylene-1,4-diyl, phenylene-1,3-diyl, phenylene-1,2-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, biphenylene-1,2-diyl, biphenylene-1,3-diyl, biphenylene-1,4-diyl, biphenylene-1,5-diyl, biphenylene-1,6-diyl, biphenylene-1,7-diyl, biphenylene-1,8-diyl, biphenylene-2,3-diyl, biphenylene-2,6-diyl and biphenylene-2,7-diyl;

b) $C_3$-$C_8$ cycloalkyldiyl, more particularly trans-cyclopropane-1,2-diyl, cyclopropane-1,1-diyl, trans-cyclobutane-1,3-diyl, cis-cyclobutane-1,3-diyl, trans-cyclopentane-1,3-diyl, cis-cyclohexane-1,4-diyl, trans-cyclohexane-1,4-diyl, trans-cycloheptane-1,4-diyl, trans-cyclooctane-1,5-diyl and cubane-1,4-diyl.

Monocyclic aromatic, partially unsaturated or saturated three- to eight-membered heterocyclic radical for $D^2$ denotes, for example:

a) non-aromatic, saturated or partially unsaturated 5- or 6-membered heterocyclodiyl, containing one to three nitrogen atoms and/or one oxygen or sulfur atom or one or two oxygen and/or sulfur atoms, more particularly trans-tetrahydrofuran-2,5-diyl, trans-tetrahydrofuran-2,4-diyl, cis-tetrahydrofuran-2,5-diyl, trans-tetrahydrothiene-2,5-diyl, trans-tetrahydrothiene-2,4-diyl, trans-pyrrolidine-2,5-diyl, trans-pyrrolidine-2,4-diyl, isoxazolidine-2,4-diyl, isoxazolidine-2,5-diyl, isothiazolidine-2,4-diyl, isothiazolidine-2,5-diyl, pyrazolidine-1,3-diyl, trans-oxazolidine-2,4-diyl, trans-thiazolidine-2,5-diyl, imidazolidine-1,3-diyl, trans-imidazolidine-2,4-diyl, pyrroline-1,3-diyl, trans-pyrroline-2,4-diyl, trans-pyrroline-2,5-diyl, trans-piperidine-2,5-diyl, piperidine-1,4-diyl, trans-dioxane-2,5-diyl, trans-tetrahydropyrane-2,5-diyl, trans-hexahydropyridazine-3,6-diyl, trans-hexahydropyridazine-1,4-diyl, trans-hexahydropyrimidine-2,5-diyl, hexahydropyrimidine-1,3-diyl, hexahydropyrimidine-1,4-diyl, piperazine-1,4-diyl, trans-piperazine-2,5-diyl and piperazine-1,3-diyl;

b) 5-membered heteroaryldiyl, containing one to four nitrogen atoms or one to three nitrogen atoms and/or one sulfur or oxygen atom, more particularly furan-2,4-diyl, furan-2,5-diyl, thiophene-2,4-diyl, thiophene-2,5-diyl, pyrrole-2,4-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, 1,2,4-thiadiazole-3,5-diyl, 1,3,4-thiadiazole-2,5-diyl, isooxazole-3,5-diyl, thiazole-2,4-diyl, thiazole-2,5-diyl, isothiazole-3,5-diyl, imidazole-2,4-diyl, 2H-tetrazole-2,5-diyl, 1H(1,2,4)triazole-2,5-diyl, 1H(1,2,3)triazole-1,4-diyl, and 1H-(1,2,3)triazole-1,5-diyl;

c) 6-membered heteroaryldiyl, containing one to three or one to four nitrogen atoms, more particularly pyridine-2,5-diyl, pyridine-2,4-diyl, pyridine-2,3-diyl, pyridazine-3,6-diyl, pyrimidine-2,5-diyl, pyrimidine-2,6-diyl, pyrazine-2,5-diyl and tetrazine-3,5-diyl.

Polycyclic aromatic, partially unsaturated or saturated heterocyclic radical for $D^2$ denotes, for example:
1-benzofuran-4,7-diyl, 1-benzofuran-2,7-diyl, 2-benzofuran-4,7-diyl, 2-benzofuran-3,6-diyl, chromene-5,8-diyl, chromene-3,7-diyl, xanthene-1,4-diyl, xanthene-2,6-diyl, indazole-4,7-diyl, purine-2,8-diyl, 4H-quinolizine-6,9-diyl, 3-isoquinoline-1,4-diyl, phthalazine-1,4-diyl, 1,8-naphthyridine-2,6-diyl, quinoxaline-2,6-diyl, quinazoline-5,8-diyl, cinnoline-5,8-diyl, pteridine-2,6-diyl, indolizine-2,6-diyl, indole-4,7-diyl, indole-2,5-diyl, indole-3,6-diyl, isoindole-4,7-diyl, isoindole-2,5-diyl, carbazole-1,4-diyl, acridine-1,4-diyl, phenoxazine-1,4-diyl, benzoxazole-4,7-diyl, benzothiazole-4,7-diyl, benzoimidazole-4,7-diyl, 1H-benzotriazole-4,7-diyl and benzothiophenediyl.

Mono- or polycyclic, aromatic, partially unsaturated or saturated $C_3$-$C_{14}$ hydrocarbon radical for $D^1$, $D^3$ and $A^3$ denotes, for example:

a) $C_6$-$C_{14}$ aryl, more particularly phenyl, 1-naphthyl, 2-naphthyl, 1-biphenylene, 2-biphenylene, 1-pyrenyl, 1-anthracenyl, 2-anthracenyl, 9-anthracenyl, 4-indenyl, 2-fluorenyl, 3-fluorenyl, 9-fluorenyl and 3-phenanthrenyl;

b) $C_3$-$C_{14}$ cycloalkenyl or $C_5$-$C_{14}$ cycloalkadienyl, more particularly cyclopropenyl, cyclobutenyl, cyclopentenyl, cyclohexenyl, cycloheptenyl, cyclooctenyl, cyclopentadien-1-yl, cyclohexadien-1-yl and cyclooctadien-1-yl;

c) $C_3$-$C_8$ cycloalkyl, more particularly cyclopropyl, cyclobutyl, cyclopentyl, cyclohexyl, cycloheptyl, adamantan-1-yl, cuban-1-yl, bicyclo[4.4.0]decan-2-yl and cyclooctyl.

Monocyclic aromatic, partially unsaturated or saturated three- to eight-membered heterocyclic radical for $D^1$, $D^3$ and $A^3$ denotes, for example:

a) non-aromatic, saturated or partially unsaturated 4-, 5-, 6- or 7-membered heterocyclyl, containing one to four nitrogen atoms and/or one oxygen or sulfur atom or one or two oxygen and/or sulfur atoms, more particularly 1-aza-2-oxocyclobut-1-yl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 4,5-dihydro-1,3-oxazol-2-yl, 4,5-dihydro-1,3-oxazol-4-yl, 4,5-dihydro-1,3-oxazol-5-yl, 4,5-dihydro-1,3-thiazol-2-yl, 4,5-dihydro-1,3-thiazol-4-yl, 4,5-dihydro-1,3-thiazol-5-yl, 4,5-dihydro-4H-1,3-oxazin-2-yl, 4,5-dihydro-4H-1,3-thiazin-2-yl, 4,5,6,7-tetrahydro-1,3-oxazepin-2-yl, 4,5,6,7-tetrahydro-1,3-thiazepin-2-yl, 2-thiazolidinyl, 4-thiazolidinyl, 5-thiazolidinyl, 2-imidazolidinyl, 4-imidazolidinyl, 5-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 4-morpholinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 5H-tetrazol-5-yl, 1H-tetrazol-5-yl, 2H-tetrazol-5-yl, 1-piperazinyl and 2-piperazinyl;

b) 5-membered heteroaryl, containing one to four nitrogen atoms or one to three nitrogen atoms and/or one sulfur or oxygen atom: more particularly 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-isoxazolyl, 4-isooxazolyl, 5-isooxazolyl, 2-thiazolyl, 4-thiazolyl, 5-thiazolyl, 2-isothiazolyl, 4-isothiazolyl, 5-isothiazolyl, 2-imidazolyl, 4-imidazolyl, 1,2,5-thiadiazol-3-yl, 1,2,4-thiadiazol-3-yl, 1,2,4-thiadiazol-5-yl, 1,2,5-oxadiazol-3-yl, 1,2,4-oxadiazol-3-yl, 1,2,4-oxadiazol-5-yl, 1,2,3-thiadiazol-4-yl, 1,2,3-thiadiazol-5-yl, 1,2,3,4-thiatriazol-5-yl, 1H-(1,2,3)triazol-1-yl, 1H-(1,2,3)triazol-4-yl, 1H-(1,2,3)triazol-5-yl, 1H-(1,3,4)triazol-1-yl and 1H-(1,3,4)triazol-2-yl;

c) 6-membered heteroaryl, containing one to three or one to four nitrogen atoms: more particularly 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

Polycyclic aromatic, partially unsaturated or saturated heterocyclic radical for $D^1$, $D^3$ and $A^3$ denotes, for example: 1-benzofuran-2-yl, 1-benzofuran-3-yl, 1-benzofuran-5-yl, 1-benzofuran-6-yl, 1-benzofuran-7-yl, 2-benzofuran-1-yl, 2-benzofuran-3-yl, 2-benzofuran-4-yl, 2-benzofuran-5-yl, 2-benzofuran-6-yl, 2-benzofuran-7-yl, 2H-chromen-3-yl, 2H-chromen-4-yl, 2H-chromen-5-yl, 2H-chromen-6-yl, 2H-chromen-7-yl, 2H-chromen-8-yl, xanthen-1-yl, xanthen-4-yl, xanthen-9-yl, indazol-1-yl, indazol-3-yl, indazol-4-yl, indazol-5-yl, indazol-6-yl, indazol-7-yl, purin-2-yl, purin-6-yl, purin-7-yl, purin-8-yl, quinolin-2-yl, quinolin-3-yl, quinolin-4-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, phthalazin-1-yl, phthalazin-3-yl, phthalazin-5-yl, phthalazin-6-yl, 1,8-naphthyridin-2-yl, 1,8-naphthyridin-3-yl, 1,8-naphthyridin-4-yl, 1,8-naphthyridin-6-yl, 1,8-naphthyridin-7-yl, quinoxalin-2-yl, quinoxalin-5-yl, quinoxalin-6-yl, quinazolin-4-yl, quinazolin-6-yl, cinnolin-3-yl, cinnolin-4-yl, cinnolin-6-yl, pteridin-2-yl, pteridin-4-yl, pteridin-6-yl, pteridin-7-yl, indolizin-1-yl, indol-1-yl, indol-2-yl, indol-3-yl, indol-5-yl, indol-6-yl, indol-7-yl, indol-8-yl, isoindol-1-yl, isoindol-2-yl, isoindol-4-yl, isoindol-5-yl, carbazol-9-yl, acridin-9-yl, phenoxazin-10-yl, 1-benzothiophen-2-yl, 1-benzothiophen-3-yl, 1-benzothiophen-5-yl, 1-benzothiophen-6-yl, 1-benzothiophen-7-yl, 1-benzothiophen-8-yl, benzimidazol-1-yl, benzimidazol-2-yl, benzimidazol-5-yl, benzimidazol-6-yl, benzimidazol-7-yl, benzimidazol-8-yl, 1H-benzotriazol-1-yl, 1H-benzotriazol-5-yl, 1H-benzotriazol-6-yl, 1H-benzotriazol-7-yl, 1H-benzotriazol-8-yl, 4H-3,1-benzoxazin-2-yl, 4H-2-benzopyran-2-yl, 2H-isoquinolin-3-yl, benzothiazol-2-yl, benzothiazol-5-yl, benzothiazol-6-yl, benzothiazol-7-yl, benzothiazol-8-yl, benzoxazol-2-yl, benzoxazol-5-yl, benzoxazol-6-yl, benzoxazol-7-yl or benzoxazol-8-yl.

The stated linear or cyclic hydrocarbon radicals and heterocycles may be unsubstituted or substituted, the substituents being selected preferably from the group X. Preferred, depending on the respective chain size or ring size, are 1, 2, 3 or 4 substituents; in the case of halogen substituents, preference is also given to substitution up to the maximum possible number (persubstitution).

The symbols in the formula (I) advantageously have the following definitions:

$A^1$ is advantageously a group $D^1$-[$Y^2$-$D^2$-]$_m$-.

$D^1$ is advantageously a mono- or polycyclic aromatic or saturated $C_3$-$C_{14}$ hydrocarbon radical or a monocyclic aromatic, partially unsaturated or saturated four- to six-membered heterocyclic radical, the stated radicals being unsubstituted or substituted one or more times by a group X.

$D^2$ is advantageously a group phenylene-1,4-diyl, phenylene-1,3-diyl, pyridine-2,5-diyl, pyridazine-3,6-diyl, pyrimidine-2,5-diyl, pyrimidine-2,6-diyl, pyrazine-2,5-diyl, trans-cyclobutane-1,3-diyl, trans-cyclopentane-1,3-diyl, trans-cyclohexane-1,4-diyl, cubane-1,4-diyl, thiophene-2,5-diyl, pyrrole-2,4-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, isooxazole-3,5-diyl, imidazole-2,4-diyl, 2H-tetrazole-2,5-diyl, 1H(1,2,4)-triazole-2,5-diyl, 1H(1,2,3)-triazole-1,4-diyl and 1H(1,2,3)-triazole-1,5-diyl, the stated radicals being unsubstituted or substituted one or more times by a group X.

$Y^1$ is advantageously ~C(O)—, ~S(O)$_2$—, ~NHC(O)—, ~CH$_2$C(O)—, ~CH$_2$—S(O)$_2$—, ~OC(O)—, ~CH$_2$—OC(O)— or ~CH$_2$NHC(O)—, where ~ denotes the bond to the group $A^1$.

$Y^2$ is advantageously —O—, —CH$_2$— or a bond.

$A^2$ is advantageously
  a) a group —OS(O)$_2$OL or
  b) a group —N(R$^x$)—W.

W is advantageously
  a) a group ~SO$_3$L, ~SO$_2$CF$_3$ or ~SO$_2$NR$^x$$_2$ or
  b) a group $D^3$-$Y^3$—.

$Y^3$ is advantageously a bond or a group ~NHC(O)—, ~OC(O)—, ~CH$_2$OC(O)—, ~S(O)$_2$, ~C(O)—, ~CH$_2$—C(O)—, ~CH$_2$—NHC(O)— or ~CH$_2$—S(O)$_2$—, where ~ denotes the bond to the group $D^3$.

$D^3$ is advantageously
  a) a $C_1$-$C_6$ alkyl, where optionally one or more non-terminal CH$_2$ groups are replaced by O and where optionally one or more H atoms in the stated groups are replaced by a group X,
  b) a monocyclic or polycyclic aromatic or saturated $C_3$-$C_{14}$ hydrocarbon radical or a monocyclic aromatic, partially unsaturated or saturated four- to six-membered heterocyclic radical, the stated radicals being unsubstituted or substituted one or more times by a group X.

$A^3$ is advantageously a $C_3$-$C_8$ alkyl, where optionally
  a. one or more non-terminal —CH$_2$— groups are replaced by S or O, or
  b. a —CH$_2$CH$_2$CH$_2$— group is replaced by 1,2-phenyldiyl, 1,3-phenyldiyl or 1,4-phenyldiyl, and where optionally one or more H atoms in the stated groups are replaced by a group X;

X is advantageously identically or differently halogen, hydroxyl, amino, carboxyl, carboxymethyl, SO$_3$M, OSO$_3$M, SO$_2$NH$_2$, SO$_2$CF$_3$, alkyl, haloalkyl, alkyloxy, alkylamino, dialkylamino, trialkylamino, alkylsulfonyl, alkyloxycarbonyl, alkylcarbonyloxy, alkylaminocarbonyl, alkylcarbonylamino or oxo (=O), the alkyl groups in these radicals containing 1 to 3 carbon atoms.

m is 0 or 1.

Z is advantageously ~O—, ~S— or ~4-1H-(1,2,3)triazol-1-yl-, where ~ denotes the bond to the group $A^3$.

$R^1$ is advantageously C(O)OM.

$R^2$ is advantageously H or F.

$R^3$ is advantageously H, F, Cl or $OR^x$.

$R^4$ is advantageously $NHC(O)CH_2OH$ or $NHC(O)CH_3$.

$R^5$, $R^6$ are advantageously identically or differently OH or $OR^z$.

L is advantageously a cation.

M is advantageously a $C_1$-$C_3$ alkyl or a cation.

$R^x$ is advantageously identically or differently H, $R^y$ or $R^z$.

$R^y$ is advantageously identically or differently $C_1$-$C_3$ alkyl, phenyl or benzyl.

$R^z$ is advantageously identically or differently —C(O)—$C_1$-$C_3$ alkyl or —C(O)-phenyl.

The meanings of the definitions of the symbols as indicated in the formula (I) are advantageously as follows:

halogen (halo): fluorine (fluoro), chlorine (chloro) and bromine (bromo);

alkyl: saturated, straight-chain, branched or cyclic hydrocarbon radicals having for example 1 to 8 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1,1-dimethylpropyl, 1-ethylpropyl, hexyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methylpentyl, 2-methylpentyl, 3-methylpentyl, 4-methylpentyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, cyclopropyl, cyclobutyl, 1-methylcyclopropyl, 2-methylcyclopropyl, cyclopentyl, 2,2-dimethylcyclopropyl, 2,3-dimethylcyclopropyl, cyclohexyl and cyclooctyl;

haloalkyl: straight-chain, branched or cyclic alkyl groups having for example 1 to 3 carbon atoms (as specified above), some or all of the hydrogen atoms in these groups having been replaced by halogen atoms: such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methylethyl, 1-fluorocyclopropyl or heptafluoropropyl;

alkyloxy: alkyloxy groups with a saturated, straight-chain, branched or cyclic alkyl radical, this radical being from the above-stated group of the alkyls, and containing 1 to 3 carbon atoms;

alkylamino: alkylamino groups with a saturated, straight-chain, branched or cyclic alkyl radical, this radical being from the above-stated group of the alkyls, and containing 1 to 2 carbon atoms;

dialkylamino: dialkylamino groups with saturated, straight-chain, branched or cyclic alkyl radicals, these radicals being, identically or differently, from the above-stated group of the alkyls, and containing 1 to 2 carbon atoms;

trialkylamino: trialkylamino groups with saturated, straight-chain, branched or cyclic alkyl radicals, these radicals being, identically or differently, from the above-stated group of the alkyls, and containing 1 to 2 carbon atoms;

alkylsulfonyl: alkylsulfonyl groups with a saturated, straight-chain, branched or cyclic alkyl radical, this radical being from the above-stated group of the alkyls, and containing 1 to 4 carbon atoms;

alkylaminosulfonyl: alkylaminosulfonyl groups with a saturated, straight-chain, branched or cyclic alkyl radical, this radical being from the above-stated group of the alkyls, and containing 1 to 3 carbon atoms;

alkyloxycarbonyl: alkyloxycarbonyl groups with a saturated, straight-chain, branched or cyclic alkyl radical, this radical being from the above-stated group of the alkyls, and containing 1 to 3 carbon atoms;

alkylcarbonyloxy: alkylcarbonyloxy groups with a saturated, straight-chain, branched or cyclic alkyl radical, this radical being from the above-stated group of the alkyls, and containing 1 to 3 carbon atoms;

alkylaminocarbonyl: alkylaminocarbonyl groups with a saturated, straight-chain, branched or cyclic alkyl radical, this radical being from the above-stated group of the alkyls, and containing 1 to 3 carbon atoms;

alkylcarbonylamino: alkylcarbonylamino groups with a saturated, straight-chain, branched or cyclic alkyl radical, this radical being from the above-stated group of the alkyls, and containing 1 to 3 carbon atoms.

Mono- or polycyclic, aromatic or saturated $C_3$-$C_{14}$ hydrocarbon radical for $D^1$ and $D^3$ denotes, for example:

a) $C_6$-$C_{14}$ aryl, more particularly phenyl, naphth-1-yl, naphth-2-yl, biphen-4-yl, biphen-2-yl, anthracen-9-yl, inden-4-yl, fluoren-2-yl, fluoren-3-yl, fluoren-9-yl and phenanthren-3-yl;

b) $C_3$-$C_8$ cycloalkyl, more particularly cyclopropyl, cyclobutyl, cyclopentyl, cyclohexyl, cycloheptyl, adamantan-1-yl, cuban-1-yl, bicyclo[4.4.0]decan-2-yl and cyclooctyl.

Monocyclic aromatic, partially unsaturated or saturated three- to eight-membered heterocyclic radical for $D^1$ and $D^3$ denotes for example:

a) non-aromatic, saturated or partially unsaturated, 4-, 5- or 6-membered heterocyclyl, containing one to four nitrogen atoms and/or one or two oxygen atoms, more particularly 1-azacyclobut-1-yl, 2-tetrahydrofuranyl, 3-tetrahydrofuranyl, 2-pyrrolidinyl, 3-pyrrolidinyl, 3-isoxazolidinyl, 4-isoxazolidinyl, 5-isoxazolidinyl, 3-pyrazolidinyl, 4-pyrazolidinyl, 5-pyrazolidinyl, 2-oxazolidinyl, 4-oxazolidinyl, 5-oxazolidinyl, 4,5-dihydro-1,3-oxazol-2-yl, 4,5-dihydro-1,3-oxazol-4-yl, 4,5-dihydro-1,3-oxazol-5-yl, 4, 5-dihydro-4H-1,3-oxazin-2-yl, 2-imidazolidinyl, 4-imidazolidinyl, 5-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 4-morpholinyl, 1,3-dioxan-5-yl, 2-tetrahydropyranyl, 4-tetrahydropyranyl, 3-hexahydropyridazinyl, 4-hexahydropyridazinyl, 2-hexahydropyrimidinyl, 4-hexahydropyrimidinyl, 5-hexahydropyrimidinyl, 5H-tetrazol-5-yl, 1H-tetrazol-5-yl, 2H-tetrazol-5-yl, 1-piperazinyl and 2-piperazinyl;

b) 5-membered heteroaryl, containing one to four nitrogen atoms or one to three nitrogen atoms and/or one sulfur or oxygen atom: more particularly 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-isoxazolyl, 4-isooxazolyl, 5-isooxazolyl, 2-thiazolyl, 4-thiazolyl, 5-thiazolyl, 2-isothiazolyl, 4-isothiazolyl, 5-isothiazolyl, 2-imidazolyl, 4-imidazolyl, 1,2,5-thiadiazol-3-yl, 1,2,4-thiadiazol-3-yl, 1,2,4-thiadiazol-5-yl, 1,2,5-oxadiazol-3-yl, 1,2,4-oxadiazol-3-yl, 1,2,4-oxadiazol-5-yl, 1,2, 3-thiadiazol-4-yl, 1,2,3-thiadiazol-5-yl, 1,2,3,4-thiatriazol-5-yl, 1H-(1,2,3)triazol-1-yl, 1H-(1,2,3)triazol-4-yl, 1H-(1,2,3)triazol-5-yl, 1H-(1,3,4)triazol-1-yl and 1H-(1, 3,4)triazol-2-yl;

c) 6-membered heteroaryl, containing one to three nitrogen atoms: more particularly 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The stated linear or cyclic hydrocarbon radicals and heterocycles may be unsubstituted or substituted, the substituents being selected preferably from the group X. Preferred, depending on the respective chain size or ring size, are 1, 2, 3 or 4 substituents; in the case of halogen substituents, preference is also given to substitution up to the maximum possible number (persubstitution).

Advantageous compounds of the formula (I) are those in which all of the symbols have advantageous definitions.

The symbols in the formula (I) preferably have the following definitions:

$A^1$ is preferably a group $D^1$-[$Y^2$-$D^2$-]$_m$-.

$D^1$ is preferably a group phenyl, pyrimidin-5-yl, naphth-1-yl, naphth-2-yl, thien-2-yl, the stated radicals being unsubstituted or substituted one or more times by a group X.

$D^2$ is preferably a group phenylene-1,4-diyl, pyridine-2,5-diyl, pyrimidine-2,5-diyl or thiophene-2,5-diyl, the stated radicals being unsubstituted or substituted one or more times by a group X.

$Y^1$ is preferably ~C(O)— or ~CH$_2$C(O)—, where ~ denotes the bond to the group $A^1$.

$Y^2$ is preferably a bond.

$A^2$ is preferably
  a) a group —OS(O)$_2$OL or
  b) a group —NH—W.

W is preferably
  a) a group ~SO$_3$L or
  b) a group $D^3$-$Y^3$—.

$Y^3$ is preferably a bond or a group ~CH$_2$OC(O)—, ~OC(O)—, ~S(O)$_2$—, ~C(O)— or ~CH$_2$—C(O)—, where ~ denotes the bond to the group $D^3$.

$D^3$ is preferably a group methyl, ethyl, prop-2-yl, pent-5-yl, cyclopropyl, 1,1-dimethylethyl, phenyl, thien-2-yl, furan-2-yl, imidazolidin-5-yl, pyrazin-5-yl, naphthalen-1-yl.

$A^3$ is preferably a group pentan-1-yl or hexan-1-yl.

X is preferably identically or differently fluoro, chloro, hydroxyl, carboxyl, methyl, trifluoromethyl, methoxy, dimethylamino or oxo (=O).

m is preferably 0 or 1.

Z is preferably ~O—.

$R^1$ is preferably C(O)OM.

$R^2$ is preferably H.

$R^3$ is preferably H or OH.

$R^4$ is preferably NHC(O)CH$_3$.

$R^5$, $R^6$ are preferably identically or differently OH or OC(O)CH$_3$.

L is preferably a cation.

M is preferably methyl, ethyl or a cation.

Preferred compounds of the formula (I) are those in which all of the symbols have the preferred definitions.

Further-preferred sialic acid derivatives of the formula (I) are those of the formulae (Ia)-(Ih), where the symbols have the definitions and preferences indicated in the formula (I).

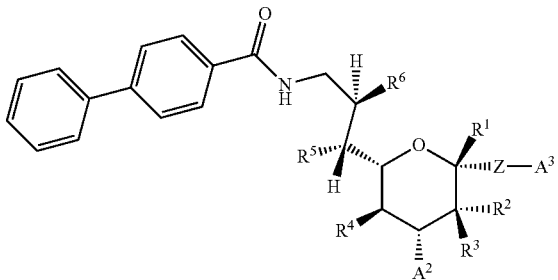

Ia

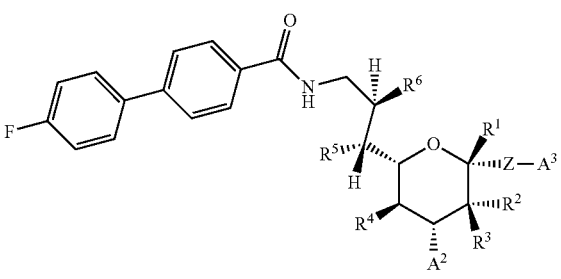

Ib

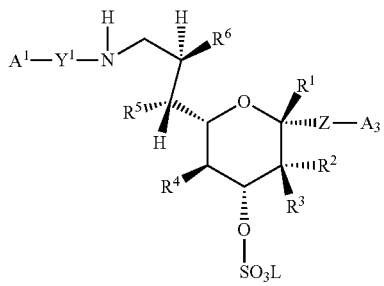

Ic

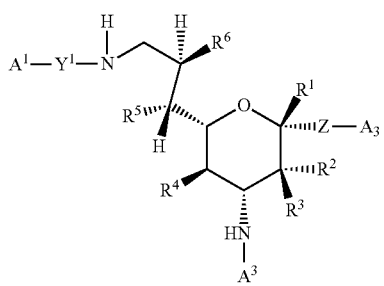

Id

Ie
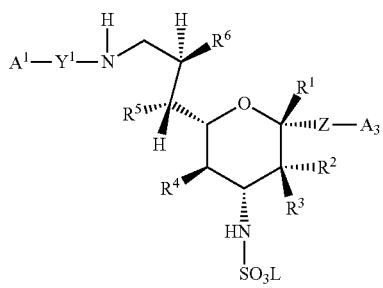
If
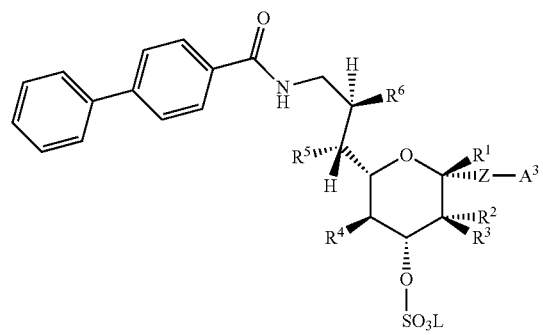
Ig
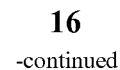
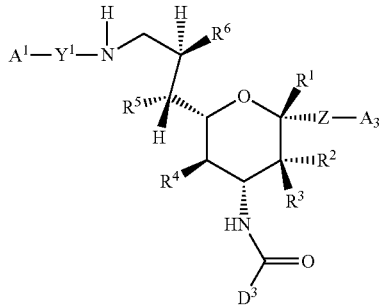
Ih
Particularly preferred, moreover, are sialic acid derivatives of the formulae (Iaa)-(Iam), where the symbols have the definitions indicated in the formula (I):
Iaa
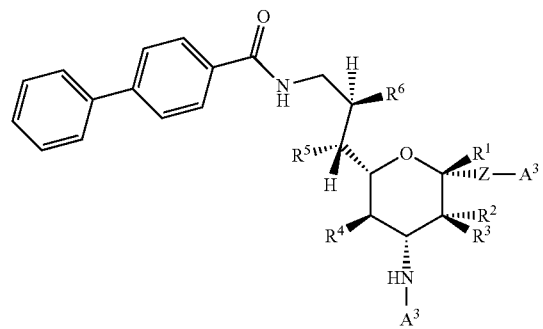
Iab
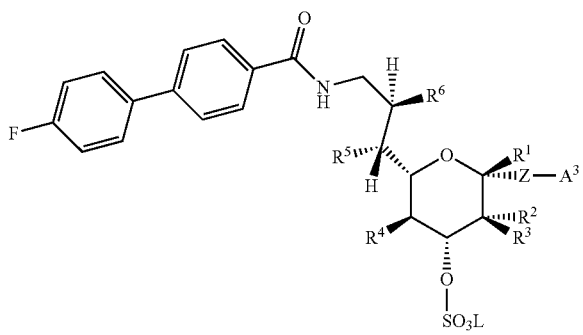
Iac
Iad
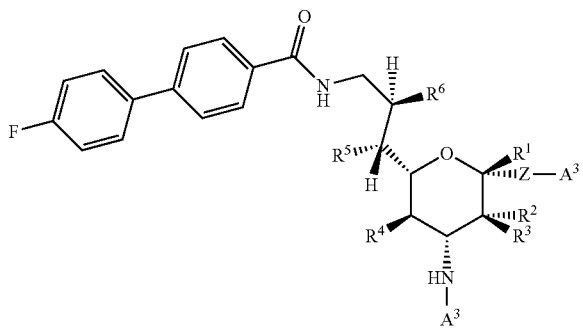

-continued
| | |
|---|---|
| Iae 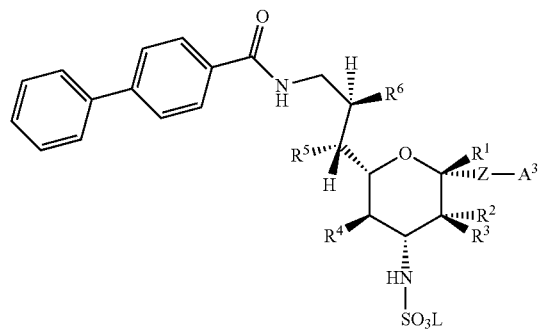 | Iaf 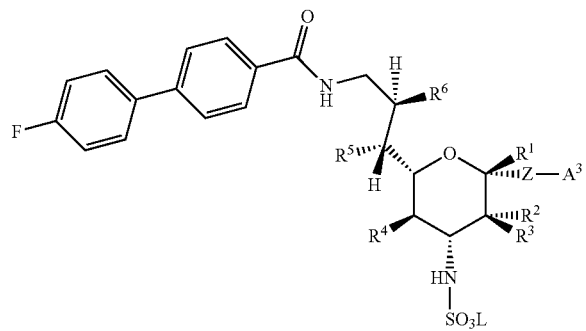 |
| Iag 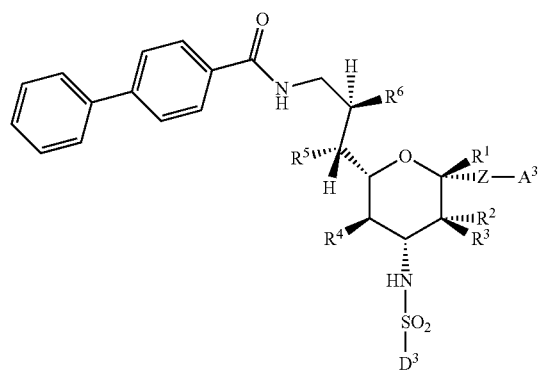 | Iai 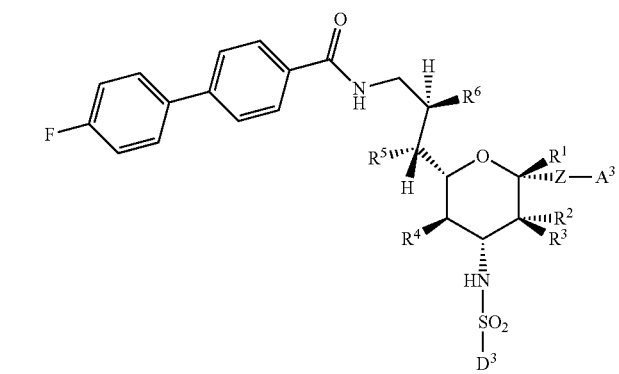 |
| Iaj 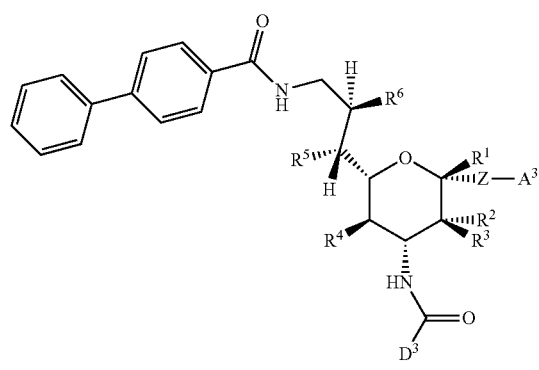 | Iak 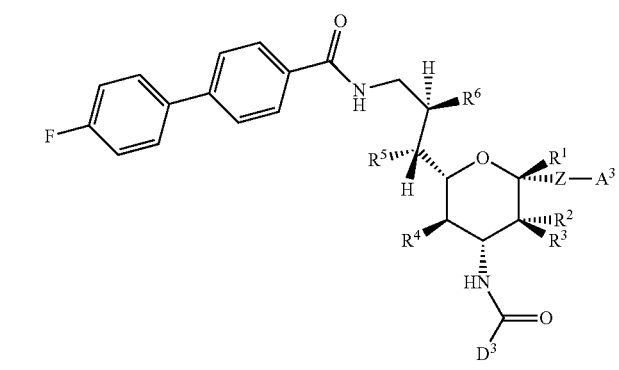 |
Ial
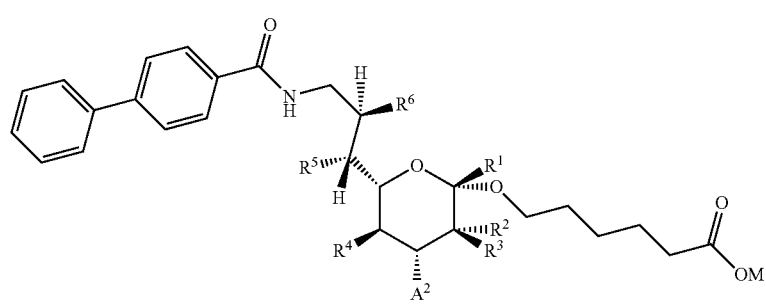

Iam
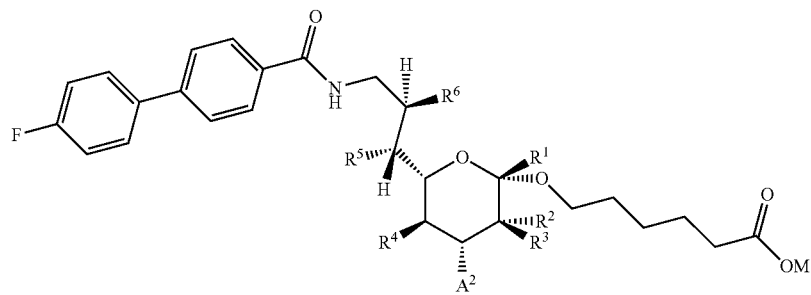
Especially preferred are sialic acid derivatives of the formulae (Iba)-(Ibj), where the symbols have the definitions indicated in the formula (I):
Iba
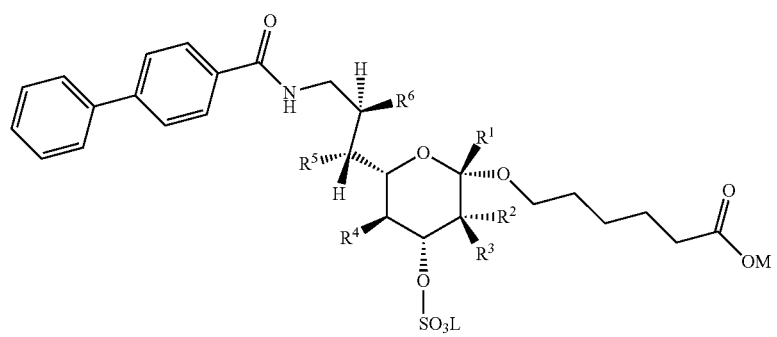
Ibb
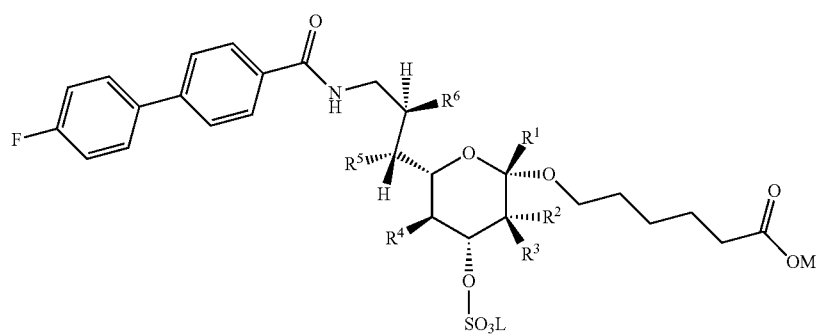
Ibc
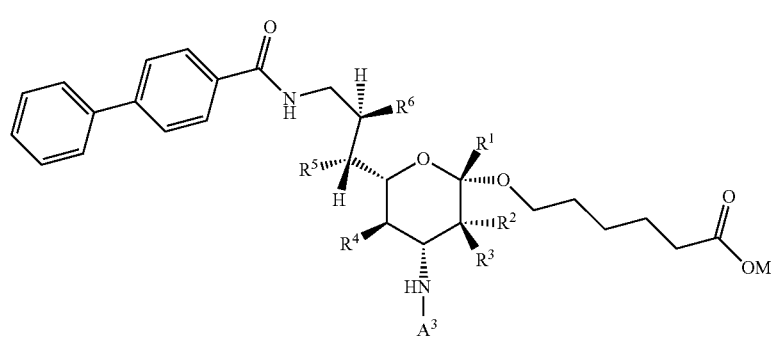

Ibd
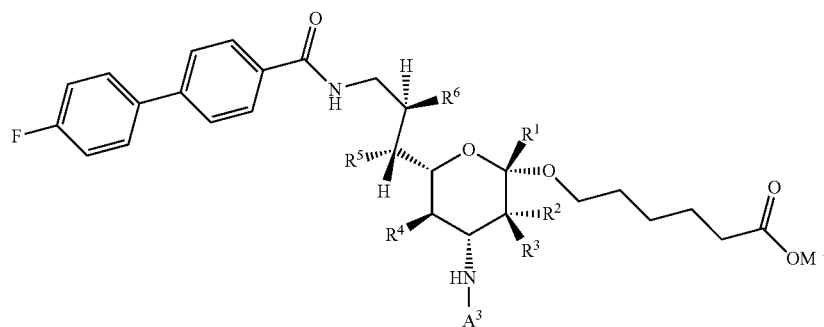
Ibe
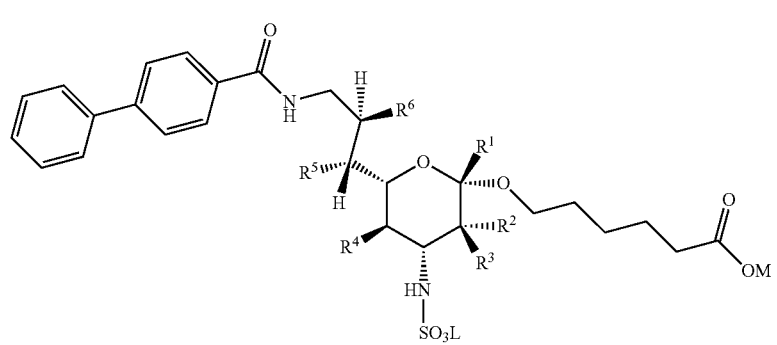
Ibf
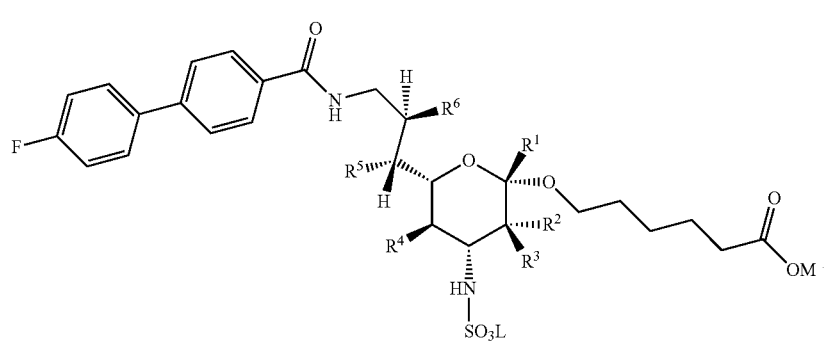
Ibg
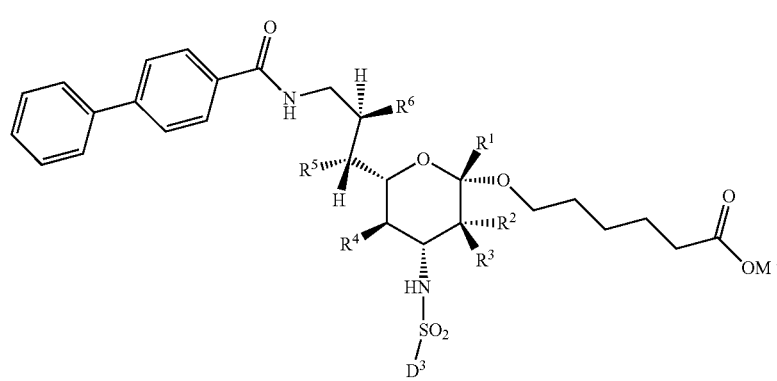

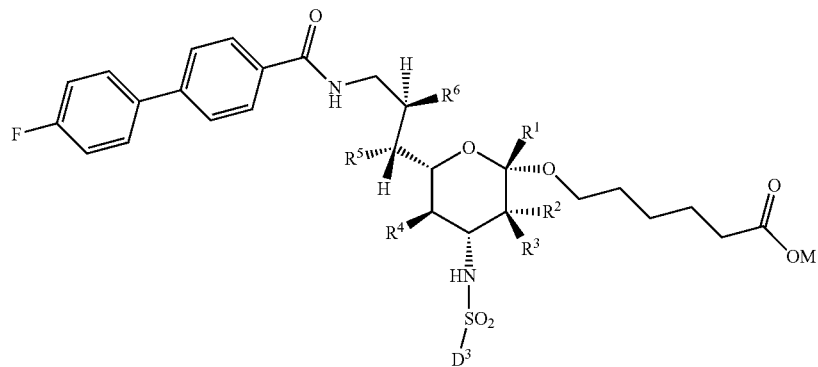
Ibh
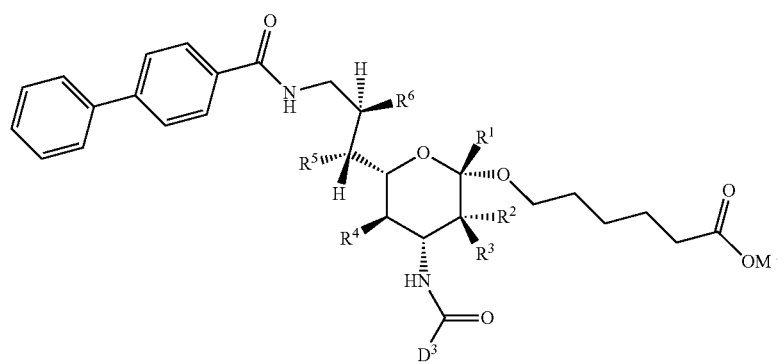
Ibi
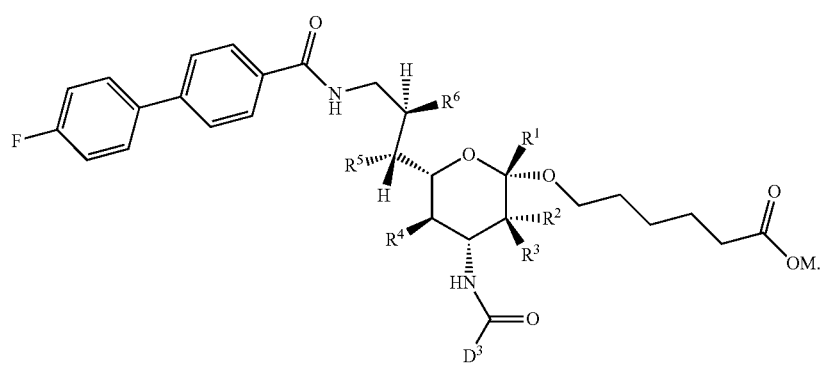
Ibj
Strongly preferred are sialic acid derivatives of the formulae (Ica)-(Icj), where the symbols have the definitions indicated in the formula (I):
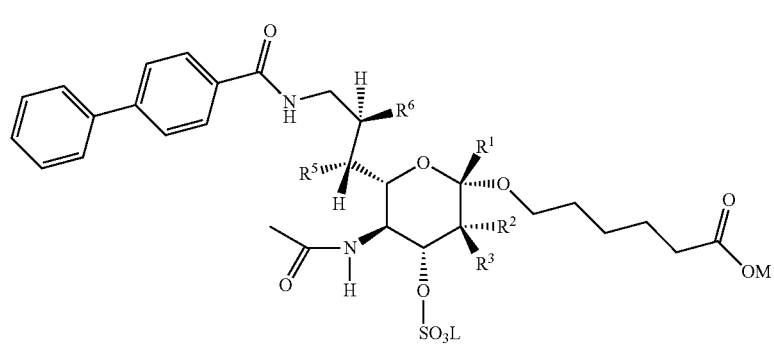
Iba -continued
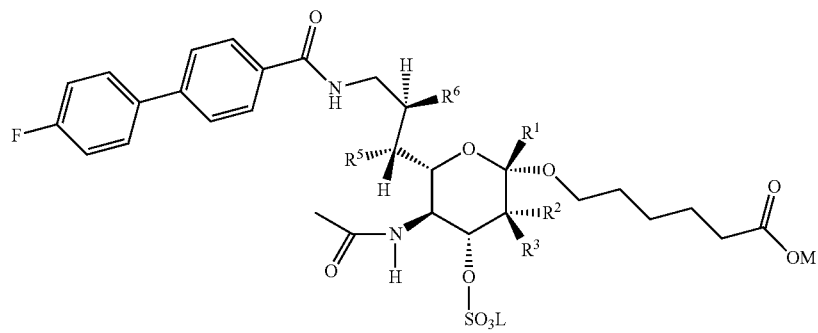
Ibb
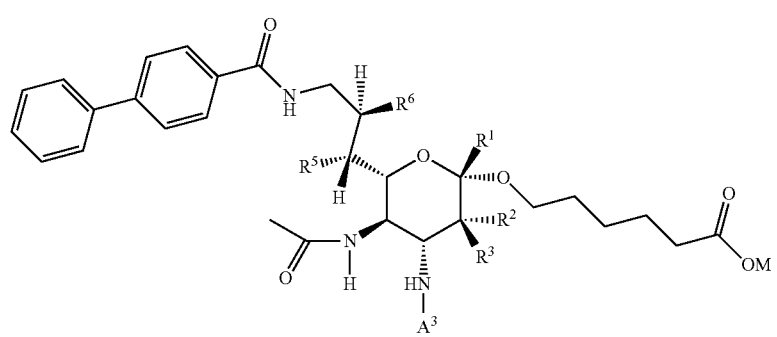
Ibc
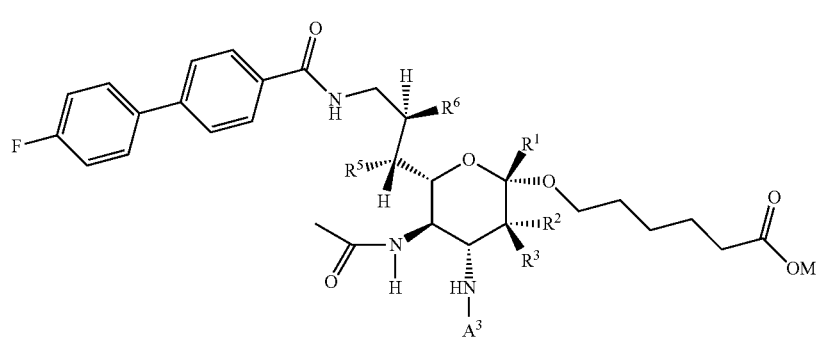
Ibd
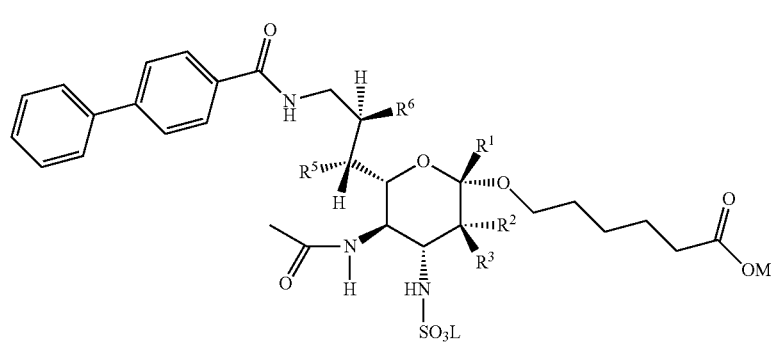
Ibe

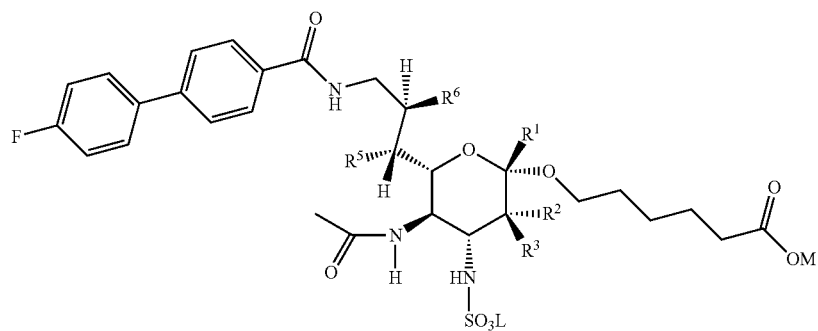
Ibf
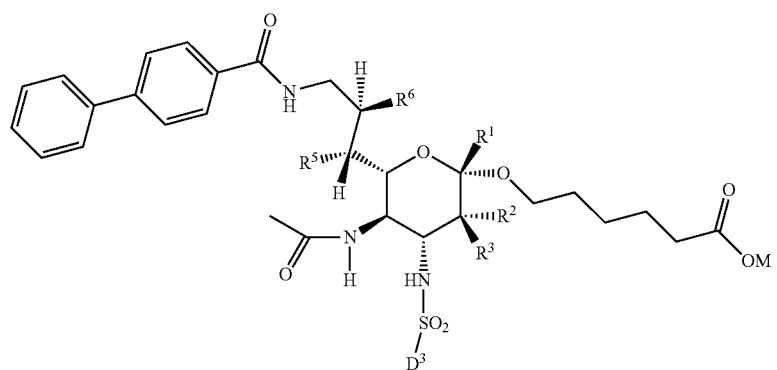
Ibg
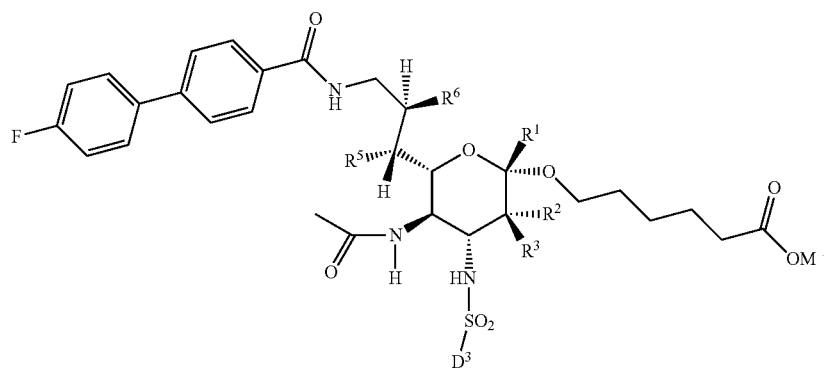
Ibh
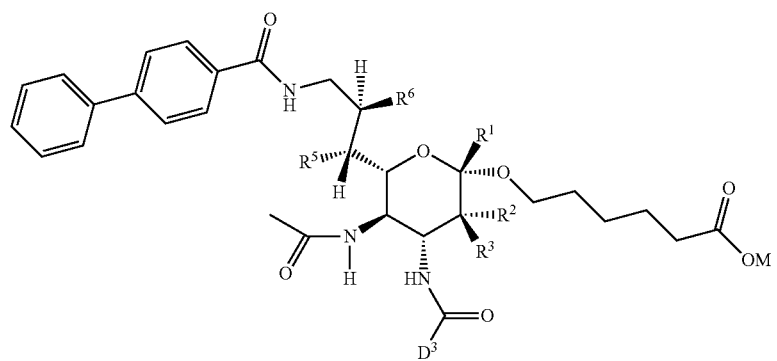
Ibi

Ibj

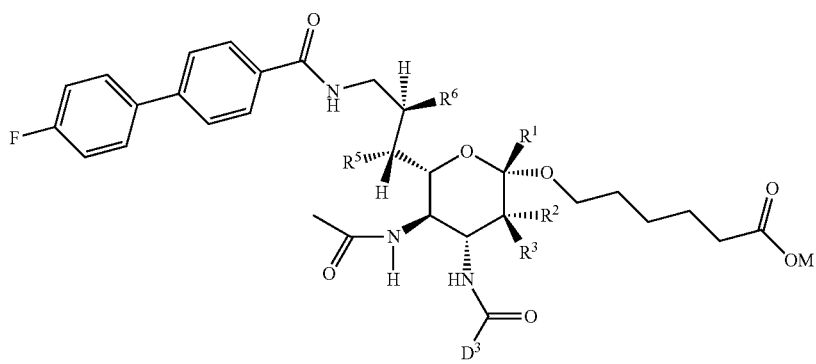

The sialic acid derivatives (I) of the invention are obtainable employing synthesis processes that are known in principle. The compounds are preferably obtained by the preparation processes of the invention which are elucidated in more detail below, especially by synthesis schemes I-VII:

Intermediates for the preparation of sialic acid derivatives of the formula (I) may be prepared, for example, by synthesis schemes I to IV.

Scheme I

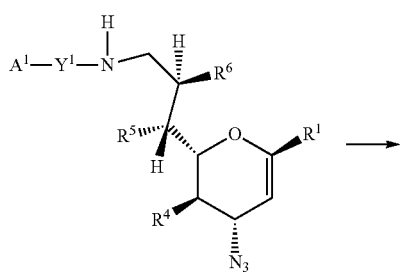

II

Compounds of the formula (III) may be prepared, for example, by addition of hydrogen chloride onto the double bond in compound (II). By way of example, compound 5 was prepared.

Scheme II

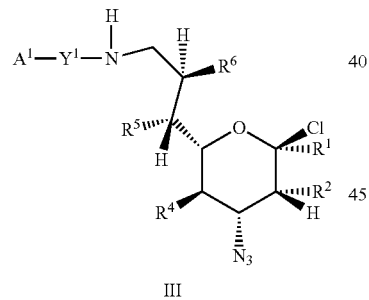

III

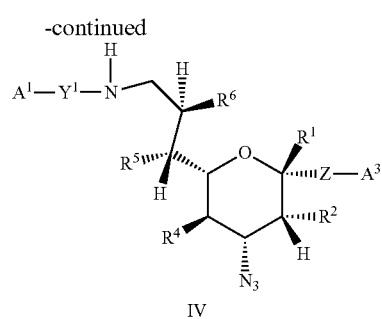

IV

Compounds of the formula (IV) may be prepared, for example, by replacing the chlorine atom in compound (III) by the group $Z^1$-$A^3$. By way of example, compound 13 was prepared.

Scheme III

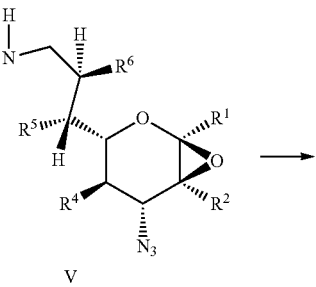

V

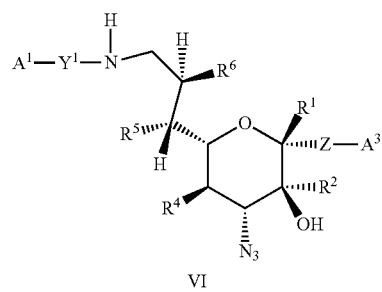

VI

Compounds of the formula (VI) may be prepared, for example, by opening the epoxide in compound (V) by means of the group $Z^1$-$A^3$. By way of example, compound 8 was prepared.

Scheme IV

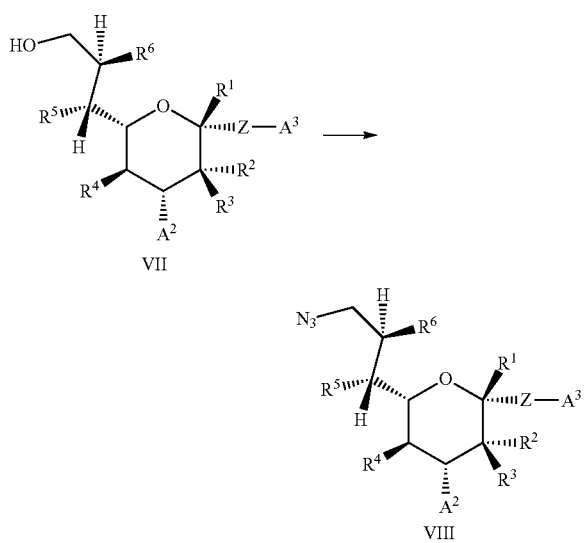

Compounds of the formula (VIII) may be prepared, for example, by replacing the hydroxyl group in compound (VII) with an azide. By way of example, compound 34 was prepared.

Sialic acid derivatives of the formula (I) may be prepared, for example, by synthesis schemes V to VII.

Scheme V

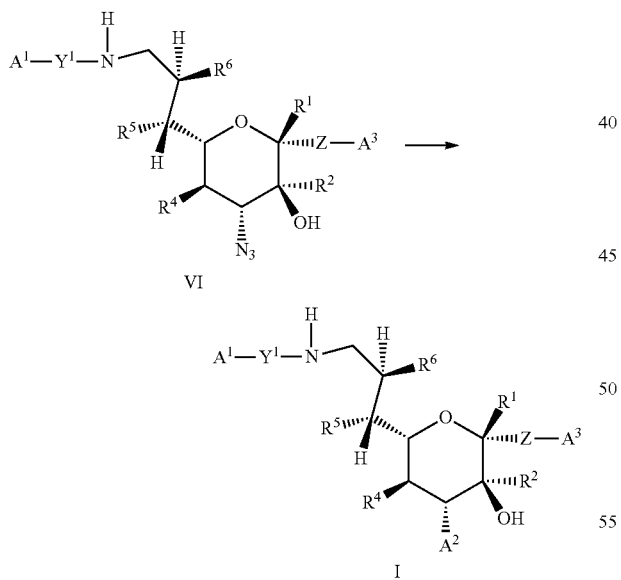

Compounds of the sialic acid derivatives of the formula (I) may be prepared, for example, by reducing the azide in compounds of the formula (VI) and subsequently reacting the resultant amine with a carboxylic acid or a sulfonyl chloride. Any protecting groups present may be removed by known methods. By way of example, compounds 10, 11, 38, 39, 40, 41, 42, 43, 44, 45, 46, 47, 48, 49, 50, 51, 52 and 65 were prepared.

Scheme VI

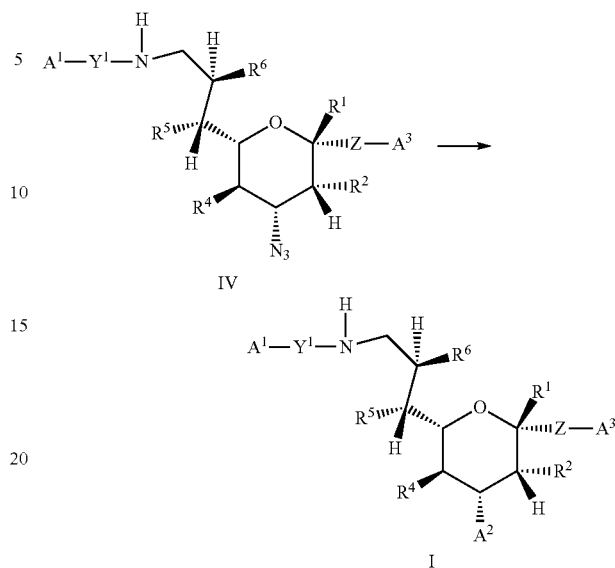

Compounds of the sialic acid derivatives of the formula (I) may be prepared, for example, by reducing the azide in compounds of the formula (IV) and subsequently reacting the resultant amine with an activated carboxylic acid, a sulfonyl chloride or a sulfating agent. Any protecting groups present may be removed by methods that are common knowledge. By way of example, compounds 15, 16, 17, 18, 53, 54, 55, 56, 57, 58, 59, 60, 61, 62, 63 and 64 were prepared.

Scheme VII

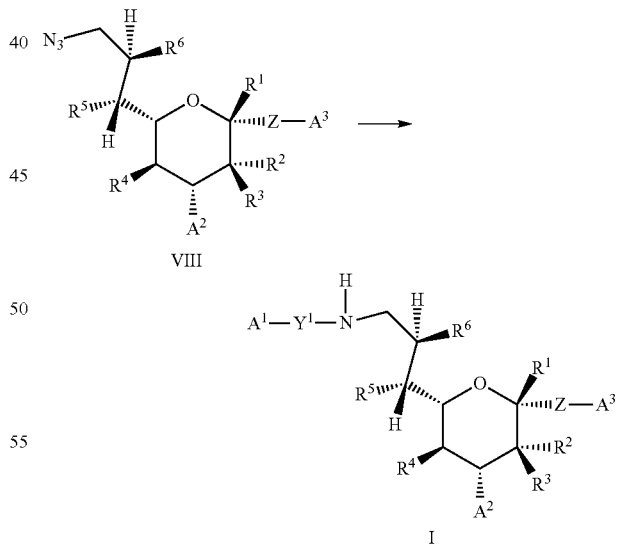

Compounds of the formula (I) may be prepared, for example, by reducing the azide in compounds of the formula (VIII) and subsequently reacting the resultant amine with an activated carboxylic acid, a sulfonyl chloride or a sulfating agent. Any protecting groups present may be removed by methods that are common knowledge. By way of example, compound 36 was prepared.

The sialic acid derivatives of the formula (I) are suitable as pharmacologically active compounds and active ingredients for medicament preparations. They act as Siglec ligands, more particularly as Siglec-2 (CD22) ligands, for the regulation of the immune system, more particularly as an auxiliary in vaccinations, and also for the treatment of diseases whose course or activity can be influenced by the Siglec ligands, more particularly allergies, autoimmune disorders, chronic inflammations, paraplegia, multiple sclerosis, cancer, viral disorders, for example AIDS, and also in bacterial diseases, for example streptococci, parasitic disorders, for example Chagas disease, diseases in which the immune response is disrupted in the context of B cell activation, such as Common Variable Immunodeficiency (CVID) and IgA deficiency, in diseases of the hematopoietic organs and of the blood, and also in cancer, for example lymphomas and myelomas. Preferred indications are allergies, autoimmune disorders and CVID.

Treatment in the sense of the invention denotes a therapeutic treatment, both for curing and also for the alleviation of symptoms, and also a preventive treatment.

The sialic acid derivatives may be used in combination with other pharmacologically active substances, more particularly those which boost the activity of the compounds of the invention.

The invention also provides a method for treating a Siglec-mediated disease, more particularly from the group of allergies, autoimmune disorders, chronic inflammations, paraplegia, multiple sclerosis, cancer, viral disorders, for examples AIDS, diseases in which the immune response is disrupted in the context of B cell activation, such as Common Variable Immunodeficiency (CVID) and IgA deficiency, by administering to a person affected by the disease a preferably therapeutically effective amount of a sialic acid derivative of the formula (I).

Further provided by the invention is a sialic acid derivative of the formula (I) or a pharmacologically tolerated salt thereof as medicament, more particularly for the treatment of Siglec-mediated diseases, such as those described above.

The invention provides, furthermore, a sialic acid derivative of the formula (I) or a pharmacologically tolerated salt thereof for use in a method for treating Siglec-mediated diseases, more particularly those described above.

Additionally provided by the invention is a sialic acid derivative of the formula (I) for use in the production of a medicament for the treatment of Siglec-mediated diseases, more particularly those described above.

Likewise provided by the invention is a pharmaceutical preparation (i.e. medicament) comprising at least one sialic acid derivative of the formula (I), or a pharmacologically tolerated salt thereof, and a pharmacologically tolerated carrier.

The dose that is necessary to achieve a corresponding activity in treatment or prophylaxis is commonly dependent on the compound to be administered, the patient, the nature and severity of the disease or condition, and the nature and frequency of administration, and is within the discretion of the physician to be treated. In the case of intravenous administration, the dose may appropriately be in the range from 0.1 to 1000 mg, preferably 0.5 to 500 mg, and for oral administration in the range from 1 to 1000 mg, preferably 10 to 500 mg, in each case one or more times daily. For this purpose, the compounds of the formula (I) according to the invention, optionally in combination with other active substances, may be processed together with one or more inert customary excipients and/or diluents, as for example with corn starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into customary pharmaceutical preparations such as tablets, film tablets, capsules, powders, solutions, suspensions or suppositories.

The sialic acid derivatives (I) of the invention may be administered by any conventional method, including orally and parenterally, by means of intravenous, subcutaneous or intramuscular injections, for example.

The sialic acid derivatives (I) may also be used for purposes other than those specified, for example as diagnostic agents, as for example in methods for determining the activity of Siglec ligands, as biochemical probes, or as intermediates for the preparation of further compounds, more particularly of pharmacologically active compounds.

The invention is illustrated, but not restricted, by the examples.

EXAMPLES

A. Synthesis examples are represented in Schemes 1 to 18.

Scheme 1

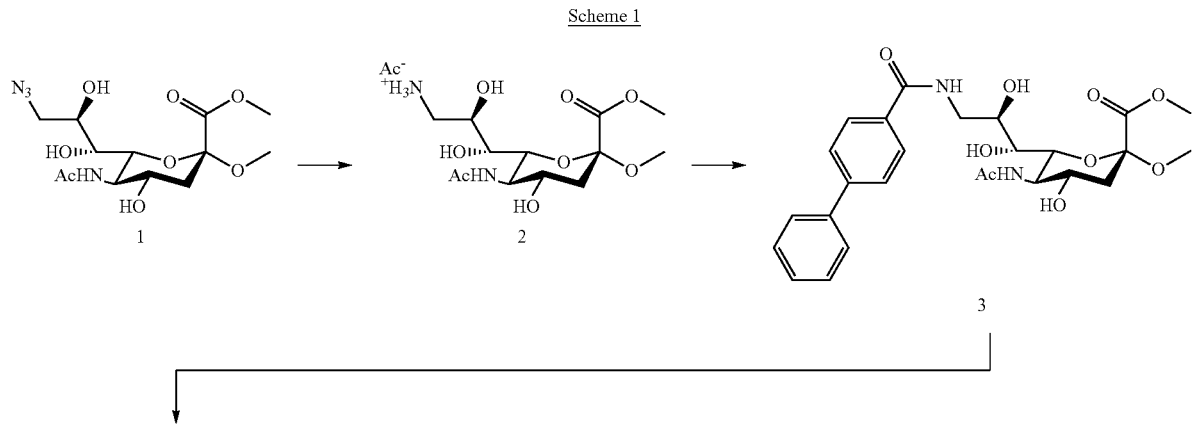

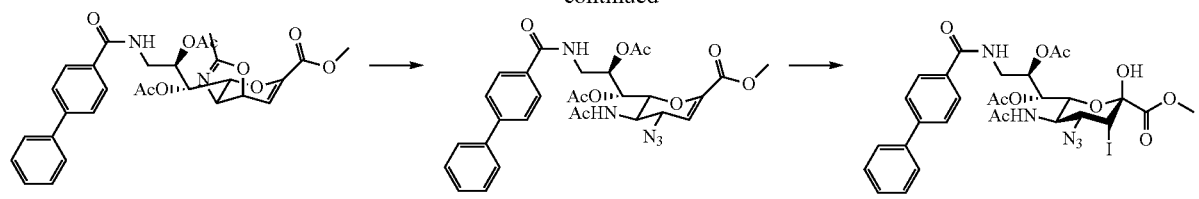
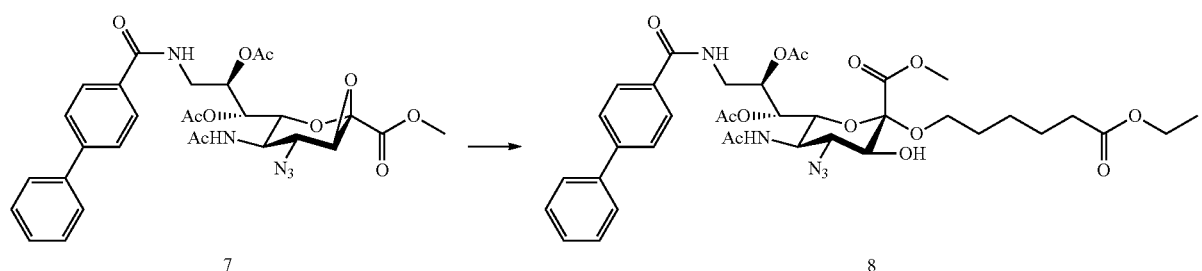
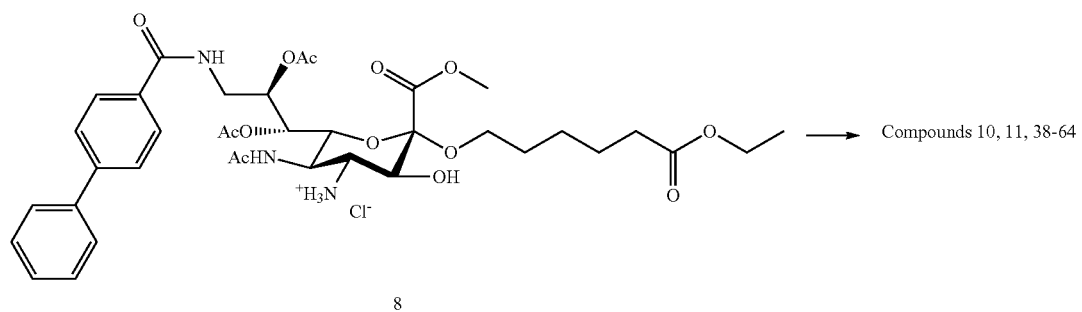
Scheme 2
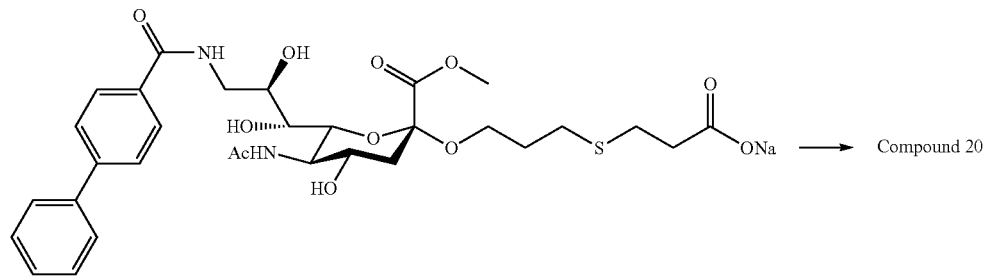

Scheme 3
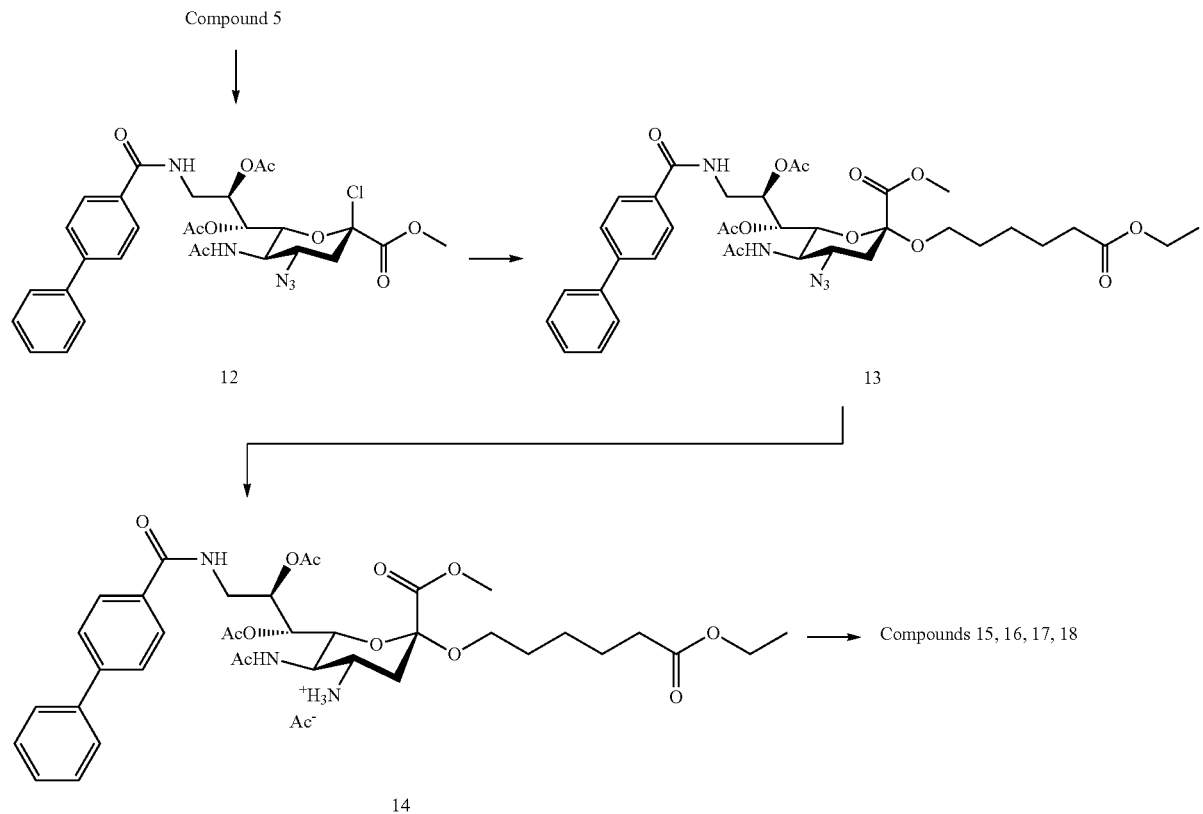
Scheme 4
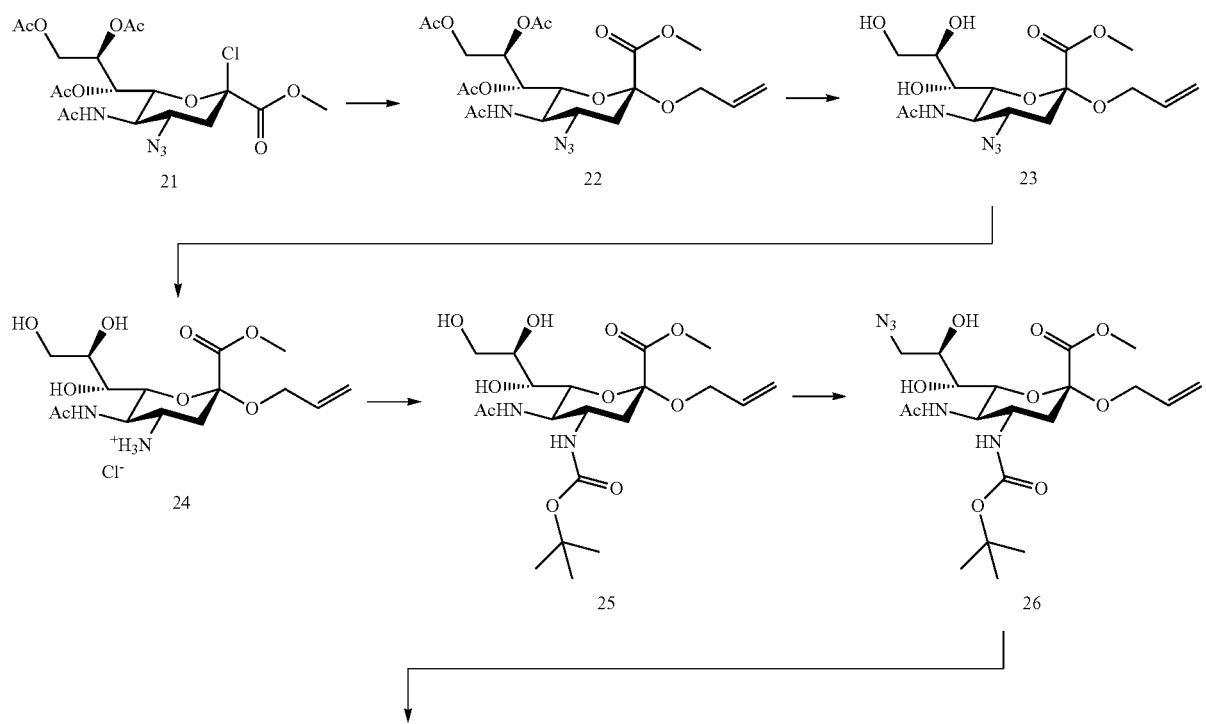

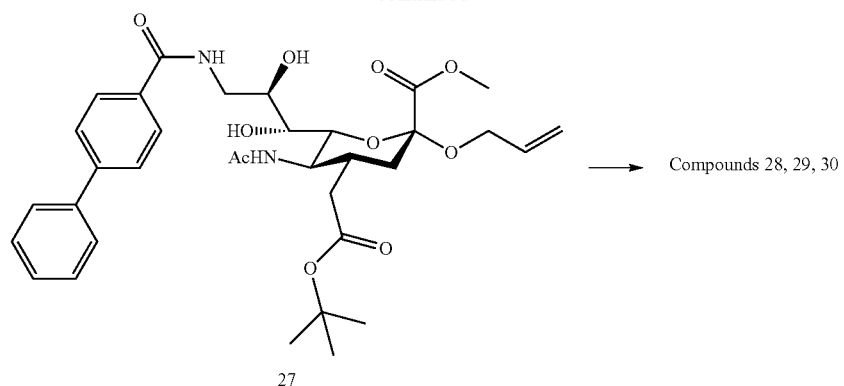
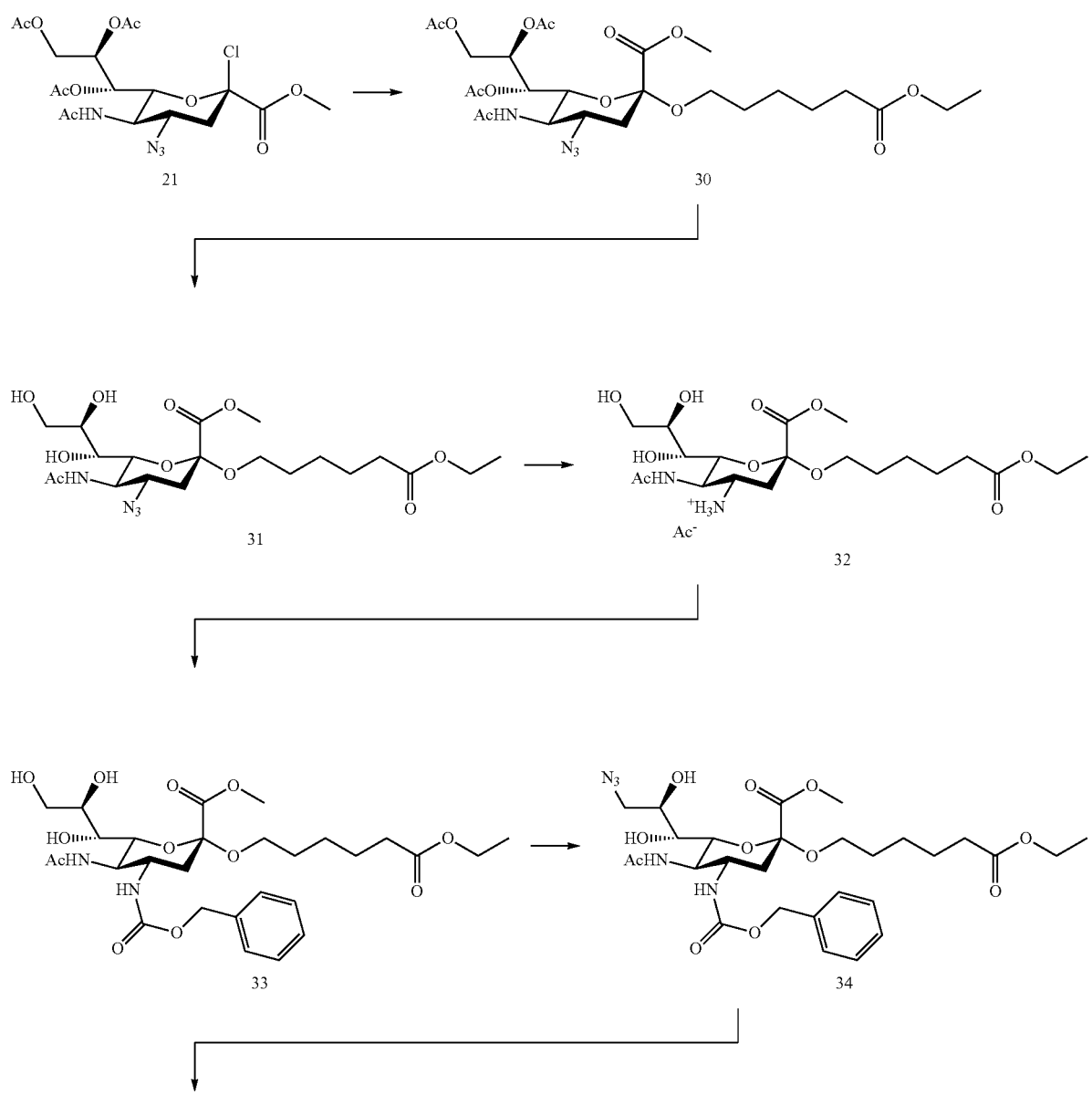
Scheme 5

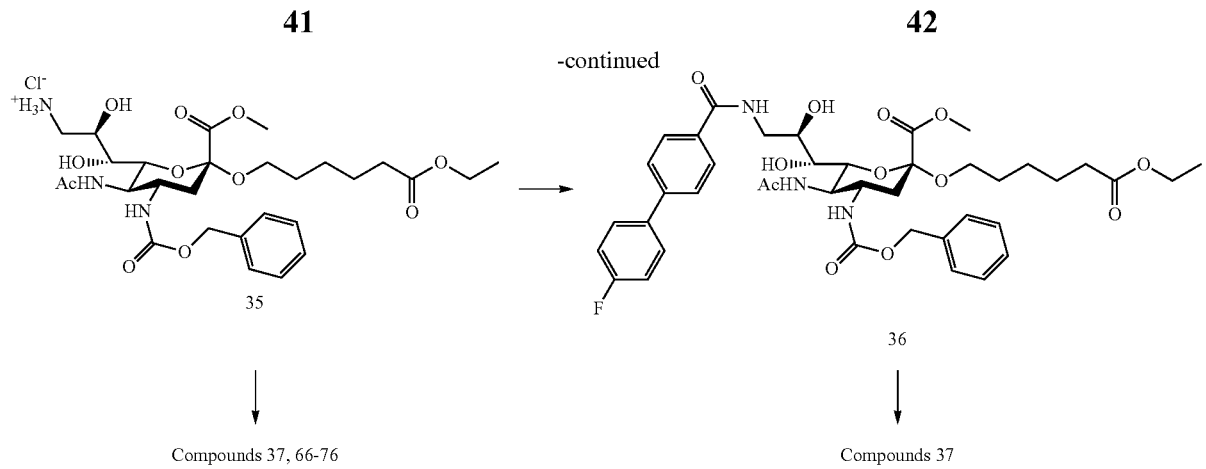

Compounds 37, 66-76 | Compounds 37

The compounds were obtained as described below:

All of the compounds used but not described were purchased or prepared by known literature protocols.

For purifications with silica gel, silica gel Si60 43-60 mm was used. Around 100 g of silica gel were utilized per gram of substance. Indicated in parentheses is the eluent. For purifications on RP-18 silica gel (YMC CO LTD., YMC ODS-AQ), the gel was suspended in methanol, introduced into a column, prewashed with water, and the substance was applied as a solution or suspension with water. The column volume was about 5 cm in height and about 1 cm in diameter. The solvent was forced through the column at low pressure, generated by a hand-operated pressure ball. The eluent used was a gradient from water to ethanol, unless otherwise indicated.

Solvents were removed by means of a vacuum rotary evaporator under reduced pressure with a bath temperature of 40° C. In the syntheses hereinafter, this workstep is identified as "concentration".

All of the substances were lyophilized from water or a water/dioxane mixture.

The reactions and substances were monitored by thin-layer chromatography. This was done using aluminum plates coated with silica gel, with a fluorescence indicator (Merck TLC Silica gel 60 $F_{254}$). Substance detection took place under UV light at 366 and 254 nm. The chromatograms were subsequently sprayed with dilute sulfuric acid and heated in order to visualize the substances. For their detection, amines were visualized by spraying with ninhydrin solution and heating. Details and further visualization methods are elucidated in "Anfärbereagenzien für Dünnschicht- and Papierchromatographie" Merck, 1970. Spectroscopic data were recorded using Bruker ApexQe hybrid 9.4 T FT-ICR (ESI) and Varian 500 MHz or 300 MHz system (NMR) instruments.

ABBREVIATIONS

DMF N,N-dimethylformamide
DIPEA N,N-diisopropylethylamine
EtOH ethanol
HAc acetic acid
HATU O-(7-azabenzotriazol-1-yl)-N,N,N',N'-tetramethyluronium
MeOH methanol
TEA triethylamine
Compound 1
  prepared according to: Tetrahedron Letters, 1994, 50 (25), 7445-7460

Compound 2
  A solution of 2.2 g of compound 1 in 100 ml of MeOH was admixed with 4.45 g of triphenylphosphine and 6 ml of $H_2O$ and the suspension was stirred at room temperature for 18 h. With stirring, 20 ml of 20% strength acetic acid and 90 ml of $H_2O$ were added, the mixture was stirred for half an hour, the suspension was concentrated to 100 ml, and the concentrate was extracted with three times 100 ml of dichloromethane. The aqueous phase was lyophilized. Yield: 2.67 g of solid Compound 3
  A solution of 2.0 g of compound 2 in 20 ml of DMF was mixed with 1.69 g of 4-nitrophenyl 4-biphenylcarboxylate and 2.09 ml of TEA and stirred for 17 h. The solution was concentrated and the residue was purified on a silica gel column ($CHCl_3$:MeOH gradient). Yield: 3.2 g Compound 4
  A solution of 2.2 g of compound 3 in 20 ml of acetic acid and 20 ml of acetic anhydride was admixed at 0° C. with 2 ml of concentrated sulfuric acid and stirred at 25° C. for 48 h. The acetic acid was removed on a rotary evaporator and the remaining solution was added slowly dropwise to 1000 ml of saturated sodium hydrogencarbonate solution. The suspension was stirred for 4 h and extracted with three times 200 ml of ethyl acetate. The combined organic phases were washed with saturated NaCl solution, dried ($MgSO_4$), filtered and concentrated. The residue was purified on a silica gel column ($CH_2Cl_2$:MeOH gradient). Yield: 2.0 g Compound 5
  A solution of 1.25 g of compound 4 and 1.19 ml of trimethylsilyl azide in 20 ml of dry tert-butanol was stirred at 80° C. for 4 h. The solution was concentrated and the residue was used further without further purification.

Compound 6
  A solution of 1350 mg of compound 5 in 0.8 ml of acetonitrile and 2 ml of water was mixed at 60° C. with 538 mg of N-iodosuccinimide, stirred for 30 min and concentrated. The residue was purified on a silica gel column ($CHCl_3$ to MeOH). Yield: 1170 mg.

Compound 7
  A solution of 1140 mg of compound 6 in 10 ml of dry acetonitrile was mixed with 0.277 ml of 1,8-diazabicyclo[5.4.0]undec-7-ene, stirred for 15 min and concentrated. The residue was purified on a silica gel column ($CHCl_3$ to MeOH). Yield: 750 mg Compound 8
  A solution of 20 mg of camphorsulfonic acid in 0.5 ml of ethyl 6-hydroxyhexanoate was mixed with 150 mg of compound 7, stirred for 20 min and diluted with 30 ml of CH$_2$Cl$_2$. The excess of ethyl 6-hydroxyhexanoate was removed on a silica gel column (CH$_2$Cl$_2$:MeOH 100:1). The product was eluted from the column (CH$_2$Cl$_2$:MeOH 10:1) and purified on RP18. Yield: 50 mg Compound 9

A solution of 50 mg of compound 8 in 5 ml of MeOH was mixed with 0.05 ml of H$_2$O and 51 mg of triphenylphosphine and stirred for 17 h. The solution was admixed with 0.5 ml of acetic acid (20%) and 10 ml of H$_2$O, and the suspension was purified on RP18 (H$_2$O, then dilute HCl pH3, then H$_2$O to EtOH gradient). Yield: 40 mg Compounds 10

A solution of 15 mg of compound 9 in 0.5 ml of DMF was admixed with 33 ml of DIPEA and 5.0 ml of propanoic anhydride, stirred for 15 min, diluted with 2 ml of H$_2$O, admixed with 0.1 ml of 2M NaOH and stirred for 2 h. The solution was adjusted to pH 8-9 with 20% acetic acid, admixed with 0.5 ml of saturated Na$_2$CO$_3$ solution and purified on RP18. Yield: 9 mg; $^1$H NMR (500 MHz, CD$_3$OD): d ppm 7.94 (d, J=8.63 Hz, 2H), 7.73 (d, J=8.38 Hz, 2H), 7.68 (dd, J=8.19, 1.17 Hz, 1H), 7.47 (t, J=7.66 Hz, 2H), 7.38 (t, J=7.39 Hz, 1H), 4.08 (ddd, J=8.41, 7.81, 3.14 Hz, 1H), 4.03 (dd, J=10.86, 10.03 Hz, 1H), 3.98 (t, J=10.27 Hz, 1H), 3.85 (td, J=9.04, 6.85 Hz, 1H), 3.81 (dd, J=9.97, 1.89 Hz, 1H), 3.78 (dd, J=13.59, 3.02 Hz, 1H), 3.59 (dd, J=13.88, 7.80 Hz, 1H), 3.55 (td, J=9.19, 7.08 Hz, 1H), 3.50 (d, J=10.24 Hz, 1H), 3.43 (dd, J=9.00, 2.00 Hz, 1H), 2.22 (q, J=7.63 Hz, 2H), 2.17 (dd, J=8.24, 7.03 Hz, 2H), 1.90 (s, 3H), 1.66-1.57 (m, 4H), 1.44-1.35 (m, 2H), 1.13 (t, J=7.65 Hz, 3H); HRMS (ESI-neg) calculated for C31H41N3O12 [M-2Na+H]$^-$: 672.2774, found: 672.2801.

Compound 11

A solution of 24 mg of compound 9 in 1 ml of CH$_2$Cl$_2$ was admixed with 21 µl of TEA and 3.6 µl of methanesulfonyl chloride and stirred for 15 min. The solution was admixed with 2 ml of saturated NaHCO$_3$ solution, stirred for 15 min, admixed with 20 ml of CH$_2$Cl$_2$ and 20 ml of saturated NaHCO$_3$. The organic phase was dried (MgSO$_4$), filtered and purified on RP18. The residue was dissolved in a little EtOH. The solution was admixed with water until turbidity appeared, adjusted with 2M NaOH to pH 12-13, stirred for 2 h, neutralized with dilute acetic acid and concentrated. The residue was dissolved with a little water, admixed with 0.3 ml of saturated NaHCO$_3$ and purified on RP18. Yield: 11 mg; $^1$H NMR (500 MHz, CD$_3$OD): δ ppm 7.94 (d, J=8.68 Hz, 2H), 7.73 (d, J=8.70 Hz, 2H), 7.68 (dd, J=8.41, 1.23 Hz, 2H), 7.47 (t, J=7.62 Hz, 2H), 7.38 (t, J=7.39 Hz, 1H), 4.08 (ddd, J=9.06, 7.59, 3.21 Hz, 1H), 3.87 (t, J=10.48 Hz, 1H), 3.85 (td, J=9.22, 6.53 Hz, 1H), 3.77 (dd, J=13.73, 3.14 Hz, 1H), 3.75 (dd, J=10.49, 2.06 Hz, 1H), 3.59 (dd, J=13.75, 7.59 Hz, 1H), 3.54 (td, J=9.08, 6.72 Hz, 1H), 3.47 (d, J=10.44 Hz, 1H), 3.44 (dd, J=8.99, 1.98 Hz, 1H), 3.34 (t, J=10.45 Hz, 1H), 3.05 (s, 3H), 2.16 (dd, J=8.22, 7.14 Hz, 2H), 1.98 (s, 3H), 1.66-1.57 (m, 4H), 1.45-1.35 (m, 2H); HRMS (ESI-neg) calculated for C31H39N3O13S [M-2Na+H]$^-$: 694.2287, found: 694.2302.

Compounds 12

A solution of 70 mg of compound 5 in 10 ml of acetyl chloride was admixed at 0° C. with 0.5 g of LiCl, and 0.5 ml of HCl (37%) was added dropwise over the course of 1 h. The solution was stirred at 0° C. for 5 h and admixed with LiCl to saturation point. The suspension was stirred at RT for 5 days, and every 20 h it was cooled to 0° C., 0.1 ml of HCl (37%) was added dropwise and then the suspension was stirred at 0° C. for 4 h. The suspension was concentrated, the residue was admixed with CH$_2$Cl$_2$, the suspension was washed with cold NaHCO$_3$ solution and with saturated NaCl solution, dried (MgSO$_4$), filtered and concentrated. The residue was used directly without storage.

Compound 13

A mixture of 2 ml of CH$_2$Cl$_2$, 2 ml of ethyl 6-hydroxyhexanoate and 0.5 g of dry molecular sieve A4 was mixed with 50 mg of compound 12 and stirred for 5 days. CH$_2$Cl$_2$ was removed under reduced pressure, the suspension was stirred at 40° C. for 1 h and diluted with CH$_2$Cl$_2$. Ethyl 6-hydroxyhexanoate was removed on a silica gel column (CH$_2$Cl$_2$:MeOH 100:1), and the products were eluted from the column (CH$_2$Cl$_2$:MeOH 5:1) and concentrated. The residue was purified on RP18. Yield: 20 mg Compound 14

A solution of 20 mg of compound 13 in 5 ml of MeOH and 0.2 ml of HAc (20%) was admixed with a catalytic amount of Pd-on-carbon and hydrogenated for 60 min. The suspension was filtered over Celite, concentrated and lyophilized. Yield: 16 mg Compound 15

A solution of 16 mg of compound 14 in 1 ml of DMF was admixed with 13 mg of sulfur trioxide-pyridine (1:1) and 58 µl of TEA, stirred for 20 min, admixed with MeOH and stirred for a further 20 min. The excess TEA was removed under reduced pressure and the solution was diluted with water, adjusted to pH 8 with saturated NaHCO$_3$ and purified on RP18. The product was dissolved with a little EtOH, and the solution was diluted with water until turbidity occurred, adjusted to a pH of 13 using 2M NaOH, stirred for 2 h, diluted with 10 ml of water, adjusted to a pH of 8 with dilute acetic acid, and purified on RP18. Yield: 4 mg; $^1$H NMR (500 MHz, CD$_3$OD): δ ppm 7.94 (d, J=8.45 Hz, 2H), 7.73 (d, J=8.53 Hz, 2H), 7.68 (dd, J=8.33, 1.11 Hz, 2H), 7.47 (t, J=7.68 Hz, 2H), 7.38 (t, J=7.39 Hz, 1H), 4.08 (ddd, J=8.82, 7.94, 3.21 Hz, 1H), 3.79 (td, J=9.10, 6.96 Hz, 1H), 3.78 (dd, J=13.54, 3.23 Hz, 1H), 3.71 (dd, J=10.22, 1.90 Hz, 1H), 3.61 (t, J=10.20 Hz, 1H), 3.58 (dd, J=13.66, 7.75 Hz, 1H), 3.47 (td, J=9.05, 7.02 Hz, 1H), 3.45 (dd, J=9.05, 1.94 Hz, 1H), 3.39 (ddd, J=12.12, 10.61, 4.41 Hz, 1H), 3.07 (dd, J=12.68, 4.54 Hz, 1H), 2.16-2.12 (m, 2H), 2.01 (s, 3H), 1.65-1.52 (m, 5H), 1.40-1.32 (m, 2H); HRMS (ESI-neg) calculated for C30H36N3Na3O13S [M-3Na+2H]$^-$: 680.2131, found: 680.2153.

Compound 16

A solution of 65 mg of compound 14 in 1 ml of DMF was admixed with 12 µl of propanoic anhydride and 35 µl of TEA, stirred for 1 h and concentrated. The residue was purified on RP18. Yield: 60 mg; $^1$H NMR (500 MHz, CD$_3$OD): δ ppm 7.89 (d, J=8.55 Hz, 2H), 7.65 (d, J=8.56 Hz, 2H), 7.60 (dd, J=8.30, 1.22 Hz, 2H), 7.45 (t, J=7.54 Hz, 2H), 7.38 (t, J=7.36 Hz, 1H), 7.10 (dd, J=8.03, 4.48 Hz, 1H), 5.76 (d, J=8.03 Hz, 1H), 5.69 (d, J=9.33 Hz, 1H), 5.31 (td, J=9.69, 3.31 Hz, 1H), 5.22 (dd, J=9.73, 2.13 Hz, 1H), 4.29 (ddd, J=15.04, 8.20, 3.13 Hz, 1H), 4.10 (q, J=7.13 Hz, 2H), 4.10 (dd, J=10.08, 2.24 Hz), 3.99-3.88 (m, 2H), 3.78 (td, J=9.39, 6.28 Hz, 1H), 3.77 (s, 3H), 3.21 (td, J=9.41, 6.39 Hz, 1H), 3.06 (td, J=15.07, 4.12 Hz, 1H), 2.57 (dd, J=12.82, 3.58 Hz, 1H), 2.29 (t, J=7.73 Hz, 2H), 2.22 (s, 3H), 2.13 (s, 3H), 1.89 (s, 3H), 1.72 (t, J=12.64 Hz, 1H), 1.67-1.60 (m, 2H), 1.58-1.52 (m, 2H), 1.44-1.32 (m, 2H), 1.24 (t, J=7.14 Hz, 3H), 1.09 (t, J=7.60 Hz, 3H); HRMS (ESI-pos) calculated for C40H53N3O13 [M+Na]$^+$: 806.3471, found: 806.3492.

Compound 17

A solution of 30 mg of compound 16 in a little EtOH was admixed with water until turbidity occurred, adjusted to a pH of 12-13 using 2M NaOH, and maintained at said pH for 2 h. The solution was diluted with 10 ml of water, adjusted to a pH of 8-9 using dilute acetic acid and purified on RP18.

Yield: 24 mg; $^1$H NMR (500 MHz, CD$_3$OD): δ ppm 7.94 (d, J=8.61 Hz, 2H), 7.72 (dd, J=8.69, 1.85 Hz, 2H), 7.67 (dd, J=6.95, 1.46 Hz, 2H), 7.46 (t, J=7.61 Hz, 2H), 7.38 (t, J=7.39 Hz, 1H), 4.11-4.02 (m, 2H), 3.84-3.76 (m, 4H), 3.60 (dd, J=13.57, 7.35 Hz, 1H), 3.51-3.44 (m, 2H), 2.67 (dd, J=12.43, 4.40 Hz, 1H), 2.20-2.12 (m, 4H), 1.91 (s, 3H), 1.66 (t, J=12.56 Hz, 1H), 1.64-1.53 (m, 4H), 1.41-1.33 (m, 2H), 1.11 (t, J=7.66 Hz, 3H); HRMS (ESI-neg) calculated for C33H41N3Na2O11[M-2Na+H]$^-$: 656.2825, found: 656.2815.

Compound 18

A solution of 20 mg of compound 14 in 1 ml of DMF was admixed with 5 mg of succinic anhydride and 21 μl of TEA, stirred for 30 min and concentrated. The residue was purified on RP18. Yield: 17 mg; $^1$H NMR (300 MHz, CD$_3$OD): δ ppm 7.84 (d, J=8.36 Hz, 2H), 7.71 (d, J=8.26 Hz, 2H), 7.65 (d, J=7.46 Hz, 2H), 7.46 (t, J=7.45 Hz, 2H), 7.37 (t, J=7.27 Hz, 1H), 5.44 (ddd, J=9.36, 6.87, 2.61 Hz, 1H), 5.26 (dd, J=9.25, 2.13 Hz, 1H), 4.20 (dd, J=10.13, 1.95 Hz, 1H), 4.09 (q, J=7.11 Hz, 2H), 3.95-3.73 (m, 7H), 3.37 (dd, J=14.53, 6.89 Hz, 1H), 3.23 (td, J=9.56, 6.28 Hz, 1H), 2.44 (dd, J=13.07, 2.97 Hz, 1H), 2.29 (t, J=7.39 Hz, 2H), 2.17 (s, 2H), 2.12 (s, 2H), 1.85 (s, 3H), 1.75 (t, J=12.75 Hz, 1H), 1.67-1.47 (m, 4H), 1.45-1.30 (m, 4H), 1.22 (t, J=7.12 Hz, 3H); HRMS (ESI-neg) calculated for C41H52N3NaO15 [M-Na]$^-$: 826.3404, found: 826.3381.

Compound 20

A solution of 25 mg of compound 19 (WO 2013097942) in water was adjusted to a pH of 13 using 2M NaOH, held at that pH for 2 h, adjusted to a pH of 8 using dilute HAc and purified on RP18. The lyophilized product (20 mg) was dissolved in 0.5 ml of DMF and admixed in portions with sulfur trioxide-pyridine (1:1) until only about 20% of reactant was detectable in the TLC. MeOH was added, stirring took place for 30 min, and the MeOH was removed under reduced pressure. The solution was diluted with water, adjusted to a pH of 8 using NaHCO$_3$ solution and purified on RP18. Yield: 5 mg (21%)$^1$H NMR (500 MHz, CD$_3$OD): δ ppm 7.94 (d, J=8.63 Hz, 2H), 7.73 (d, J=8.62 Hz, 2H), 7.68 (dd, J=8.38, 1.21 Hz, 2H), 7.47 (t, J=7.66 Hz, 2H), 7.38 (t, J=7.40 Hz, 1H), 4.46 (ddd, J=11.61, 9.99, 5.15 Hz, 1H), 4.09 (ddd, J=8.84, 7.74, 3.27 Hz, 1H), 3.87 (td, J=9.47, 6.40 Hz, 1H), 3.81 (t, J=10.23 Hz, 1H), 3.79 (dd, J=13.65, 3.28 Hz, 1H), 3.73 (dd, J=10.44, 1.89 Hz, 1H), 3.58 (dd, J=13.68, 7.55 Hz, 1H), 3.58 (td, J=9.49, 6.34 Hz, 1H), 3.46 (dd, J=8.96, 1.86 Hz, 1H), 3.19 (dd, J=12.26, 5.10 Hz, 1H), 2.73 (dd, J=8.03, 7.62 Hz, 2H), 2.59 (dt, J=7.14, 5.04 Hz, 1H), 2.40 (dd, J=8.02, 7.60 Hz, 2H), 2.00 (s, 3H), 1.85-1.79 (m, 2H), 1.71 (t, J=12.00 Hz, 1H); HRMS (ESI-neg) calculated for C30H35N2Na3O14S2 [M-3Na+2H]$^-$: 713.1692, found: 713.1715.

Compound 22

Compound 21 (3500 mg) was dissolved in 20 ml of dry allyl alcohol, admixed with 5 g of ground molecular sieve A4 and stirred for 5 h. The suspension was concentrated at 40° C. and the residue was admixed with CH$_2$Cl$_2$, filtered over Celite and purified on a silica gel column (CH$_2$Cl$_2$ to MeOH). The isolated product was recrystallized from ethyl acetate/diethyl ether. Yield: 1600 mg Compound 23

A solution of 1600 mg of compound 22 in 20 ml of dry MeOH was admixed with 1 ml of 1M sodium methoxide. Following complete reaction, the solution was neutralized with ion exchange resin (Dowex H+form) in MeOH. The resin was removed by filtration and the solution was concentrated. Yield: 1200 mg Compound 24

A solution of 1200 mg of compound 23 in 20 ml of MeOH and 4 ml of water was admixed with 2010 mg of zinc powder and 1670 mg of ammonium chloride and stirred for 5 h. The suspension was filtered over Celite, concentrated and used further directly. Yield: 1200 mg Compound 25

A solution of 1200 mg of compound 24 in 20 ml of MeOH was admixed with 721 mg of Boc anhydride and 0.49 ml of TEA, stirred for 2 h and concentrated. The residue was purified on silica gel (ethyl acetate). Yield: 976 mg Compound 26

Compound 25 (976 mg) was dissolved three times in 10 ml of dry DMF and concentrated under reduced pressure. The anhydrous residue was dissolved in 10 ml of dry DMF and admixed at 0° C. with 517 mg of dry lithium azide, 1678 mg of tetrabromomethane and 664 mg of triphenylphosphine. The solution was stirred at 25° C. for 16 h, admixed with 5 ml of MeOH and concentrated. The residue was admixed with water and extracted twice with ethyl acetate. The combined organic phases were washed with saturated NaCl, dried (MgSO$_4$), filtered and purified on a silica gel column (ethyl acetate). Yield: 700 mg Compound 27

A solution of 700 mg of compound 26 in 50 ml of DMF was admixed with 0.5 ml of water, 1130 mg of triphenylphosphine and 1375 mg of 4-nitrophenyl 4-biphenylcarboxylate, stirred for three days, concentrated and purified on a silica gel column (CH$_2$Cl$_2$ to MeOH). Yield: 440 mg Compound 28

A solution of 30 mg of compound 27 in 5 ml of MeOH and 2 ml of water was flushed with nitrogen for 20 min, admixed with 41 μl of thiopropionic acid and a catalytic amount of azaisobutyronitrile, and irradiated with UV light for 12 h. The solution was concentrated and the residue was purified on RP18. Yield: 30 mg; $^1$H NMR (500 MHz, CD$_3$OD): δ ppm 7.93 (d, J=8.62 Hz, 2H), 7.71 (d, J=8.65 Hz, 2H), 7.66 (dd, J=8.38, 1.21 Hz, 2H), 7.45 (t, J=7.62 Hz, 2H), 7.37 (t, J=7.39 Hz, 1H), 4.05 (ddd, J=8.87, 7.28, 3.21 Hz, 1H), 3.91-3.82 (m, 6H), 3.80 (dd, J=13.83, 3.23 Hz, 1H), 3.67-3.62 (m, 1H), 3.60 (dd, J=13.78, 7.35 Hz, 1H), 3.49 (td, J=9.37, 6.42 Hz, 1H), 3.45 (dd, J=8.83, 1.25 Hz, 1H), 2.71 (dd, J=8.46, 7.06 Hz, 2H), 2.62-2.51 (m, 3H), 2.39 (dd, J=8.56, 6.84 Hz, 2H), 1.90 (s, 3H), 1.82-1.70 (m, 3H), 1.42 (s, 9H); HRMS (ESI-neg) calculated for C36H48N3NaO12S [M-Na]$^-$: 746.2964, found: 746.2928.

Compound 29

A solution of 30 mg of compound 28 in a little MeOH was admixed with water until turbidity occurred, adjusted to a pH of 13 using 2M NaOH, stirred at the pH for 2 h, adjusted to a pH of 8-9 using dilute acetic acid, and purified on RP18. Yield: 25 mg; $^1$H NMR (500 MHz, CD$_3$OD): δ ppm 7.93 (d, J=8.61 Hz, 2H), 7.71 (d, J=8.63 Hz, 2H), 7.66 (dd, J=8.37, 1.19 Hz, 2H), 7.45 (t, J=7.63 Hz, 2H), 7.36 (t, J=7.39 Hz, 1H), 4.06 (ddd, J=8.96, 7.60, 3.17 Hz, 1H), 3.87 (td, J=9.48, 6.39 Hz, 1H), 3.80-3.66 (m, 4H), 3.57 (dd, J=13.22, 6.98 Hz, 1H), 3.54 (td, J=9.48, 6.25 Hz, 1H), 3.44 (dd, J=8.99, 1.24 Hz, 1H), 2.72 (dd, J=8.51, 6.99 Hz, 12H), 2.68 (dd, J=12.56, 3.65 Hz, 1H), 2.63-2.52 (m, 2H), 2.40 (dd, J=8.51, 7.12 Hz, 2H), 1.92 (s, 3H), 1.83-1.76 (m, 2H), 1.61 (t, J=12.16 Hz, 1H), 1.42 (s, 9H); HRMS (ESI-neg) calculated for C36H45N3Na2O12S [M-2Na+H]$^-$: 732.2808, found: 732.2763.

Compound 30

A solution of 3500 mg of compound 21 in 4 ml of CH$_2$Cl$_2$ was stirred together with 1.9 ml of ethyl 6-hydroxyhexanoate and 5 g of dry molecular sieve A4, and CH$_2$Cl$_2$ was removed on a rotary evaporator. The suspension was stirred at 40° C. for 6 h, diluted with CH$_2$Cl$_2$ and filtered over Celite. Ethyl 6-hydroxyhexanoate was removed on a silica gel column (CH$_2$Cl$_2$:MeOH 100:1). The products were eluted from the column with (CH$_2$Cl$_2$:MeOH 5:1) and again purified on silica gel (CH$_2$Cl$_2$ to MeOH). Yield 2300 mg of unclean product, which was used further without additional purification.

Compound 31

A solution of 2300 mg of compound 30 in 20 ml of dry MeOH was admixed with fresh sodium methoxide in MeOH until pH indicator paper indicated a pH of 8-9. After 1 h the solution was neutralized with ion exchange resin (Dowex H+form) in MeOH. The resin was removed by filtration, the solution was concentrated and the residue was purified on a silica gel column (CH$_2$Cl$_2$ to MeOH). The fractions containing product were purified on RP18. Yield: 374 mg Compound 32

A solution of 370 mg of compound 31 in 10 ml of MeOH was admixed with 0.5 ml of acetic acid (20%) and a catalytic amount of Pd-on-carbon and hydrogenated for 2 h. The suspension was filtered over Celite, the solution was concentrated and the residue was lyophilized. Yield: 395 mg Compound 33

A solution of 395 mg of compound 32 in 10 ml of DMF was admixed with 142 mg of benzyloxycarbonyl chloride and 0.31 ml of TEA, stirred for 2 h and concentrated. The residue was purified on a silica gel column (CH$_2$Cl$_2$ to MeOH). Yield: 245 mg Compound 34

Compound 33 (245 mg) was dissolved three times in 10 ml of dry DMF and concentrated under reduced pressure. The anhydrous residue was dissolved in 10 ml of dry DMF and admixed at 0° C. with 100 mg of dry lithium azide, 325 mg of tetrabromomethane and 139 mg of triphenylphosphine. The solution was stirred at 25° C. for 16 h, admixed with 5 ml of MeOH and concentrated. The residue was admixed with water and was extracted twice with toluene and twice with ethyl acetate. The combined ethyl acetate phases were dried (MgSO$_4$), filtered and purified on RP18. Yield: 176 mg Compound 35

A solution of 175 mg of compound 34 in 10 ml of MeOH and 2 ml of water was admixed with 182 mg of zinc powder and 151 mg of ammonium chloride and stirred for 2 h. The suspension was filtered over Celite, concentrated and used further directly. Yield: 270 mg Compound 36

A solution of 55 mg of compound 35 and 28 mg of 4-(4-fluorophenyl)benzoic acid in 0.5 ml of DMF was admixed with 49 mg of O-(7-azabenzotriazol-1-yl)-N,N,N', N'-tetramethyluronium and 0.146 ml of DIPEA. The solution was stirred for 10 min and concentrated and the residue was purified over RP18. Yield 40 mg Compound 37

A solution of 40 mg of compound 36 in 5 ml of MeOH and 0.5 ml of HAc (20%) was admixed with a catalytic amount of Pd-on-carbon and hydrogenated for 60 min. The suspension was filtered over Celite, concentrated and lyophilized. The residue (30 mg) was dissolved in 2 ml of DMF and admixed with 20 mg of sulfur trioxide-pyridine (1:1) and 59 μl of TEA. The solution was stirred for 60 min, admixed with 5 ml of water and 0.5 ml of 2M NaOH and stirred for a further 40 min, neutralized with HAc and concentrated. The residue was dissolved in water, admixed with 1 ml of saturated Na$_2$CO$_3$ and purified on RP18. Yield: 8 mg; $^1$H NMR (500 MHz, CD$_3$OD): δ ppm 7.92 (d, J=8.54 Hz, 2H), 7.71-7.67 (m, 4H), 7.19 (t, J=8.84 Hz, 2H), 4.06 (ddd, J=9.19, 8.27, 3.20 Hz, 1H), 3.80-3.73 (m, 2H), 3.69 (dd, J=10.20, 1.94 Hz, 1H), 3.60 (dd, J=10.84, 9.69 Hz, 1H), 3.56 (dd, J=13.66, 7.80 Hz, 1H), 3.46 (td, J=8.94, 6.86 Hz, 1H), 3.43 (dd, J=8.96, 1.93 Hz, 1H), 3.37 (ddd, J=12.25, 10.61, 4.49 Hz, 1H), 3.05 (dd, J=12.71, 4.53 Hz, 1H), 2.13 (dd, J=8.02, 7.36 Hz, 2H), 2.00 (s, 3H), 1.62-1.51 (m, 5H), 1.38-1.31 (m, 2H); HRMS (ESI-neg) calculated for C30H35FN3Na3O13S [M-2Na+H]$^-$: 720.1889, found: 720.1856.

Compounds 38, 39, 40, 41, 42

General procedure: A solution of 0.20 mg of compound 9 in 50 μl of DMF was admixed with a 25-fold excess of the corresponding anhydride and 100-fold excess of DIPEA. The solution was stirred at 20° C. for 10 min. The reaction was monitored by thin-layer chromatography and was quantitative for all the experiments. The solution was diluted with 500 μl of water, admixed with 50 μl of 2M NaOH and, after 2 h, was admixed with 50 μl of HAc (20%) and lyophilized. Following the addition of acetic acid, the reaction was monitored by thin-layer chromatography and was quantitative for all the experiments.

Compounds 43, 44, 45, 46, 47, 48, 49, 50, 51, 52, 53, 54, 55, 56, 57, 58, 59, 60, 61, 62, 63, 64

General procedure: A solution of 0.20 mg of compound 9 in 50 μl of DMF was admixed with a 25-fold excess of the corresponding carboxylic acid, a 15-fold excess of HATU and 100-fold excess of DIPEA and the solution was stirred at 20° C. for 10 min. The reaction was monitored by thin-layer chromatography and was quantitative for all the experiments. The solution was diluted with 500 μl of water, admixed with 50 μl of 2M NaOH and, after 2 h, was admixed with 50 μl of HAc (20%) and lyophilized. Following the addition of acetic acid, the reaction was monitored by thin-layer chromatography and was quantitative for all the experiments.

Compounds 65

A solution of 0.20 mg of compound 9 in 50 μl of DMF was admixed with a 25-fold excess of dansyl chloride and 100-fold excess of DIPEA and the solution was stirred at 20° C. for 10 min. The reaction was monitored by thin-layer chromatography and was quantitative. The solution was diluted with 500 μl of water, admixed with 50 μl of 2M NaOH and, after 2 h, was admixed with 50 μl of HAc (20%) and lyophilized. Following the addition of acetic acid, the reaction was monitored by thin-layer chromatography and was quantitative.

Compounds 66, 67, 68, 69, 70, 71, 72, 73, 74, 75, 76

General procedure: A solution of 0.20 mg of compound 35 in 50 μl of DMF was admixed with a 25-fold excess of the corresponding carboxylic acid, a 15-fold excess of HATU and 100-fold excess of DIPEA and the solution was stirred at 20° C. for 10 min. The reactions were monitored by thin-layer chromatography and was quantitative for all the experiments. The solution was diluted with 500 μl of water, admixed with 50 μl of 2M NaOH and, after 2 h, was admixed with 50 μl of HAc (20%) and lyophilized. Following the addition of acetic acid, the reaction was monitored by thin-layer chromatography and was quantitative for all the experiments.

Compound 77

A solution of 40 mg of compound 27 in 5 ml of MeOH and 2 ml of water was flushed with nitrogen for 20 min, admixed with 705 mg of cysteamine hydrochloride and a catalytic amount of azaisobutyronitrile, and irradiated with UV light for 12 h. The solution was concentrated and the residue was purified on RP18. Yield: 407 mg; $^1$H NMR (500 MHz, CD$_3$OD): δ ppm 7.93 (d, J=8.64 Hz, 2H), 7.72 (d, J=8.66 Hz, 2H), 7.66 (dd, J=8.38, 1.23 Hz, 2H), 7.46 (t, J=7.60 Hz, 2H), 7.38 (t, J=7.38 Hz, 1H), 4.07 (ddd, J=8.67, 7.73, 3.08 Hz, 1H), 3.93 (dd, J=13.76, 2.91 Hz, 1H), 3.92 (ddd, J=9.63, 7.03, 5.02 Hz, 1H), 3.88-3.84 (m, 1H), 3.86 (s, 3H), 3.82 (dd, J=10.34, 1.28 Hz, 1H), 3.47 (dd, J=8.76, 1.42 Hz, 1H), 3.47-3.43 (m, 1H), 3.43 (dd, J=13.83, 7.64 Hz, 1H), 3.14 (t, J=6.96 Hz, 1H), 3.14 (t, J=6.56 Hz, 1H), 2.80 (t, J=6.75 Hz, 2H), 2.64 (t, J=6.97 Hz, 2H), 2.55 (dd, J=12.94, 4.00 Hz, 1H), 1.93 (s, 3H), 1.86-1.71 (m, 3H), 1.43 (s, 9H); HRMS (ESI-neg) calculated for C36H48N3NaO12S [M-Na]$^-$: 719.3320, found: 719.3335.

Biological Tests

The biological activity of the substances was determined in an ELISA-based inhibition assay as described in "Eur. J. Immunol. 2012, 42, 2792-2802". The sialic acid derivatives of the formula (I) inhibit the binding of soluble CD22 to immobilized IgM in proportion to their affinity for CD22. The soluble CD22 protein was expressed in the CHO-Lec1 cell line and isolated as described by "Eur. J. Immunol. 2012, 42, 2792-2802". The known substance "BPCNeu5Ac" (J. Exp. Med. 2002, 195, 1207-1213) was co-tested in the assays as a reference. The increase in affinity is reported as rIP (relative inhibitory affinity).

Table I shows the affinity or relative inhibitory potency (rIP) of the sialic acid derivatives of the formula (I).

TABLE I

| No. | Structure | IC50 microM | rIP |
|-----|-----------|-------------|-----|
| BPC Neu5Ac | 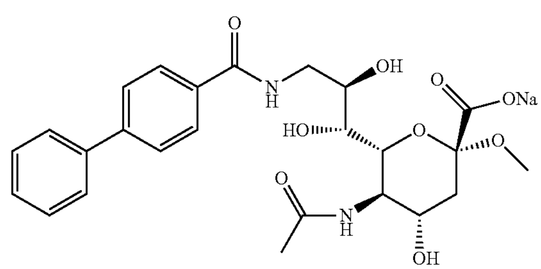 | 6.1 | 1 |
| 10 | 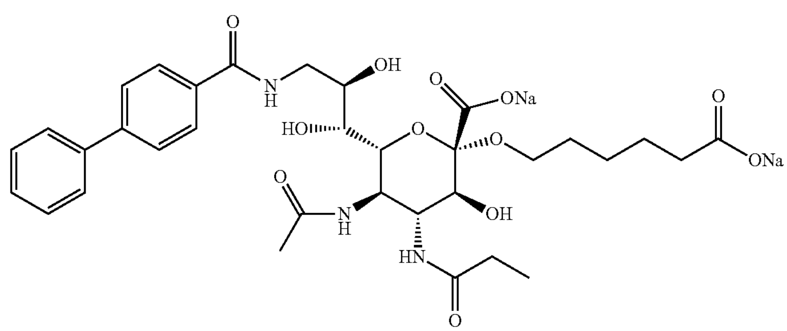 | 0.0060 | 1014 |
| 11 | 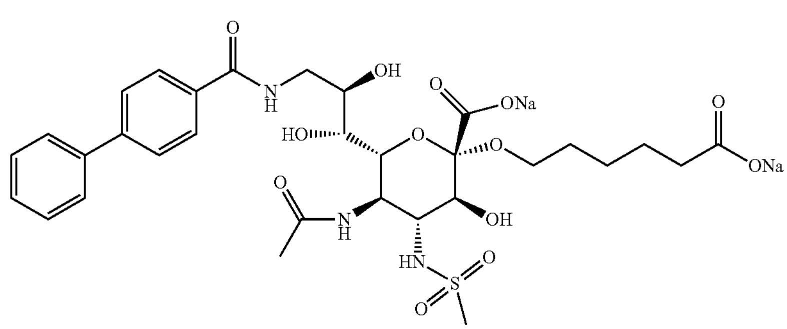 | 0.0077 | 793 |

TABLE I-continued

| No. | Structure | IC50 microM | rIP |
|---|---|---|---|
| 15 | 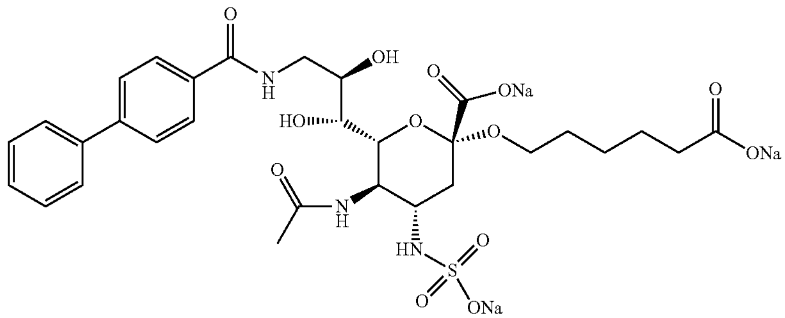 | 0.0032 | 1920 |
| 17 | 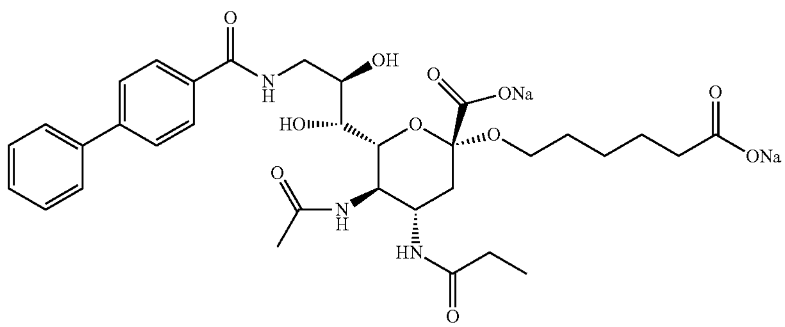 | 0.012 | 502 |
| 20 | 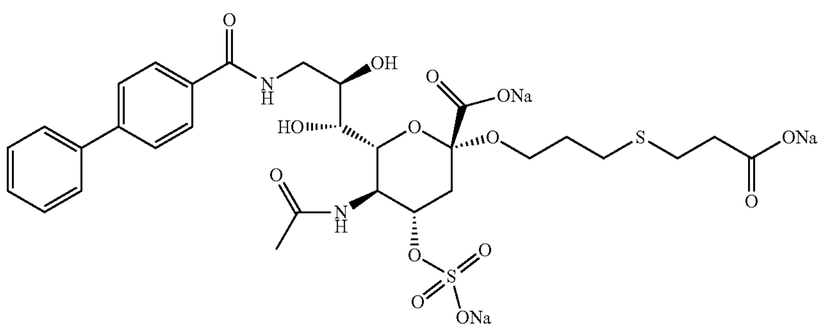 | 0.0020 | 3130 |
| 29 | 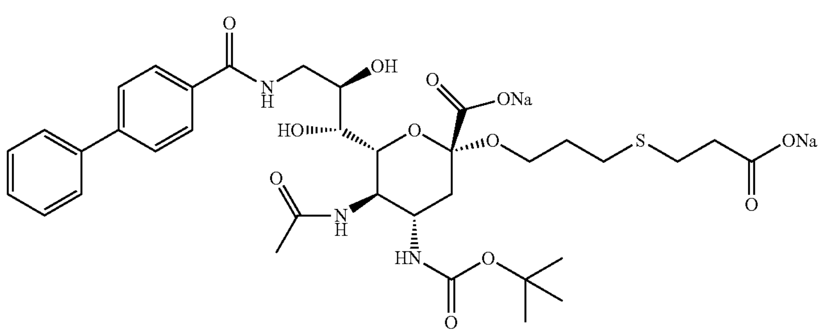 | 0.085 | 71 |

TABLE I-continued

| No. | Structure | IC50 microM | rIP |
|---|---|---|---|
| 37 | 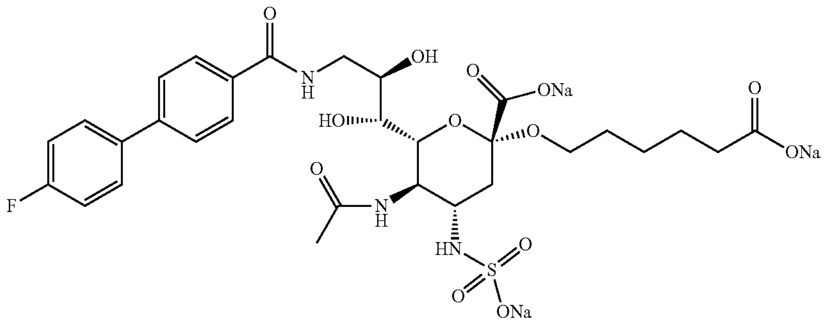 | 0.015 | 405 |

Further sialic acid derivatives of the formula (I) for which rIP values were determined are listed in Table II. As a reference, compound 10, a sialic acid derivative of the formula (I) with surprisingly high affinity, was co-tested in the same assay. The sialic acid derivatives of the formula (I) in Table II show an affinity level comparable with that of reference compound 10.

TABLE II

| No. | Structure | rIP |
|---|---|---|
| 10 | 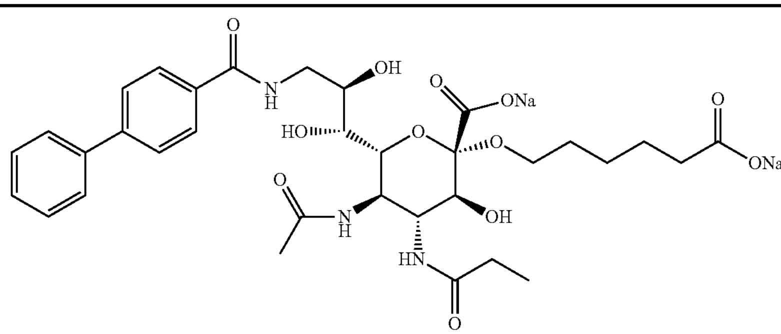 | 1 |
| 38 | 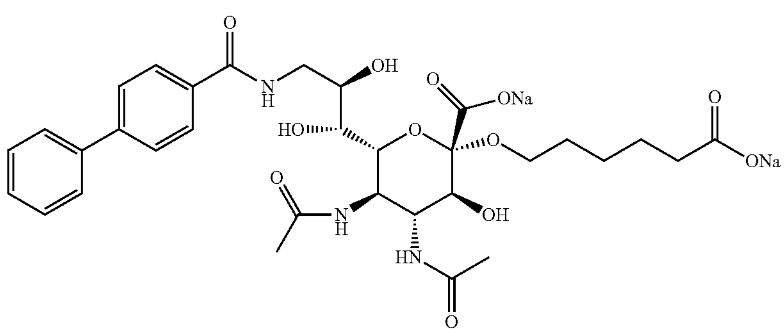 | 0.45 |
| 39 | 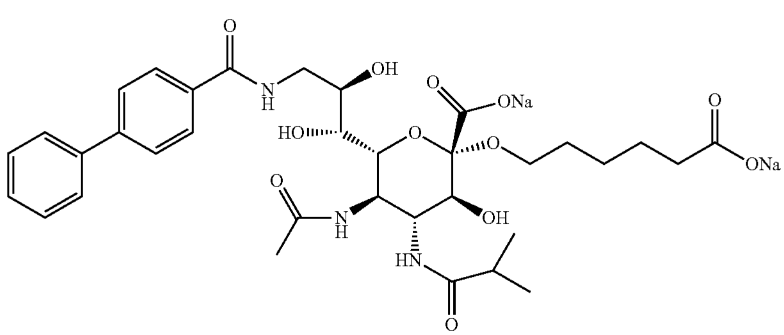 | 0.70 |

TABLE II-continued

| No. | Structure | rIP |
|---|---|---|
| 40 | 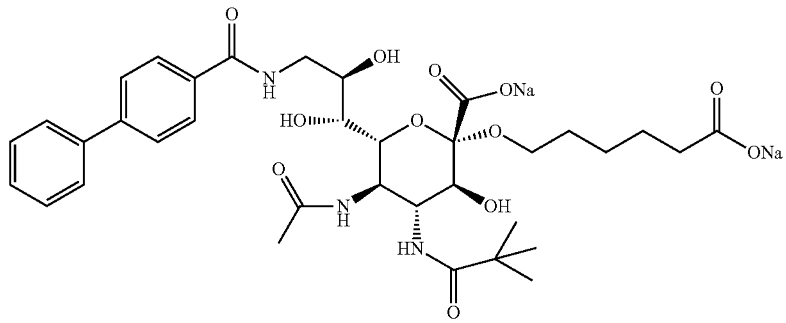 | 0.38 |
| 41 | 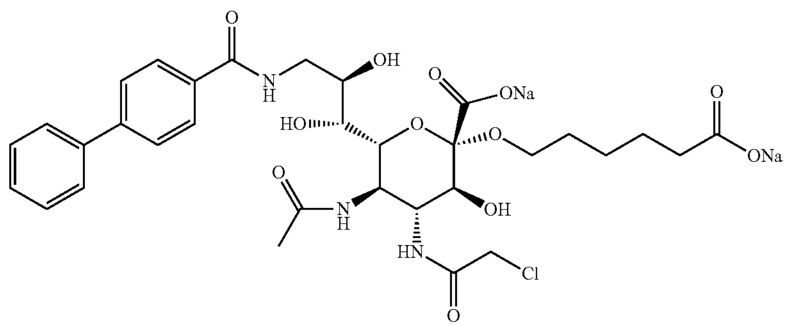 | 0.37 |
| 42 | 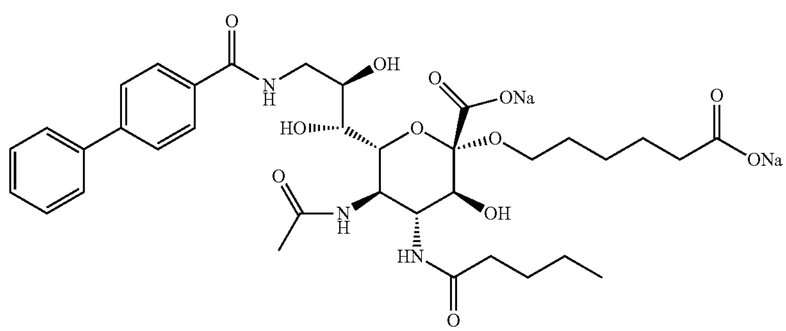 | 1.22 |
| 43 | 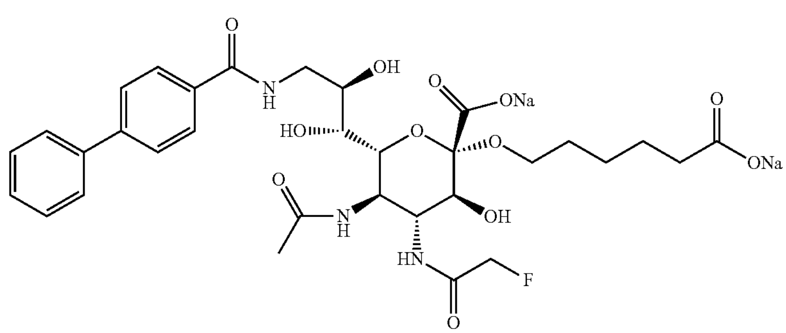 | 0.25 |

TABLE II-continued

| No. | Structure | rIP |
|---|---|---|
| 44 | 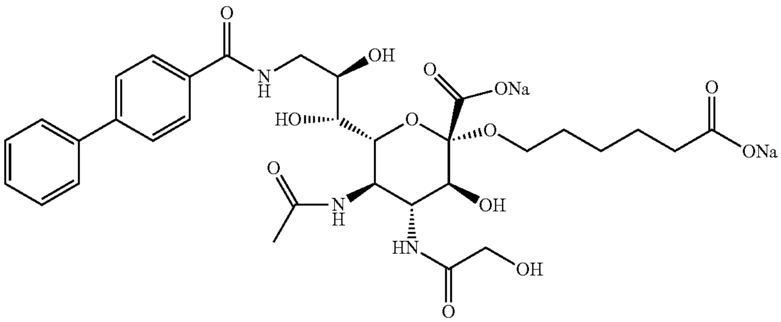 | 0.24 |
| 45 | 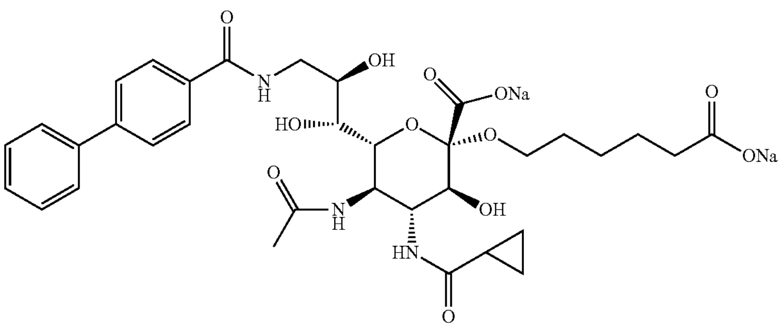 | 0.81 |
| 46 | 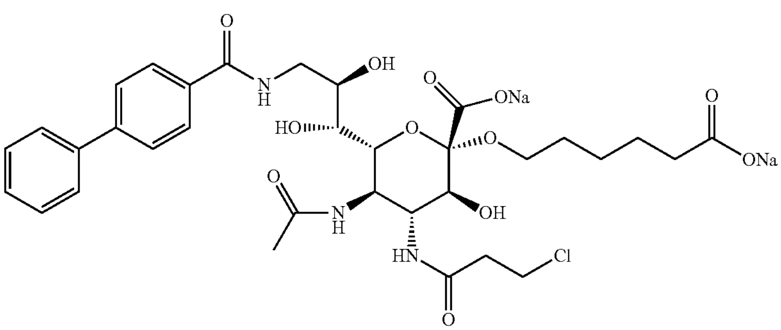 | 0.84 |
| 47 | 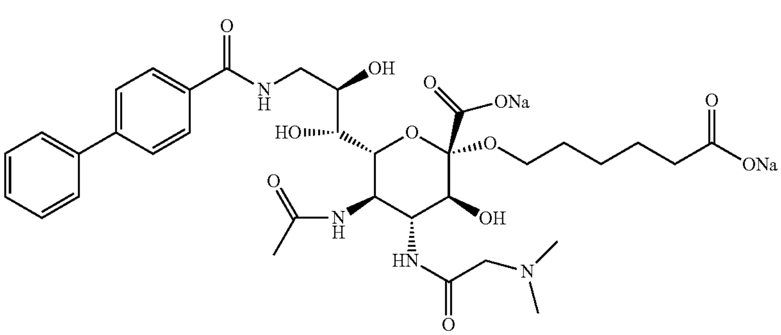 | 0.18 |

TABLE II-continued

| No. | Structure | rIP |
|---|---|---|
| 48 | 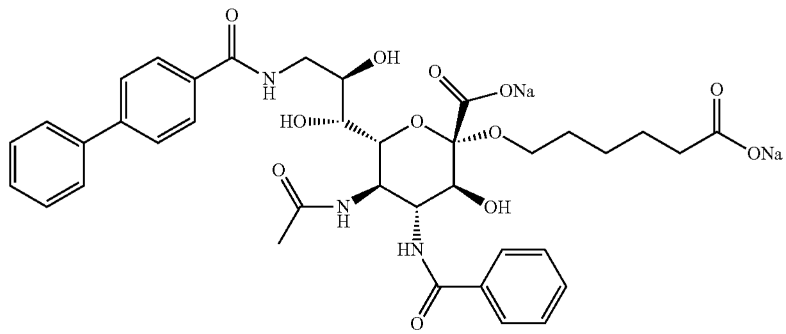 | 0.93 |
| 49 | 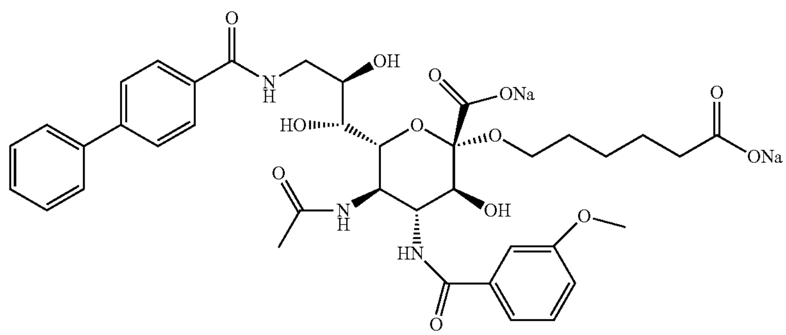 | 0.34 |
| 50 | 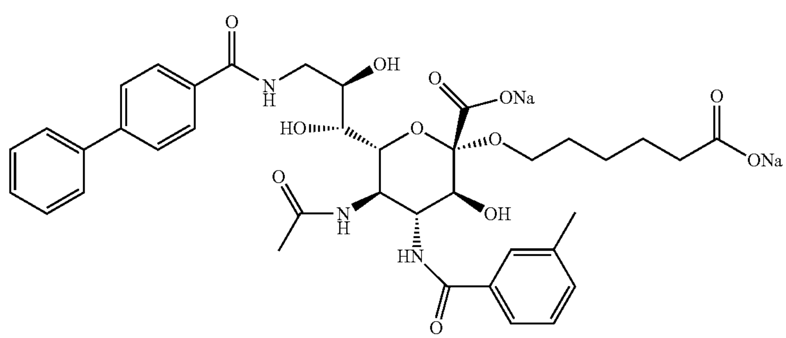 | 0.51 |
| 51 | 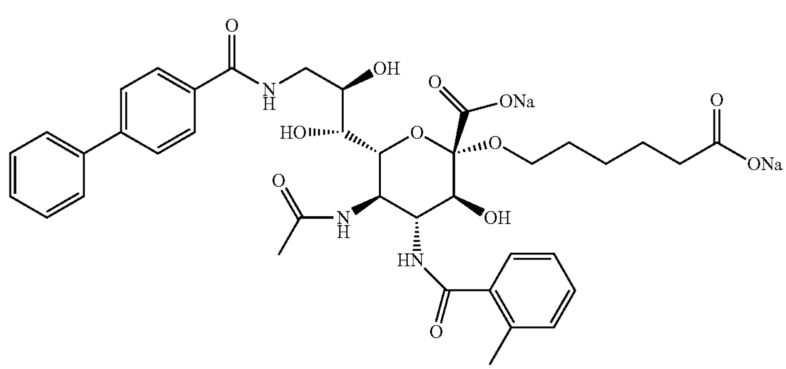 | 0.13 |

TABLE II-continued

| No. | Structure | rIP |
|---|---|---|
| 52 | 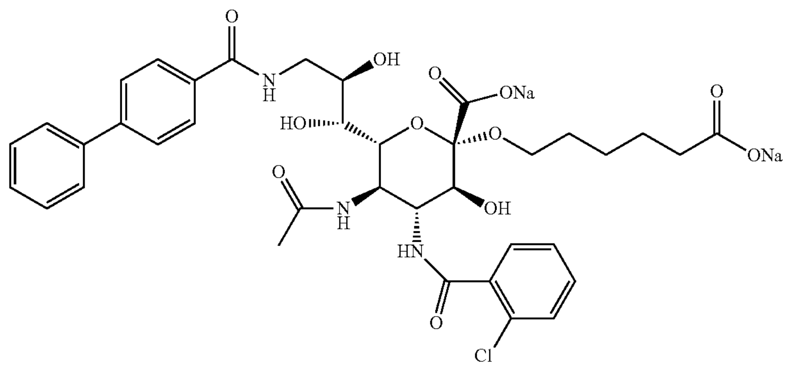 | 0.12 |
| 65 | 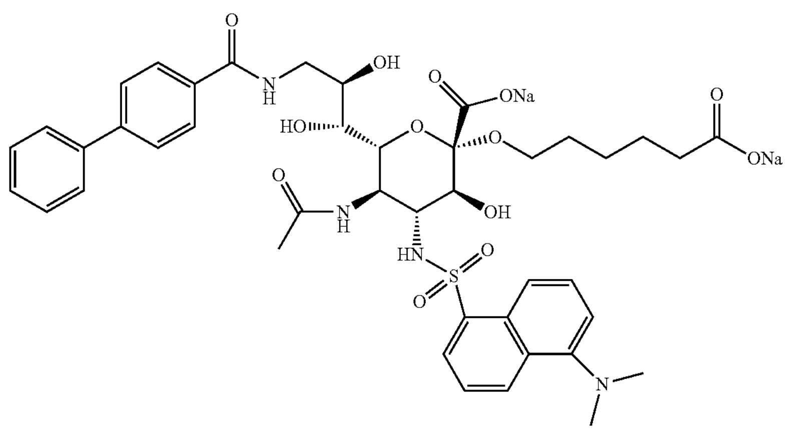 | 0.17 |

Further sialic acid derivatives of the formula (I) for which rIP values were determined are listed in Table III. As a reference, compound 17, a sialic acid derivative of the formula (I) with surprisingly high affinity, was co-tested in the same assay. The sialic acid derivatives of the formula (I) in Table III show an affinity level comparable with that of reference compound 17.

TABLE III

| No. | Structure | rIP |
|---|---|---|
| 17 | 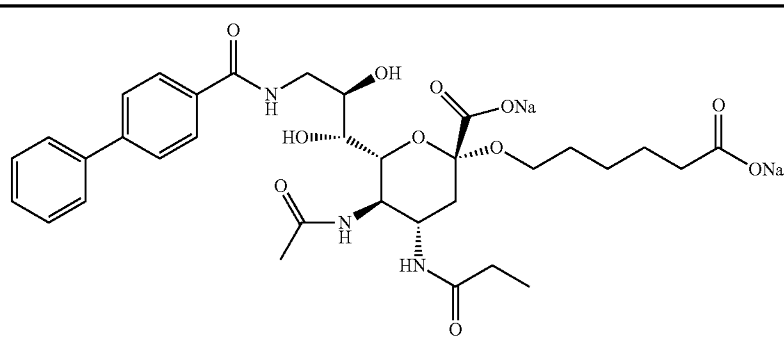 | 1 |

TABLE III-continued

| No. | Structure | rIP |
|-----|-----------|-----|
| 53 | 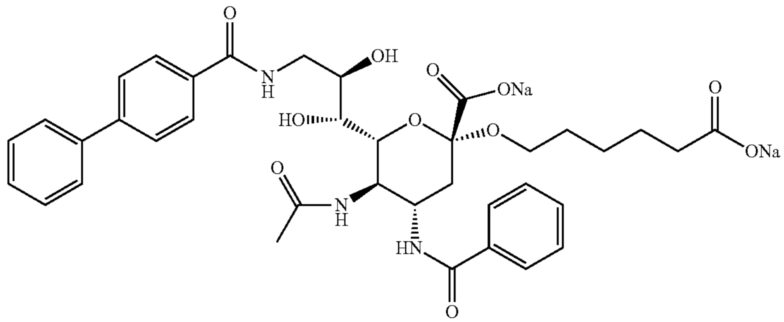 | 1.1 |
| 54 | 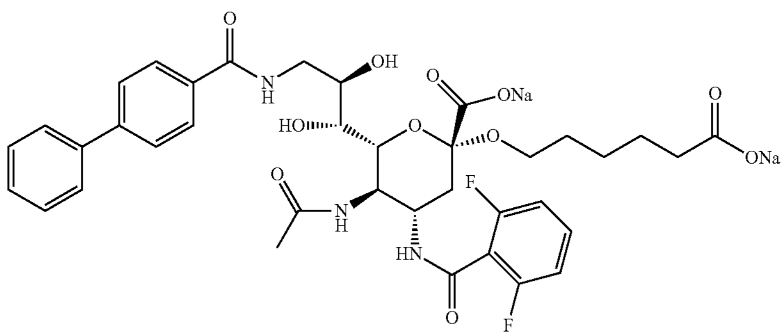 | 0.75 |
| 55 | 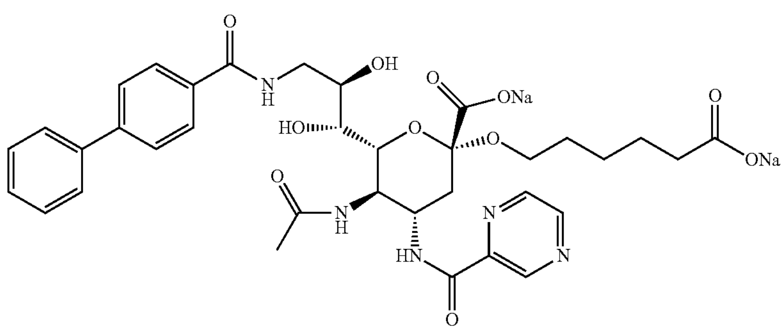 | 2.7 |
| 56 | 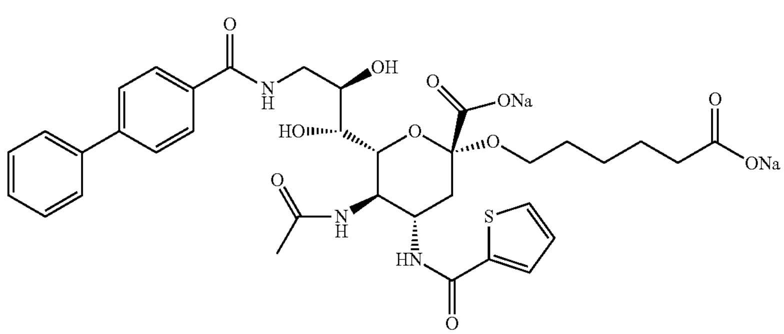 | 3.6 |

TABLE III-continued

| No. | Structure | rIP |
|---|---|---|
| 57 | 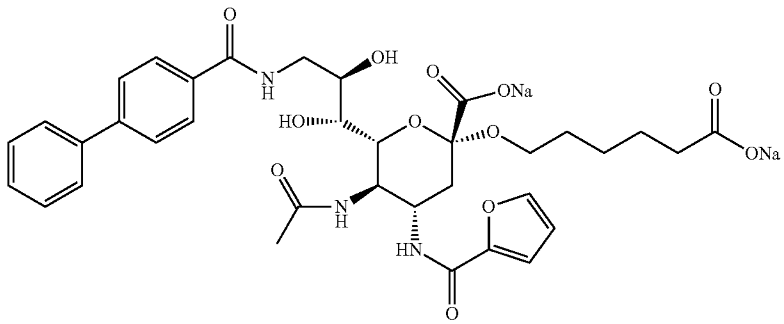 | 6.1 |
| 58 | 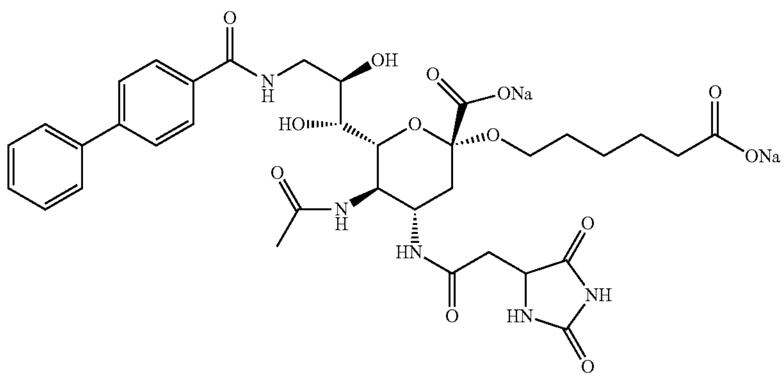 | 3.4 |
| 59 | 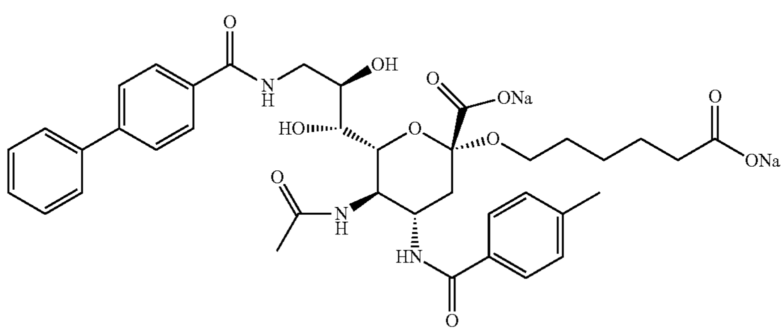 | 0.24 |
| 60 | 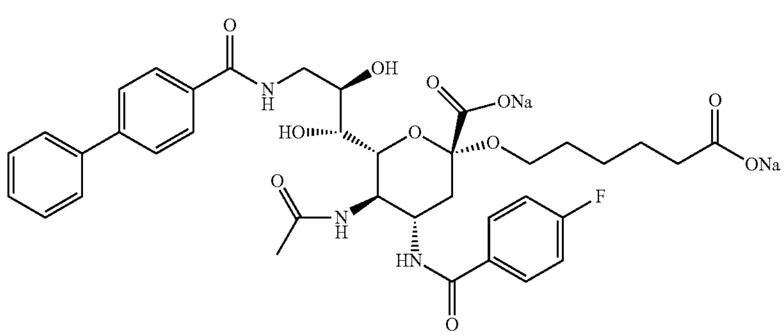 | 2.1 |

TABLE III-continued

| No. | Structure | rIP |
|---|---|---|
| 61 | 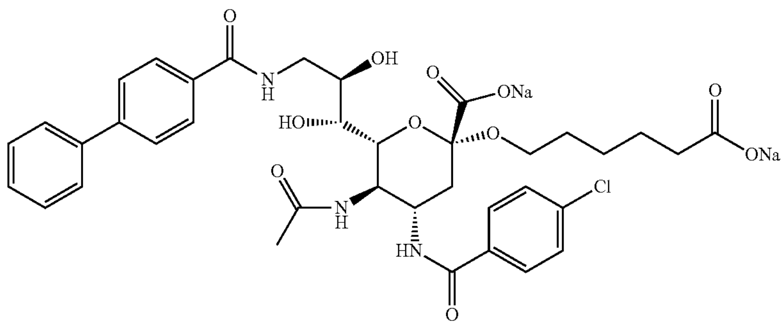 | 3.4 |
| 62 | 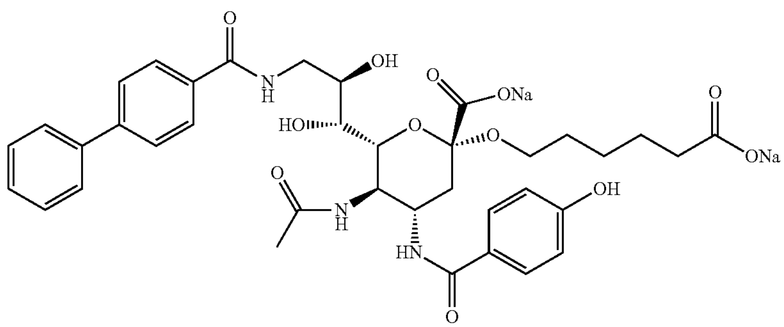 | 1.7 |
| 63 | 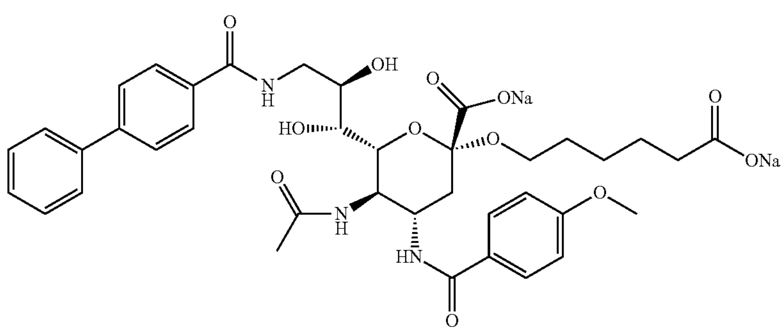 | 0.27 |
| 64 | 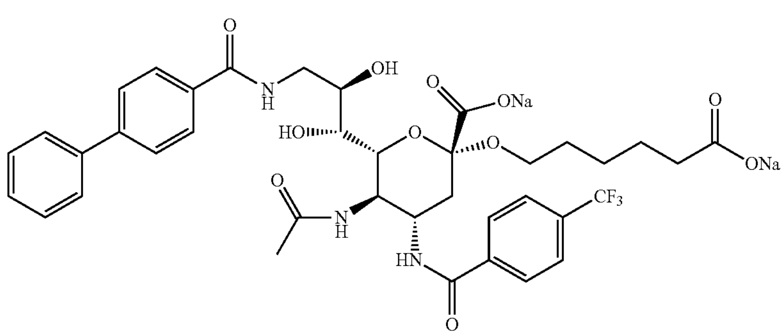 | 1.2 |

TABLE III-continued

| No. | Structure | rIP |
|---|---|---|
| 66 | 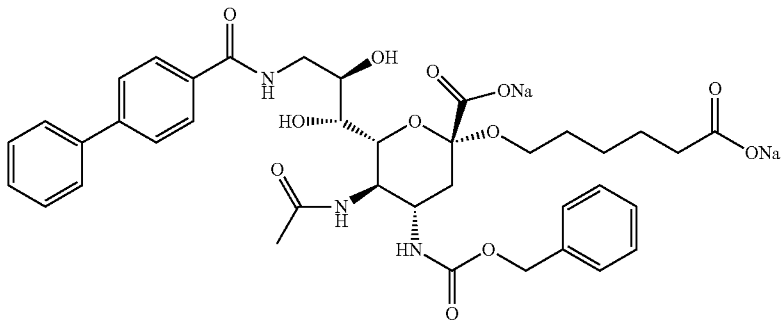 | 1.3 |

Further sialic acid derivatives of the formula (I) for which rIP values were determined are listed in Table IV. As a reference, compound 66 was co-tested in the same assay.

The sialic acid derivatives of the formula (I) in Table IV show an affinity level comparable with that of reference compound 66.

TABLE IV

| No. | Structure | rIP |
|---|---|---|
| 66 | 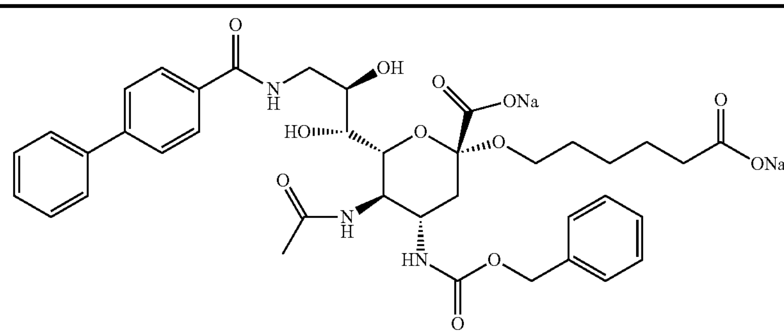 | 1 |
| 67 | 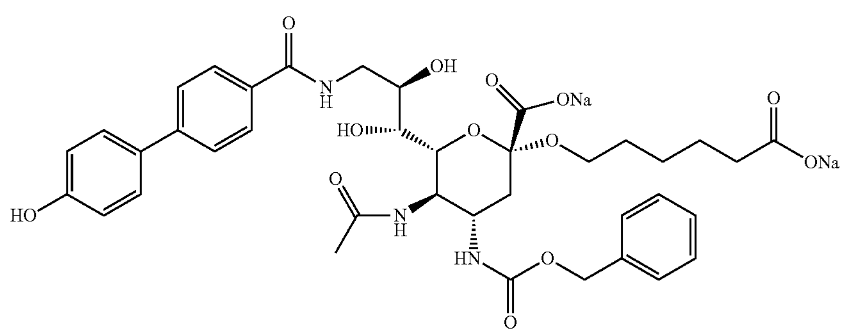 | 1.0 |
| 68 | 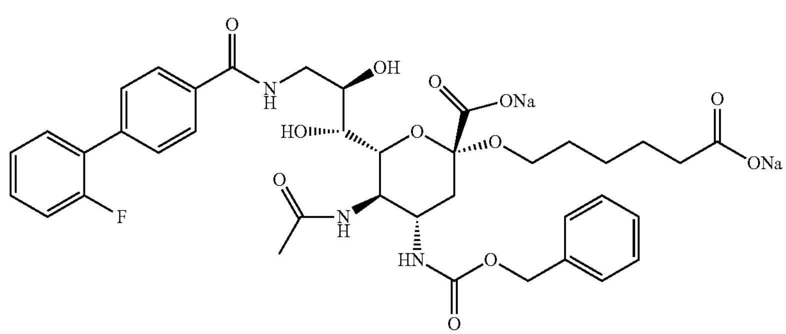 | 0.76 |

TABLE IV-continued

| No. | Structure | rIP |
|---|---|---|
| 69 | 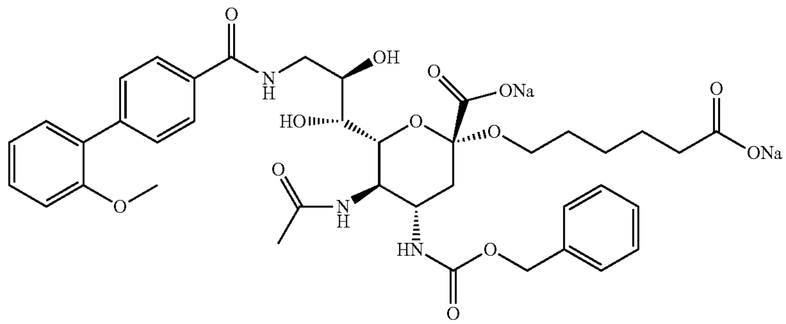 | 0.83 |
| 70 | 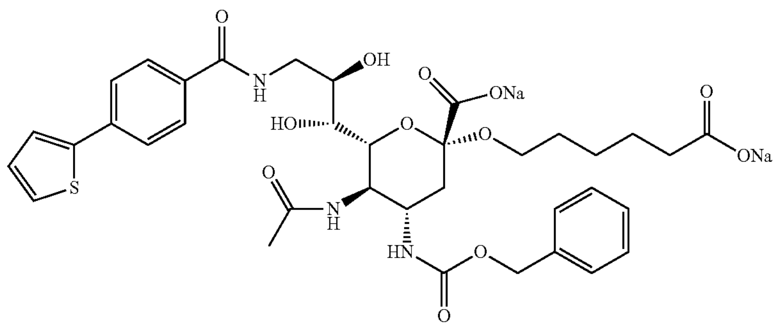 | 0.88 |
| 71 | 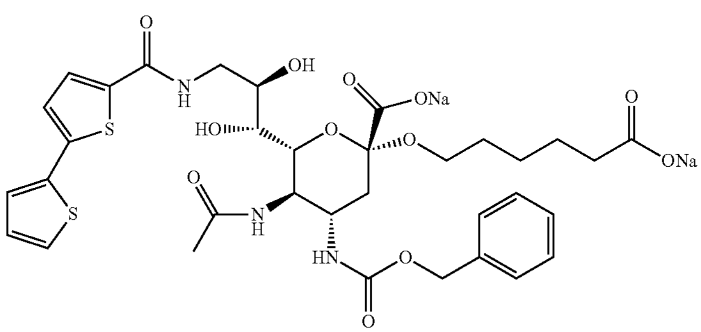 | 0.28 |
| 72 | 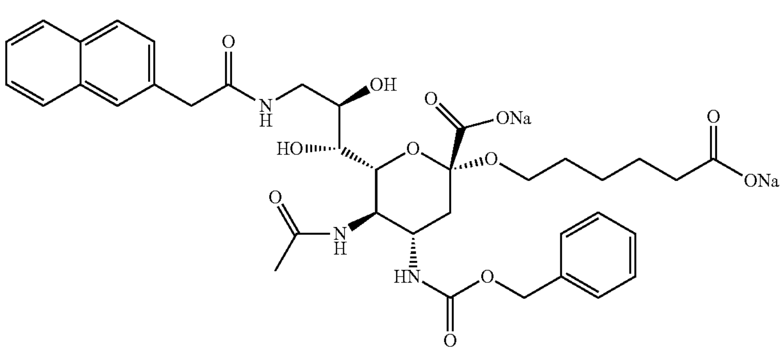 | 0.91 |

TABLE IV-continued

| No. | Structure | rIP |
|-----|-----------|-----|
| 73 | 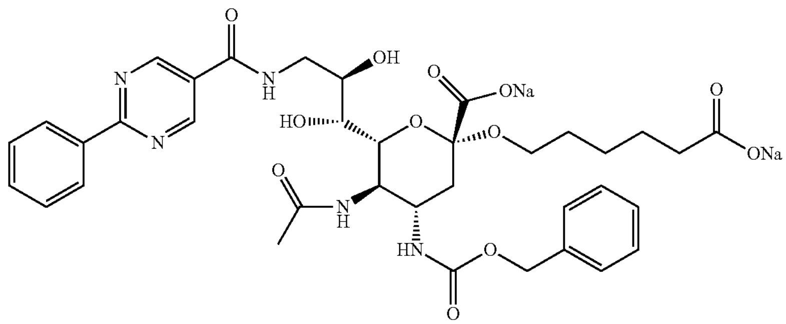 | 0.23 |
| 74 | 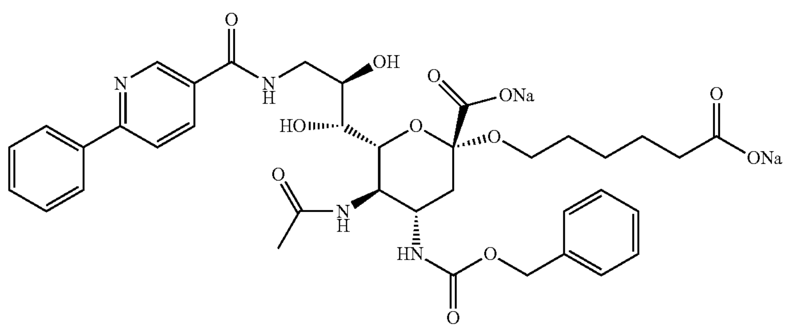 | 0.20 |
| 75 | 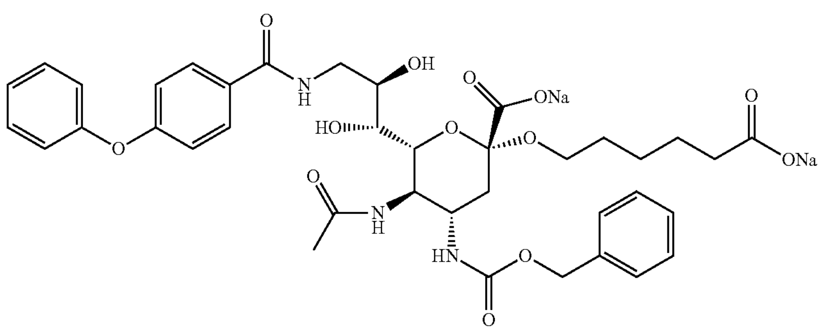 | 0.25 |
| 76 | 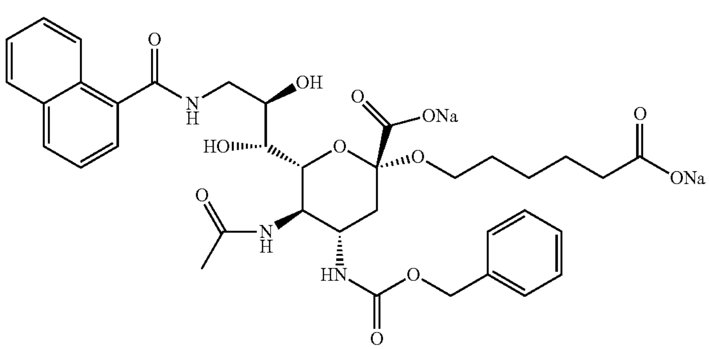 | 0.35 |

Table V shows sialic acid derivatives of the formula (I) which are suitable as prodrugs, their affinity for CD22 having not been determined, since the active molecule is liberated only in vivo by enzymatic cleavage.

TABLE V
| No. | Structure |
|---|---|
| 16 | 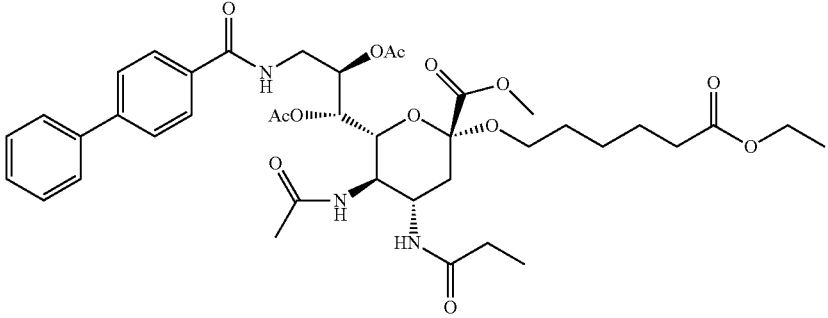 [SMILES: CCOC(=O)CCCCCO[C@]1(C(=O)OC)C[C@H](NC(=O)CC)[C@@H](NC(C)=O)[C@H]([C@H](OC(C)=O)[C@@H](CNC(=O)c2ccc(-c3ccccc3)cc2)OC(C)=O)O1] |
| 18 | 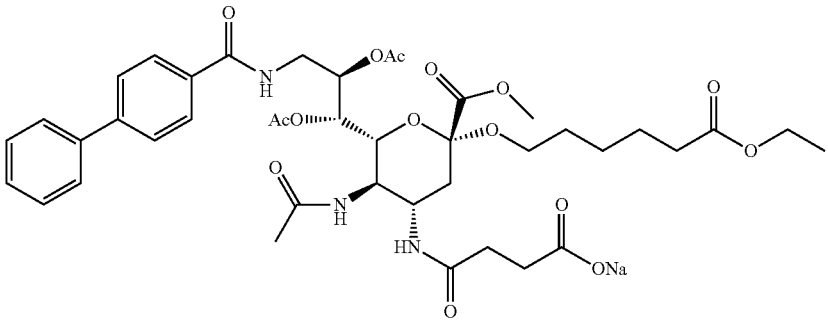 |
| 28 | 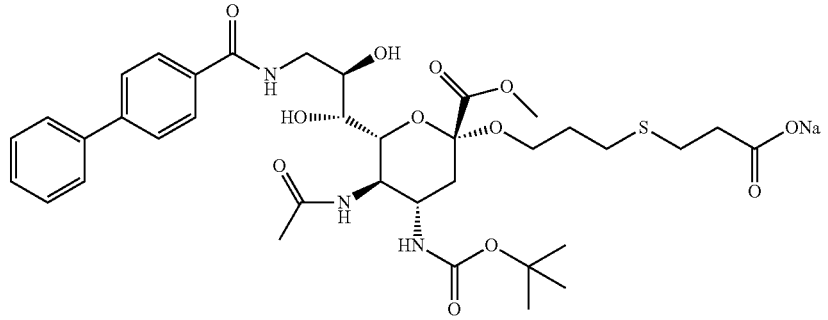 |
| 36 | 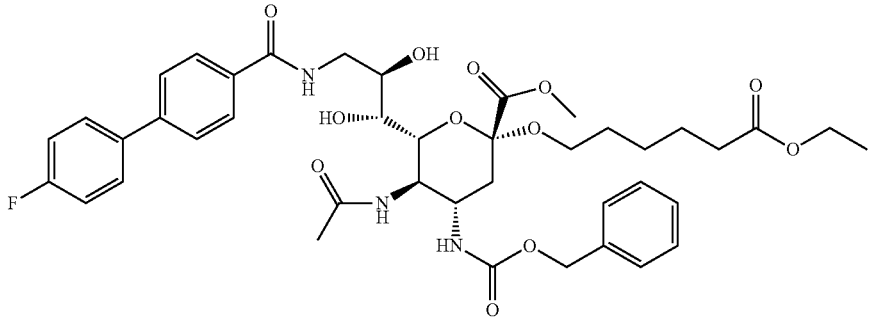 [SMILES: CCOC(=O)CCCCCO[C@]1(C(=O)OC)C[C@H](NC(=O)OCc2ccccc2)[C@@H](NC(C)=O)[C@H]([C@H](O)[C@H](O)CNC(=O)c2ccc(-c3ccc(F)cc3)cc2)O1] |

TABLE V-continued

| No. | Structure |
|---|---|
| 77 | 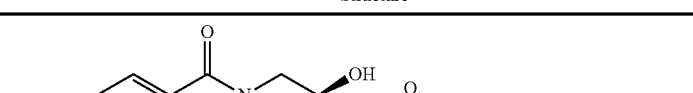 |

The invention claimed is:

1. Sialic acid derivative of the formula (I),

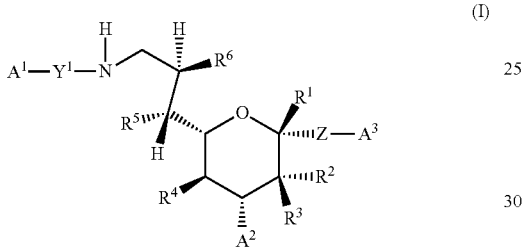

where the symbols have the following definitions:

$A^1$ is a group $D^1$-$[Y^2$-$D^2$-$]_m$-;

$D^1$ is a mono- or polycyclic aromatic, partially unsaturated or saturated $C_3$-$C_{14}$ hydrocarbon radical or a mono- or polycyclic aromatic, partially unsaturated or saturated three- to twelve-membered heterocyclic radical, the stated radicals being unsubstituted or substituted one or more times by a group X;

$D^2$ is a mono- or polycyclic aromatic, partially unsaturated or saturated $C_3$-$C_{14}$ hydrocarbon radical or a mono- or polycyclic aromatic, partially unsaturated or saturated three- to eight-membered heterocyclic radical, the stated radicals being unsubstituted or substituted one or more times by a group X;

$Y^1$ is ~C(O)—, ~S(O)$_2$—, ~NHC(O)—, ~($C_1$-$C_2$ alkyl)-, ~($C_1$-$C_2$ alkyl)-C(O)—, ~CH═CH—C(O)—, ~C≡C—C(O)—, ~($C_1$-$C_2$ alkyl)-S(O)$_2$—, ~OC(O)—, ~($C_1$-$C_2$ alkyl)-OC(O)— or ~($C_1$-$C_2$ alkyl)-NHC(O)—, where ~ denotes the bond to the group $A^1$;

$Y^2$ is —O—, —C(O)—, —S(O)$_2$—, —CH$_2$— or a bond;

$A^2$ is
  a) a group —OS(O)$_2$OL or
  b) a group —N(R$^x$)—W;

W is
  a) a group ~SO$_3$L, ~SO$_2$CF$_3$ or ~SO$_2$NR$^x{}_2$ or
  b) a group $D^3$-$Y^3$—;

$Y^3$ is a bond or a group ~O(CO)NHS(O)$_2$—, ~NHC(O)—, ~OC(O)—, ~CH$_2$OC(O)—, ~S(O)$_2$—, ~C(O)—, ~($C_1$-$C_2$ alkyl)-C(O)—, ~($C_1$-$C_2$ alkyl)-NHC(O)— or ~($C_1$-$C_2$ alkyl)-S(O)$_2$—, where ~ denotes the bond to the group $D^3$;

$D^3$ is
  a) $C_1$-$C_6$ alkyl, where optionally one or more non-terminal CH$_2$ groups are replaced by O, N(R$^x$) and/or C(O), and where optionally one or more H atoms in the stated groups are replaced by a group X,
  b) is a mono- or polycyclic aromatic, partially unsaturated or saturated $C_3$-$C_{14}$ hydrocarbon radical or a mono- or polycyclic aromatic, partially unsaturated or saturated three- to eight-membered heterocyclic radical, the stated radicals being unsubstituted or substituted one or more times by a group X;

$A^3$ is
  a) $C_1$-$C_8$ alkyl, where optionally
    a. one or more non-terminal —CH$_2$— groups are replaced by S, O, N(R$^x$) and/or C(O), or
    b. a —CH$_2$CH$_2$CH$_2$— group is replaced by 1,2-phenyldiyl, 1,3-phenyldiyl or 1,4-phenyldiyl, and where optionally one or more H atoms in the stated groups are replaced by a group X, or
  b) is a mono- or polycyclic aromatic, partially unsaturated or saturated $C_3$-$C_{14}$ hydrocarbon radical or a mono- or polycyclic aromatic, partially unsaturated or saturated three- to eight-membered heterocyclic radical, the stated radicals being substituted one or more times by a group X;

X is identically or differently halogen, cyano, nitro, hydroxyl, mercapto, amino, carboxyl, carboxymethyl, hydroxylamino, azido, B(OH)$_2$), SO, SO$_3$M, OSO$_3$M, SO$_2$NH$_2$, SO$_2$CF$_3$, PO$_3$M, OPO$_3$M, cyanomethyl, haloalkyl, alkyloxy, haloalkyloxy, alkylamino, dialkylamino, trialkylamino, formyl, alkylcarbonyl, alkylsulfonyl, alkylsulfoxyl, alkylaminosulfonyl, dialkylaminosulfonyl, alkyloxycarbonyl, alkylcarbonyloxy, aminocarbonyl, alkylaminocarbonyl, alkylcarbonylamino, dialkylaminocarbonyl, oxo (═O), thioxo (═S), $C_1$-$C_8$ alkylimino (═N—$C_1$-$C_8$ alkyl) or $C_1$-$C_8$ alkyloximino (═N—O—$C_1$-$C_8$ alkyl), the alkyl groups in these radicals containing 1 to 6 carbon atoms;

m is 0, 1 or 2;

Z is ~O—, ~S—, —ON═CH~, ~ON(R$^x$)—, ~N(R$^x$)— or ~4-1H-(1,2,3)triazol-1-yl-, where ~ denotes the bond to the group $A^3$;

$R^1$ is C(O)OM;

$R^2$ is H, F, Cl, NR$^x$ or OR$^x$;

$R^3$ is H, F, Cl, $NR^x$ or $OR^x$;

$R^4$ is $N(R^x)C(O)CH_2OH$ or $N(R^x)C(O)R^x$;

$R^5$, $R^6$ are identically or differently OH or $OR^x$;

L is a cation;

M is $C_1$-$C_4$ alkyl or a cation;

$R^x$ is identically or differently H, $R^y$ or $R^z$;

$R^y$ is identically or differently $C_1$-$C_4$ alkyl, phenyl or benzyl, and $R^z$ is identically or differently —C(O)—$C_1$-$C_4$ alkyl, —C(O)-phenyl or C(O)—$CH_2$-phenyl, where alkyl groups in each case are straight-chain, branched or cyclic, a pharmacologically tolerated salt or prodrug thereof.

2. Sialic acid derivative of the formula (I) according to claim 1, where the symbols in the formula (I) have the following definitions:

$A^1$ is a group $D^1$-$[Y^2$-$D^2$-$]_m$-;

$D^1$ is a mono- or polycyclic aromatic or saturated $C_3$-$C_{14}$ hydrocarbon radical or a monocyclic aromatic, partially unsaturated or saturated four- to six-membered heterocyclic radical, the stated radicals being unsubstituted or substituted one or more times by a group X;

$D^2$ is a group phenylene-1,4-diyl, phenylene-1,3-diyl, pyridine-2,5-diyl, pyridazine-3,6-diyl, pyrimidine-2,5-diyl, pyrimidine-2,6-diyl, pyrazine-2,5-diyl, trans-cyclobutane-1,3-diyl, trans-cyclopentane-1,3-diyl, trans-cyclohexane-1,4-diyl, cubane-1,4-diyl, thiophene-2,5-diyl, pyrrole-2,4-diyl, pyrrole-2,5-diyl, pyrazole-1,3-diyl, oxazole-2,4-diyl, oxazole-2,5-diyl, 1,3,4-oxadiazole-2,5-diyl, 1,2,4-oxadiazole-3,5-diyl, isooxazole-3,5-diyl, imidazole-2,4-diyl, 2H-tetrazole-2,5-diyl, 1H(1,2,4)-triazole-2,5-diyl, 1H(1,2,3)-triazole-1,4-diyl or 1H(1,2,3)-triazole-1,5-diyl, the stated radicals being unsubstituted or substituted one or more times by a group X;

$Y^1$ is ~C(O)—, ~S(O)$_2$—, ~NHC(O)—, ~$CH_2$C(O)—, ~$CH_2$—S(O)$_2$—, ~OC(O)—, ~$CH_2$—OC(O)— or ~$CH_2$NHC(O)—, where ~ denotes the bond to the group $A^1$;

$Y^2$ is —O—, —$CH_2$— or a bond;

$A^2$ is
  a) a group —OS(O)$_2$OL or
  b) a group —N($R^x$)—W;

W is
  a) a group ~SO$_3$L, ~SO$_2$CF$_3$ or ~SO$_2$NR$^x_2$ or
  b) a group $D^3$-$Y^3$—;

$Y^3$ is a bond or a group ~NHC(O)—, ~OC(O)—, ~$CH_2$OC(O)—, ~S(O)$_2$—, ~C(O)—, ~$CH_2$—C(O)—, ~$CH_2$—NHC(O)— or ~$CH_2$—S(O)$_2$—, where ~ denotes the bond to the group $D^3$;

$D^3$ is
  a) a $C_1$-$C_6$ alkyl, where optionally one or more non-terminal $CH_2$ groups are replaced by O and where optionally one or more H atoms in the stated groups are replaced by a group X, or
  b) a monocyclic or polycyclic aromatic or saturated $C_3$-$C_{14}$ hydrocarbon radical or a monocyclic aromatic, partially unsaturated or saturated four- to six-membered heterocyclic radical, the stated radicals being unsubstituted or substituted one or more times by a group X;

$A^3$ is a $C_3$-$C_8$ alkyl, where optionally
  a) one or more non-terminal —$CH_2$— groups are replaced by S or O, or
  b) a —$CH_2CH_2CH_2$— group is replaced by 1,2-phenyldiyl, 1,3-phenyldiyl or 1,4-phenyldiyl, and where optionally one or more H atoms in the stated groups are replaced by a group X;

X is identically or differently halogen, hydroxyl, amino, carboxyl, carboxymethyl, SO$_3$M, OSO$_3$M, SO$_2$NH$_2$, SO$_2$CF$_3$, haloalkyl, alkyloxy, alkylamino, dialkylamino, trialkylamino, alkylsulfonyl, alkyloxycarbonyl, alkylcarbonyloxy, alkylaminocarbonyl, alkylcarbonylamino or oxo (=O), the alkyl groups in these radicals containing 1 to 3 carbon atoms;

m is 0 or 1;

Z is ~O—, ~S— or ~4-1H-(1,2,3)triazol-1-yl, where ~ denotes the bond to the group $A^3$;

$R^1$ is C(O)OM;

$R^2$ is H or F;

$R^3$ is H, F, Cl or $OR^x$;

$R^4$ is NHC(O)$CH_2$OH or NHC(O)$CH_3$;

$R^5$, $R^6$ are identically or differently OH or $OR^z$;

L is a cation;

M is a $C_1$-$C_3$ alkyl or a cation;

$R^x$ is identically or differently H, $R^y$ or $R^z$;

$R^y$ is identically or differently $C_1$-$C_3$ alkyl, phenyl or benzyl and $R^z$ is identically or differently —C(O)—$C_1$-$C_3$ alkyl or —C(O)-phenyl, a pharmacologically tolerated salt or prodrug thereof.

3. Sialic acid derivative of the formula (I) according to claim 1, where the symbols in the formula (I) have the following definitions:

$A^1$ is a group $D^1$-$[Y^2$-$D^2$-$]_m$-;

$D^1$ is a group phenyl, pyrimidin-5-yl, naphth-1-yl, naphth-2-yl, or thien-2-yl, the stated radicals being unsubstituted or substituted one or more times by a group X;

$D^2$ is a group phenylene-1,4-diyl, pyridine-2,5-diyl, pyrimidine-2,5-diyl or thiophene-2,5-diyl, the stated radicals being unsubstituted or substituted one or more times by a group X;

$Y^1$ is ~C(O)— or —$CH_2$C(O)—, where ~ denotes the bond to the group $A^1$;

$Y^2$ is a bond;

$A^2$ is
  a) a group —OS(O)$_2$OL or
  b) a group —NH—W;

W is
  a) a group ~SO$_3$L or
  b) a group $D^3$-$Y^3$—;

$Y^3$ is a bond or a group ~$CH_2$OC(O)—, ~OC(O)—, ~S(O)$_2$—, ~C(O)— or ~$CH_2$—C(O)—, where ~ denotes the bond to the group $D^3$;

$D^3$ is a group methyl, ethyl, prop-2-yl, pent-5-yl, cyclopropyl, 1,1-dimethylethyl, phenyl, thien-2-yl, furan-2-yl, imidazolidin-5-yl, pyrazin-5-yl, or naphthalin-1-yl;

$A^3$ is a group pentan-1-yl or hexan-1-yl; where one or more H atoms in the stated groups are replaced by a group X;

X is identically or differently fluoro, chloro, hydroxyl, carboxyl, trifluoromethyl, methoxy, dimethylamino or oxo (=O);

m is 0 or 1;

Z is ~O—;

$R^1$ is C(O)OM;

$R^2$ is H;

$R^3$ is H or OH;

$R^4$ is $NHC(O)CH_3$;

$R^5$, $R^6$ are identically or differently OH or $OC(O)CH_3$;

L is a cation;

M is methyl, ethyl or a cation, a pharmacologically tolerated salt or prodrug thereof.

4. Sialic acid derivative of the formula (I) according to claim 1, characterized by one of the formulae Ia to Ich, where the symbols have the definitions indicated in the formula (I):

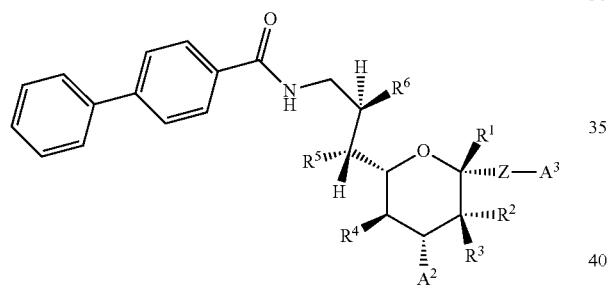

Ia

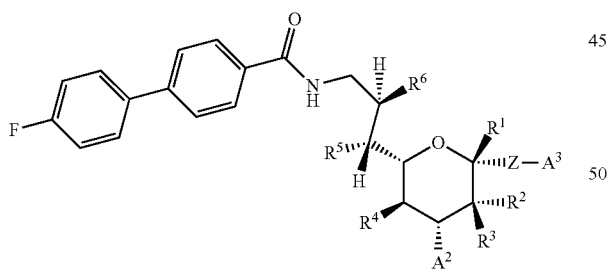

Ib

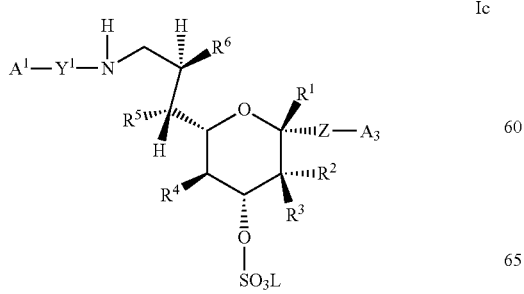

Ic

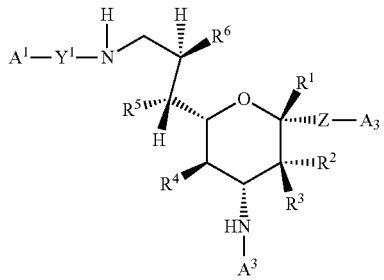

Id

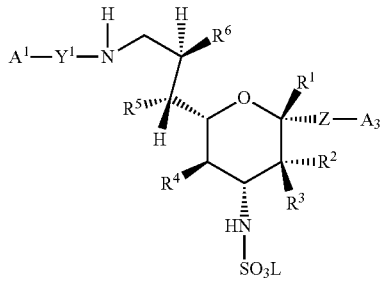

Ie

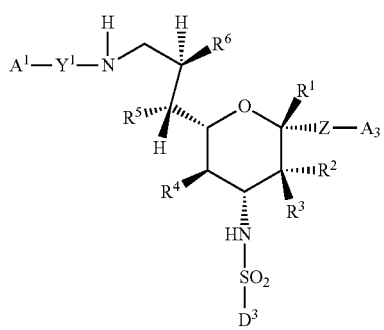

If

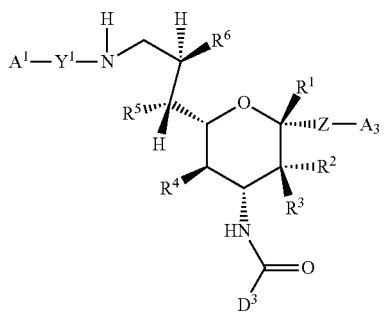

Ig

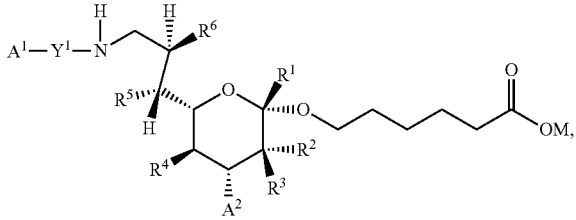

Ih a pharmacologically tolerated salt or prodrug thereof.

5. Sialic acid derivative of the formula (I) according to claim 1, characterized by one of the formulae (Iaa)-(Iam), where the symbols have the definitions indicated in the formula (I):

Iaa
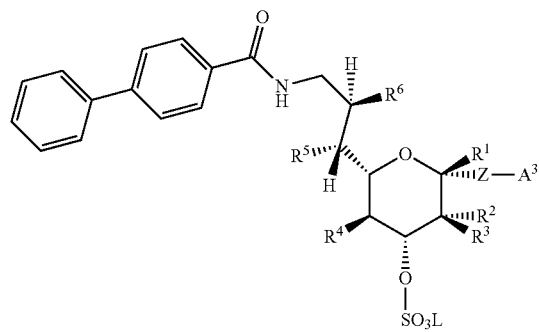
Iab
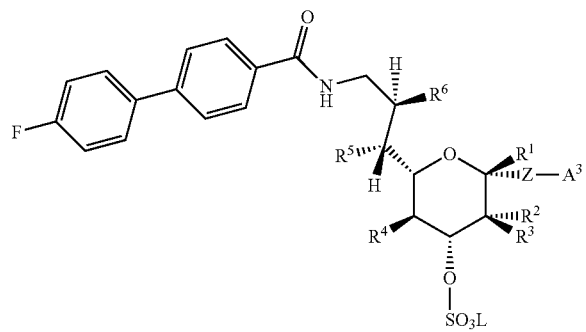
Iac
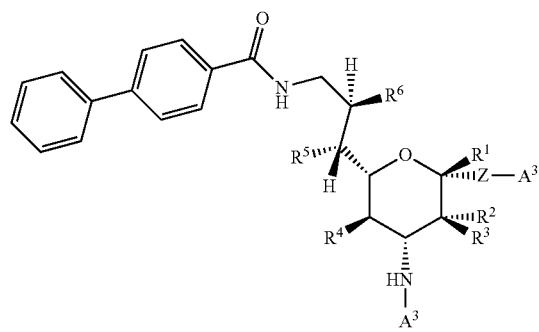
Iad
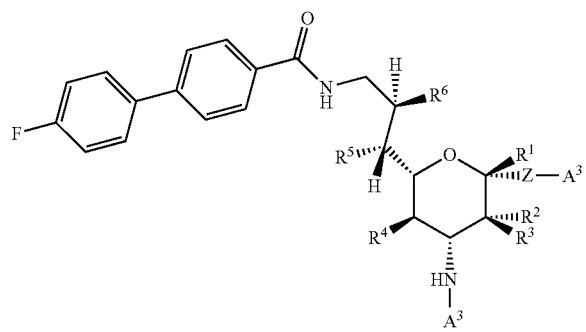
Iae
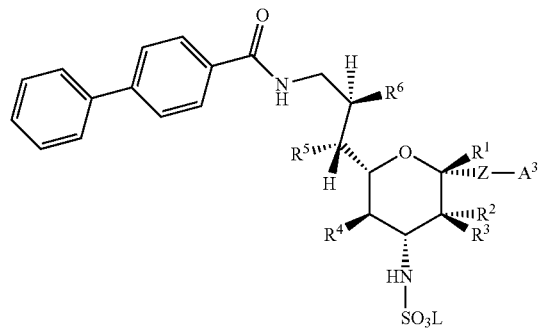
Iaf
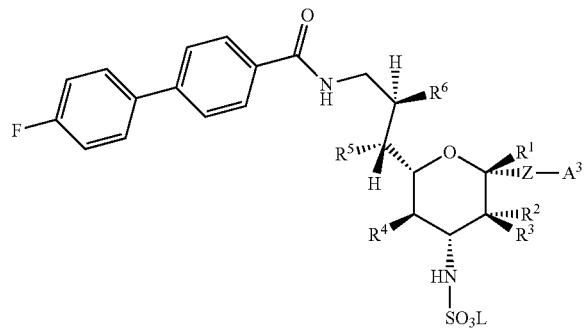
Iag
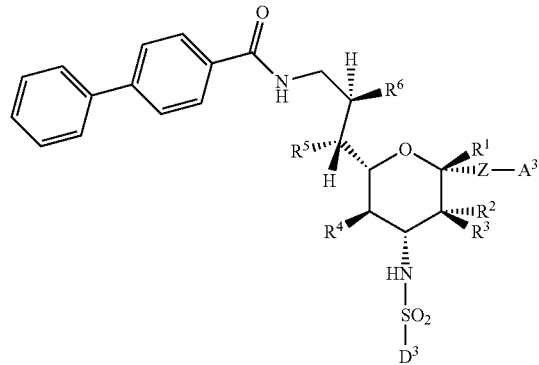
Iai
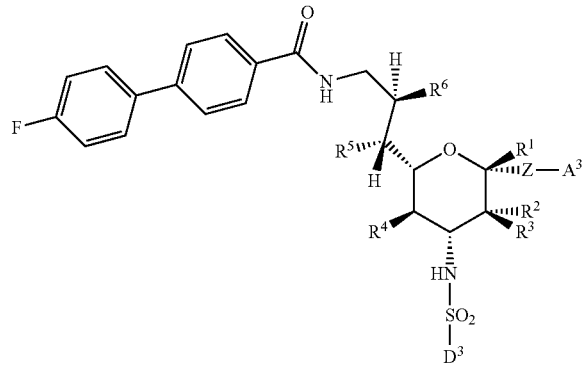

Iaj
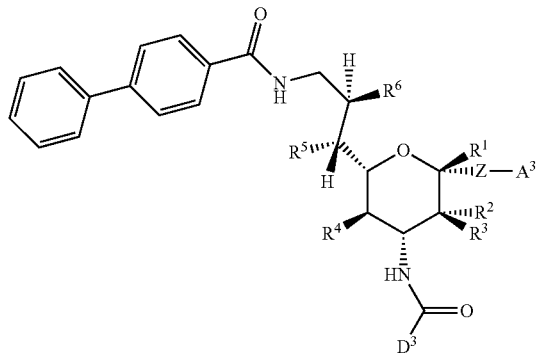
Iak
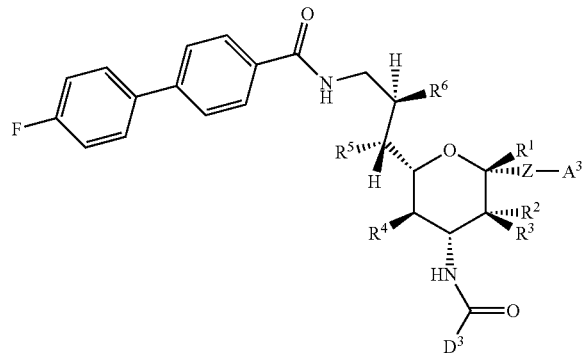
Ial
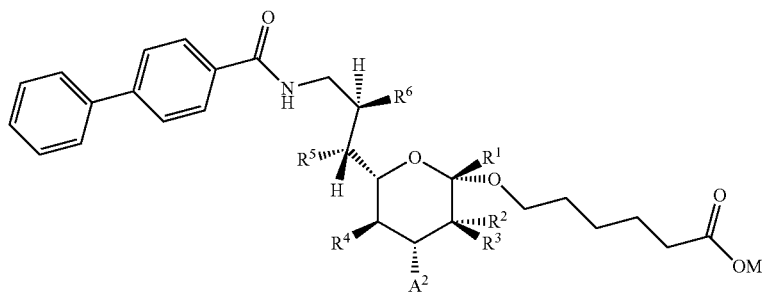
Iam
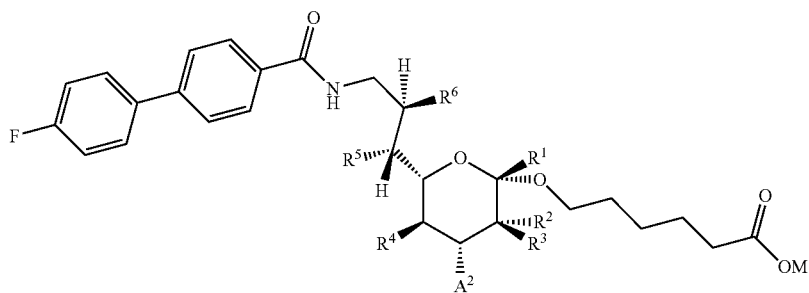
a pharmacologically tolerated salt or prodrug thereof.
6. Sialic acid derivative according to claim 1, characterized by one of the formulae (Iba)-(Ibj), where the symbols have the definitions indicated in the formula (I):
Iba
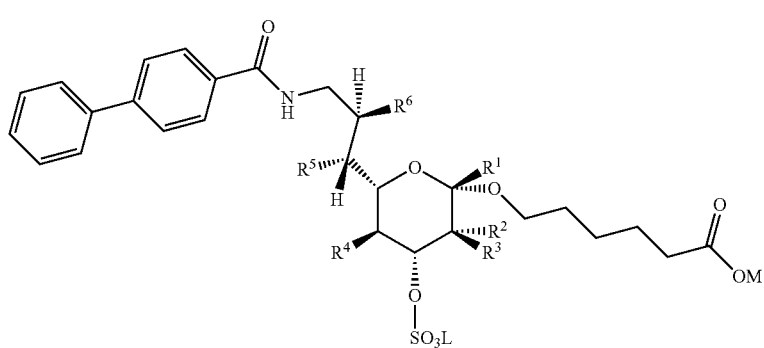

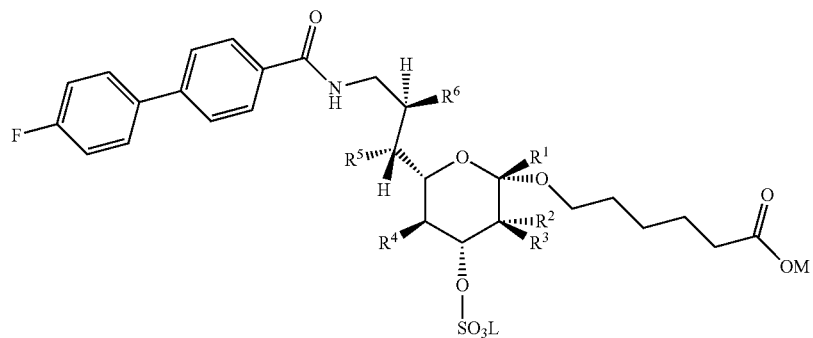
Ibb
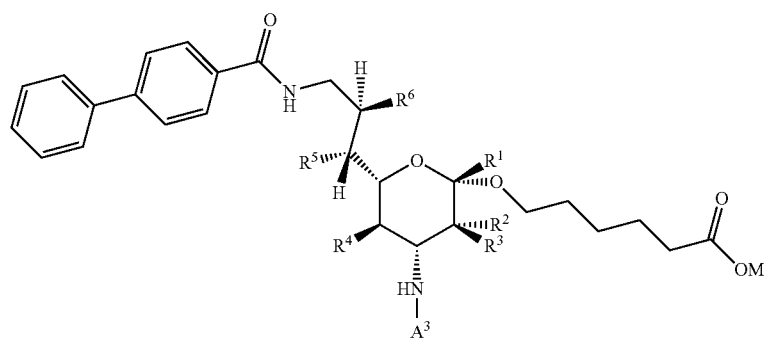
Ibc
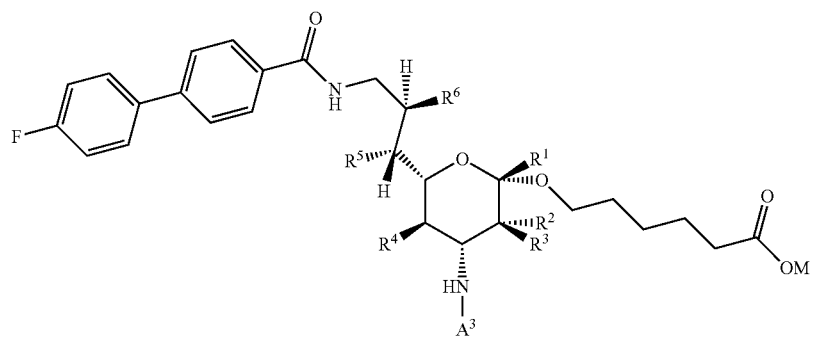
Ibd
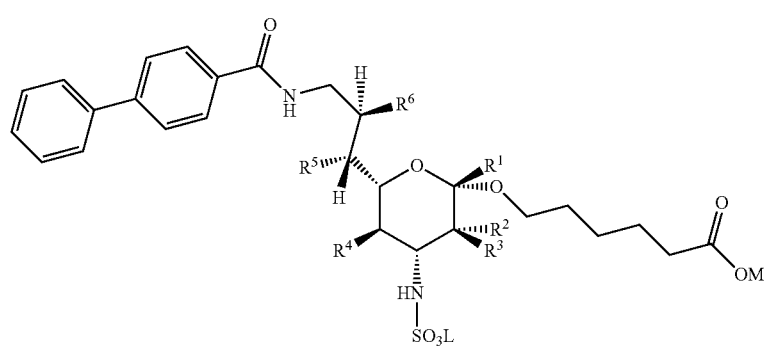
Ibe

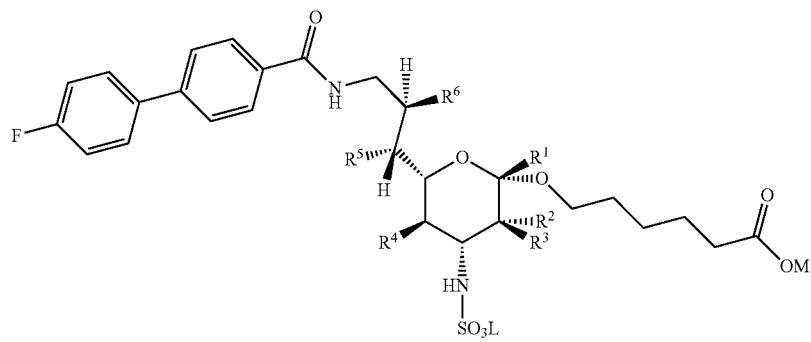
Ibf
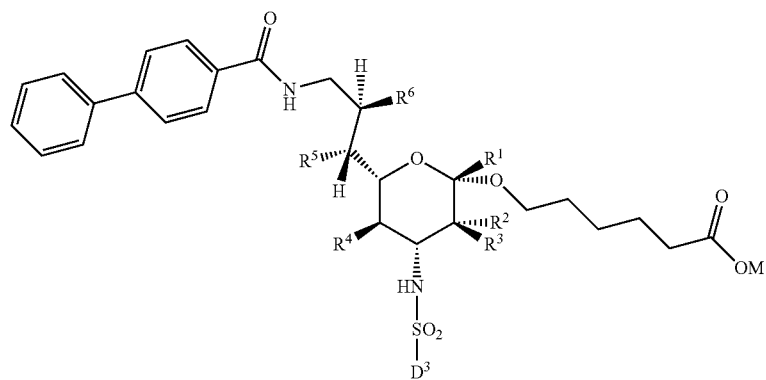
Ibg
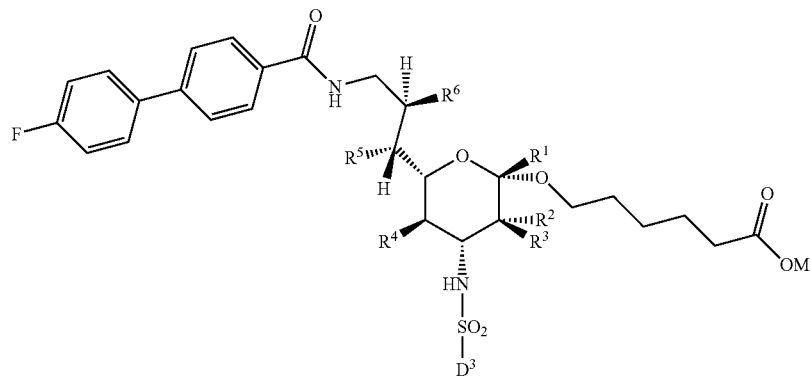
Ibh
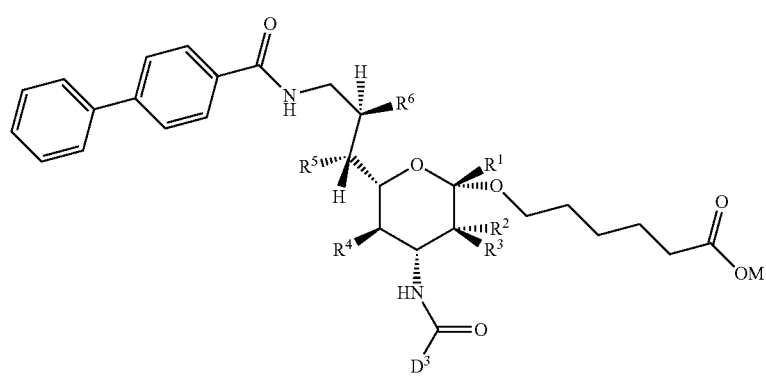
Ibi

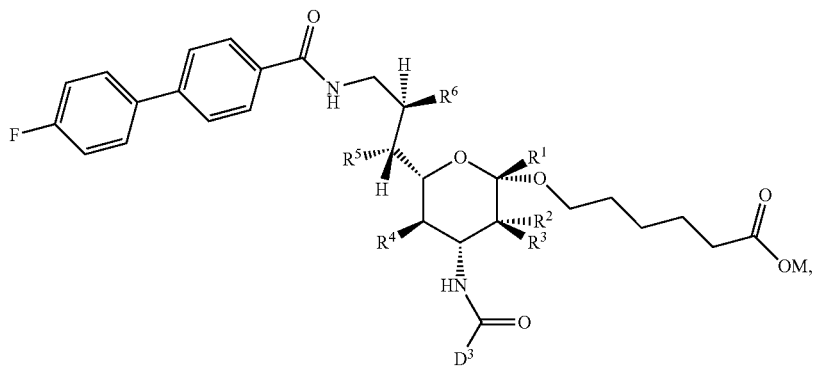
Ibj
a pharmacologically tolerated salt or prodrug thereof.
7. Sialic acid derivative of the formula (I) according to claim 1, characterized by one of the formulae (Ica)-(cj), where the symbols have the definitions indicated in the formula (I):
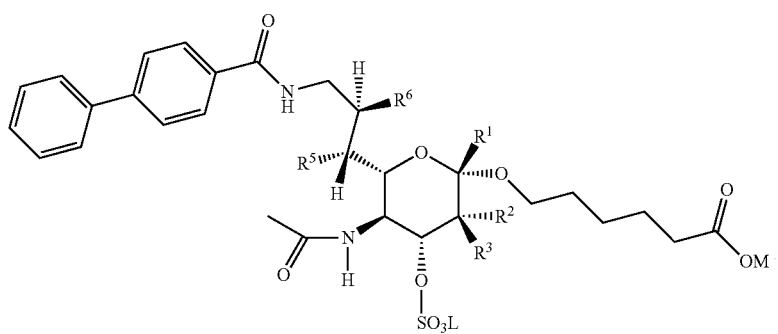
Iba
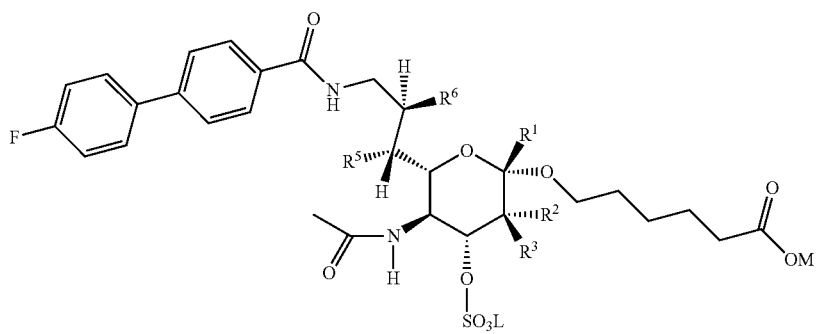
Ibb
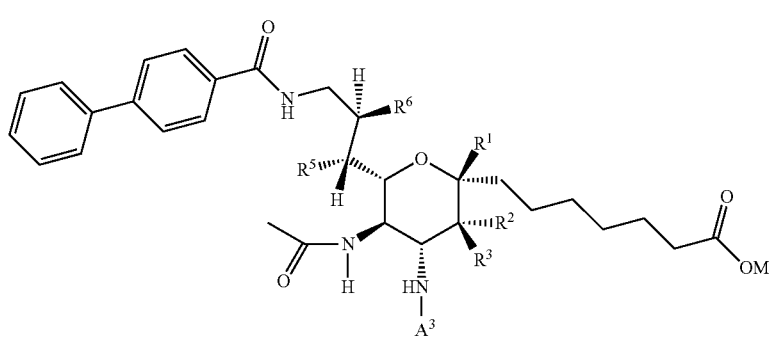
Ibc

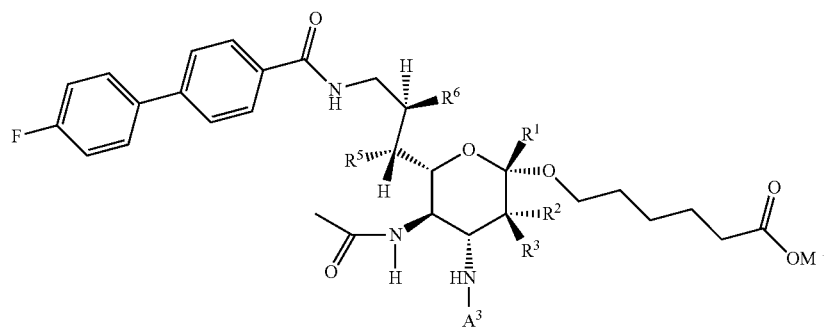
Ibd
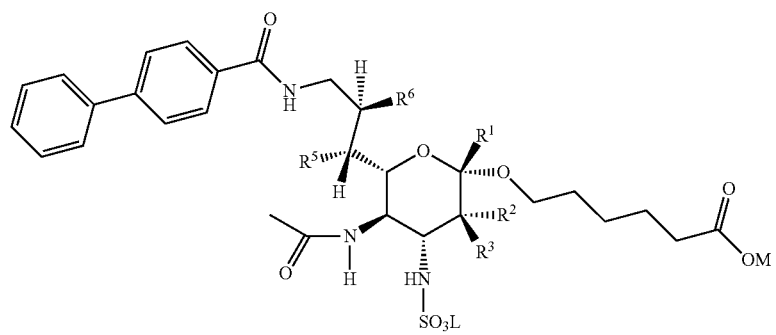
Ibe
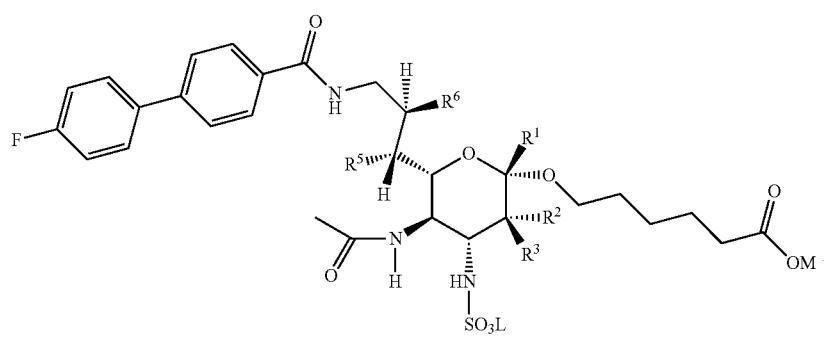
Ibf
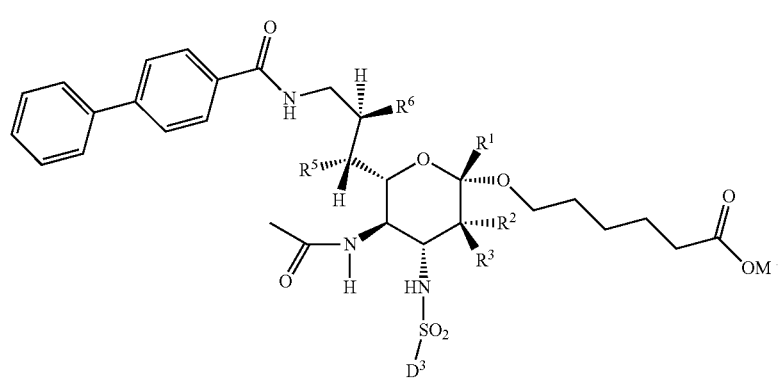
Ibg

-continued

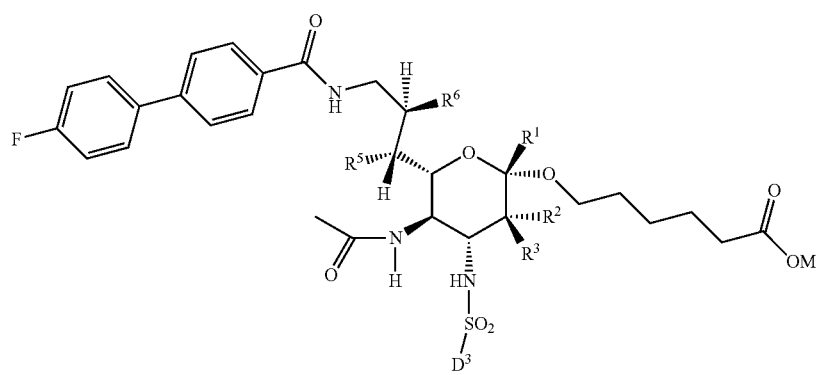
Ibh

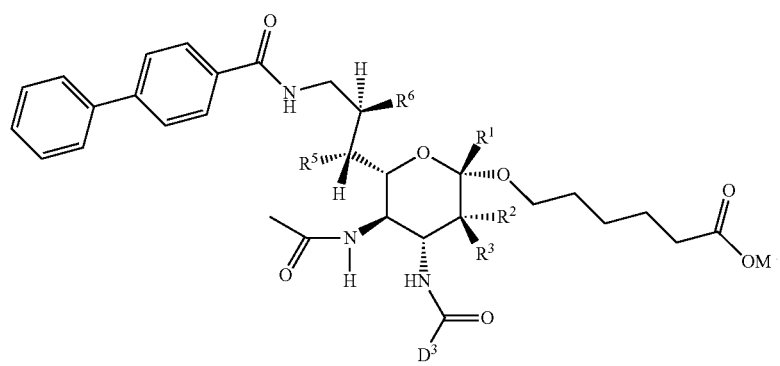
Ibi

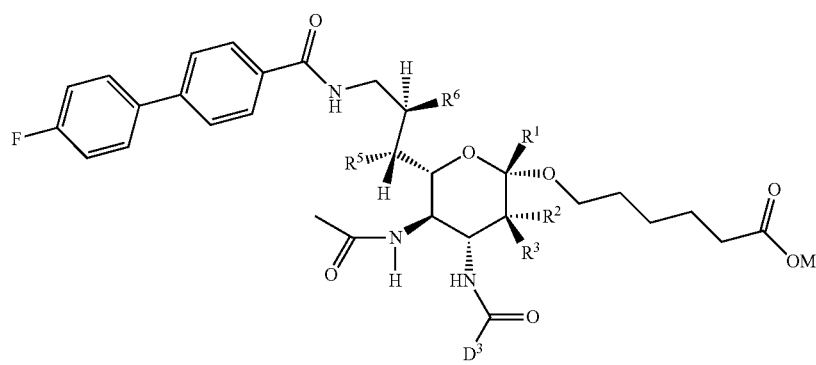
Ibj a pharmacologically tolerated salt or prodrug thereof.

8. Pharmaceutical preparation comprising at least one sialic acid derivative of the formula (I) or a pharmacologically tolerated salt or prodrug thereof according to claim 1, and a pharmacologically tolerated carrier.

9. Sialic acid derivative of the formula (I) or a pharmacologically tolerated salt or prodrug thereof according to claim 1, as medicament.

10. Method for regulating the immune system and also for the treatment of diseases whose course or activity can be influenced by the Siglec ligands, where a person affected by the disease is administered a therapeutically effective amount of a sialic acid derivative of the formula (I) or of a pharmacologically tolerated salt or prodrug thereof according to claim 1.

11. Process for preparing sialic acid derivatives of the formula (I) according to claim 1 where $R^3$=OH, where a compound of the formula (VI),

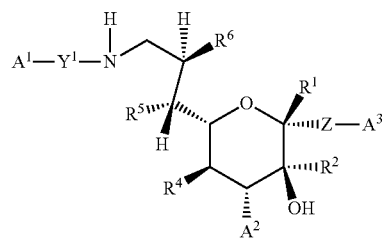
VI in which the symbols have the same definitions as in the formula (I) in claim 1, is reacted by reduction of the azide, subsequent reaction of the resultant amine with a carboxylic acid or a sulfonyl chloride, and optional elimination of protecting groups to give a sialic acid derivative of the formula (I) where $R^3$=OH.

12. Process for preparing sialic acid derivatives of the formula (I) according to claim 1 where $R^3$=H, where a compound of the formula (IV),

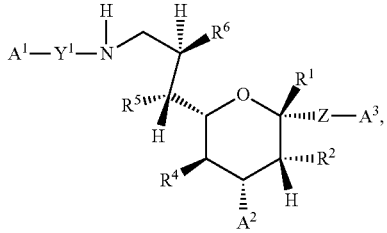

in which the symbols have the same definitions as in the formula (I) in claim 1, is reacted by reaction of the azide, subsequent reaction of the resultant amine with an activated carboxylic acid, a sulfonyl chloride or a sulfating agent, and optional elimination of protecting groups to give a sialic acid derivative of the formula (I) where $R^3$=H.

13. Process for preparing sialic acid derivatives of the formula (I) according to claim 1, where a compound of the formula (VIII)

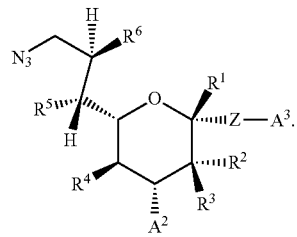

in which the symbols have the same definitions as in the formula (I) in claim 1, is reacted by reduction of the azide, subsequent reaction of the resultant amine with an activated carboxylic acid, a sulfonyl chloride or a sulfating agent, and optional elimination of protecting groups to give a sialic acid derivative of the formula (I).

14. Intermediates for the preparation of sialic acid derivatives of the formula (I) according to claim 1, selected from the group consisting of
a) compounds of the formula (III),

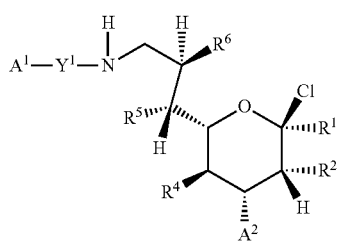

b) compound of the formula (IV)

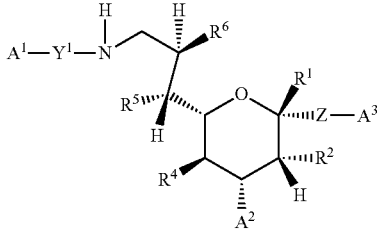

and
c) compounds of the formula (VI),

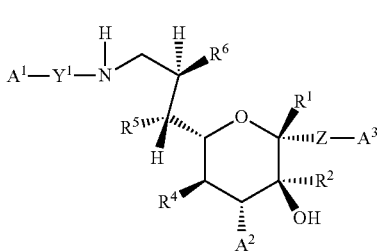

where the symbols in the formulae (III), (IV) and (VI) have the same definitions as in formula (I) in claim 1.

15. A method for treatment or prevention of allergies, autoimmune disorders, chronic inflammations, paraplegia, multiple sclerosis, cancer, viral disorders, bacterial disorders, parasitic disorders, diseases in which the immune response is disrupted in the context of B cell activation, in diseases of the hematopoietic organs and of the blood, and also for regulation of the immune system, comprising administering a therapeutically effective amount of the sialic acid derivative of the formula (I) or a pharmacologically tolerated salt or prodrug thereof according to claim 1 to a person affected thereby.

16. A method producing a medicament for the regulation of the immune system, comprising, adding to a pharmacologically tolerated carrier the sialic acid derivative of the formula (I) or a pharmacologically tolerated salt or prodrug thereof according to claim 1 to produce the medicament.

17. A method for the treatment of allergies, autoimmune disorders, chronic inflammations, paraplegia, multiple sclerosis, cancer, viral disorders, bacterial disorders, parasitic disorders, diseases in which the immune response is disrupted in the context of B cell activation, and also in diseases of the hematopoietic organs and of the blood, comprising administering a therapeutically effective amount of the sialic acid derivative of the formula (I) or a pharmacologically tolerated salt or prodrug thereof according to claim 1 to a person affected thereby.

* * * * *